US007709227B2

(12) United States Patent
Dagher

(10) Patent No.: US 7,709,227 B2
(45) Date of Patent: May 4, 2010

(54) MULTIMERIC ELP FUSION CONSTRUCTS

(75) Inventor: Suzanne Dagher, Durham, NC (US)

(73) Assignee: PhaseBio Pharmaceuticals, Inc., Morrisville, NC (US)

(*) Notice: Subject to any disclaimer, the term of this patent is extended or adjusted under 35 U.S.C. 154(b) by 226 days.

(21) Appl. No.: 11/620,034

(22) Filed: Jan. 4, 2007

(65) Prior Publication Data

US 2008/0032400 A1 Feb. 7, 2008

Related U.S. Application Data

(60) Provisional application No. 60/756,269, filed on Jan. 4, 2006.

(51) Int. Cl.
*C12P 21/04* (2006.01)
*C07K 14/00* (2006.01)

(52) U.S. Cl. ....................... 435/69.7; 530/350; 530/351

(58) Field of Classification Search ....................... None
See application file for complete search history.

(56) References Cited

U.S. PATENT DOCUMENTS

| | | | |
|---|---|---|---|
| 4,474,851 A | 10/1984 | Urry | |
| 4,749,647 A | 6/1988 | Thomas et al. | |
| 4,752,638 A | 6/1988 | Nowinski et al. | |
| 4,783,523 A | 11/1988 | Urry et al. | |
| 4,870,055 A | 9/1989 | Urry et al. | |
| 4,898,926 A | 2/1990 | Urry | |
| 5,028,419 A | 7/1991 | Pigiet | |
| 5,235,041 A | 8/1993 | Cappello et al. | |
| 5,243,038 A | 9/1993 | Ferrari et al. | |
| 5,288,514 A | 2/1994 | Ellman | |
| 5,445,934 A | 8/1995 | Fodor et al. | |
| 5,496,712 A | 3/1996 | Cappello et al. | |
| 5,514,581 A | 5/1996 | Ferrari et al. | |
| 5,519,004 A | 5/1996 | Urry | |
| 5,527,610 A | 6/1996 | Urry | |
| 5,624,711 A | 4/1997 | Sundberg et al. | |
| 5,641,648 A | 6/1997 | Ferrari et al. | |
| 5,646,016 A | 7/1997 | McCoy et al. | |
| 5,702,717 A | 12/1997 | Cha et al. | |
| 5,770,697 A | 6/1998 | Ferrari et al. | |
| 5,773,249 A | 6/1998 | Cappello et al. | |
| 5,792,506 A | 8/1998 | Buchanan et al. | |
| 5,816,259 A | 10/1998 | Rose | |
| 5,830,713 A | 11/1998 | Ferrari et al. | |
| 5,854,387 A | 12/1998 | Urry et al. | |
| 5,900,405 A | 5/1999 | Urry | |
| 5,919,657 A | 7/1999 | Hillman et al. | |
| 5,952,034 A | 9/1999 | Buchanan et al. | |
| 5,972,406 A | 10/1999 | Urry et al. | |
| 5,985,261 A | 11/1999 | White et al. | |
| 5,998,588 A | 12/1999 | Hoffman et al. | |
| 6,004,782 A | 12/1999 | Daniell et al. | |
| 6,013,857 A | 1/2000 | Deboer et al. | |
| 6,018,030 A | 1/2000 | Ferrari et al. | |
| 6,140,072 A | 10/2000 | Ferrari et al. | |
| 6,153,655 A | 11/2000 | Martinez et al. | |
| 6,184,348 B1 | 2/2001 | Ferrari et al. | |
| 6,200,598 B1 | 3/2001 | Needham | |
| 6,328,996 B1 | 12/2001 | Urry | |
| 6,329,209 B1 | 12/2001 | Wagner et al. | |
| 6,355,776 B1 | 3/2002 | Ferrari et al. | |
| 6,537,521 B2 | 3/2003 | Uzgiris | |
| 6,582,926 B1 | 6/2003 | Chilkoti | |
| 6,699,294 B2 | 3/2004 | Urry | |
| 6,852,834 B2 | 2/2005 | Chilkoti | |
| 7,364,859 B2 | 4/2008 | Chilkoti | |
| 7,429,458 B2 | 9/2008 | Chilkoti | |
| 2002/0045567 A1 | 4/2002 | Cappello et al. | |
| 2004/0110296 A1 | 6/2004 | Vargeese et al. | |
| 2004/0234609 A1 | 11/2004 | Collier et al. | |
| 2005/0255554 A1 | 11/2005 | Chilkoti | |
| 2007/0009602 A1 | 1/2007 | Setton et al. | |
| 2009/0004104 A1* | 1/2009 | Chilkoti | 424/1.69 |

FOREIGN PATENT DOCUMENTS

| | | |
|---|---|---|
| WO | 9632406 A1 | 10/1996 |
| WO | 0056774 A1 | 9/2000 |
| WO | 02074928 A2 | 9/2002 |
| WO | 03041493 A1 | 5/2003 |
| WO | 2006001806 A2 | 1/2006 |
| WO | 2006078629 A2 | 7/2006 |
| WO | 2006110292 A2 | 10/2006 |
| WO | 2008030968 A2 | 3/2008 |

OTHER PUBLICATIONS

NCBI Sequence for *Suf scrofa* Orexin-B (NP_999321)—latest entry Jun. 3, 2007.*

(Continued)

*Primary Examiner*—Suzanne M. Noakes
(74) *Attorney, Agent, or Firm*—Cooley Godward Kronish LLP

(57) ABSTRACT

ELP fusion proteins, multimeric ELP spider complexes formed of ELP fusion proteins, and methods of using the same. The construct may be in the form of an ELP spider structure complex including multi-leg moieties comprising ELP fusion proteins capable of forming covalent disulfide bonds. The multimeric fusion constructs may be employed in peptide production and purification and/or to enhance proteolytic resistance of a protein or peptide moiety in a fusion construct, by provision of the fusion protein in an ELP spider complex.

11 Claims, 13 Drawing Sheets

OTHER PUBLICATIONS

NCBI Sequence for *Homo sapien* Orexin-B (O43612)—latest entry Mar. 3, 2009.*
Chow, D. et al., "Ultra-High Expression of a Thermally Responsive Recombinant Fusion Protein in *E coli*", "Biotechnol. Prog.", Mar. 28, 2006, pp. 638-646, vol. 22.
Meyer, D. et al., "Purification of recombinant proteins by fusion with thermally-responsive polypeptides", "Nature Biotechnology", Nov. 1999, pp. 1112-1115, vol. 17.
Meyer, D. et al., "Proetin Purification by Fusion with an Environmentally Responsive Elastin Like polypeptide . . . ", "Biotechnol. Prog.", Jun. 23, 2001, pp. 720-728, vol. 17.
Chen, J. et al., "Polymer-protein conjugates, II. Affinity precipitation separation of human immunogammaglobulin by a poly(N-isopropylacry", "Biomaterials", 1990, pp. 631-634, vol. 11.
Chilkoti, A., et al., "Site-Specific Conjugation of a Temperature-Sensitive Polymer to a Genetically-Engineered Protein", "Bioconjugate Chemistry", 1994, pp. 504-507, vol. 5.
Cope, D. et al. , "Enhanced Delivery of a Monoclonal Antibody F(ab.sup.1).sub.2 Fragment to Subcutaneous Human Glioma Xenografts Using Loca", "Cancer Res.", 1990, pp. 1803-1809, vol. 50.
Vertesy, L. et al. , "Tendamistat (HOE 467), a tight-binding .alpha.-amylase inhibitor from *Streptomyces tendae* 4158", "Eur. J. Biochemistry", 1984, pp. 505-512, vol. 141.
Hauck, M. et al. , "Local Hyperthermia Improves Uptake of a Chimeric Monoclonal Antibody in a Subcutaneous Xenograft Model", "Clin. Cancer Res.", 1997, pp. 63-70, vol. 3.
Hoffman, A. , "Applications of Thermally Reversible Polymers and Hydrogels in Therapeutics and Diagnostics", "Journal of Controlled Release", 1987, pp. 297-305, vol. 6.
Holmgren, A. et al. , "Enzymatic reduction-oxidation of protein disulfides by thioredoxin", "Methods Enzymology", 1984, pp. 295-300, vol. 107.
Homgren, A. , "Thioredoxin", "Annual Rev. Biochemistry", 1985, pp. 237-271, vol. 54.
Kim, J. et al. , "Ribonuclease S-peptide as a carrier in fusion proteins", "Protein Science", 1993, pp. 348-356, vol. 2.
Kobatake, Eiry, et al., "Design and Gene Engineering Synthesis of an Extremely Thermostable Protein with Biological Activity", "Biomacromolecules", 2000, pp. 382-386, vol. 1.
Lavallie, E. et al. , "A Thioredoxin Gene Fusion Expression System That Circumvents Inclusion Body Formation in the *E. coli* Cytoplasm", "Bio/Technology", 1993, pp. 187-193, vol. 11.
Maina, C. et al. , "An *Eschericia coli* vector to express and purify foreign proteins by fusion to and separation from maltose-binding protei", "Gene", 1988, pp. 365-373, vol. 74.
McPherson, D., et al., "Production and purification of a recombinant elastomeric polypeptide, G-(VPGVG).sub.19-VPGV from *Eschericia coli*", "Biotechnol. Prog.", 1992, pp. 347-352, vol. 8.
McPherson, D. et al. , "Product Purification by Reversible Phase Transition Following *Escherichia coli* Expression of Genes Encoding up to 251 . . . ", "Protein Expression and Purification", 1996, pp. 51-57, vol. 7.
Meyer, D. et al. , "Targeting a Genetically Engineered Elastin-like Polypeptide to Solid Tumors by Local Hypothermia", "Cancer Research", Feb. 15, 2000, pp. 1548-1554, vol. 61, No. 4.
Meyer, D. et al. , "Drug targeting using thermally responsive polymers and local hyperthermia", "Journal of Controlled Release", Jul. 6, 2001, pp. 213-224, vol. 74.
Nilsson, B., et al., "Fusion proteins in biotechnology and structural biology", "Curr. Opin. Struct. Biol", 1992, pp. 569-575, vol. 2.
Nilsson, J. et al. , "Affinity Fusion Strategies for Detection, Purification, and Immobilization of Recombinant Proteins", "Protein Expression and Purification", 1997, pp. 1-16, vol. 11.
Ong, E. et al. , "The cellulose-binding domains of cellulases: tools for biotechnology", "Trends. Biotechnol", 1989, pp. 239-243, vol. 7.
Porath, J. et al. , "Immobilized metal ion affinity chromatography", "Prot. Expr. Purif.", 1992, pp. 262-282, vol. 3.
Smith, P. et al. , "Measurement of protein using bicinchonic acid", "Anal. Biochem.", 1986, pp. 76-85, vol. 150.
Smith, D. et al. , "Single-step purification of polypeptides expressed in *Escherichia coli* as fusions with glutathione S-transferase", "Gene", 1988, pp. 31-40, vol. 67.
Smith, P. et al. , "A plasmid expression system for quantitative in vivo biotinylation of thioredoxin fusion proteins in *Escherichia coli*", "Nucleic Acids Research", 1998, pp. 1414-1420, vol. 26, No. 6.
Smith, M. et al. , "Chelating Peptide-immobilized Metal Ion Affinity Chromatography, The Journal of Biological Chemistry", "The Journal of Biological Chemistry", 1988, pp. 7211-7215, vol. 263, No. 15.
Su, X. et al., "Recombinant Porcine IumorNecrosis Factor Alpha in a Novel *E. coli* Expression System", "Biotechniques", 1992, pp. 756-765, vol. 13.
Tsao, Kwe-Lan, et al., "A versatile plasmid expression vector for the production of biotinylated proteins by site-specific, enzymatic modificati", "Gene", 1996, pp. 59-64, vol. 169.
Uhlen, M. et al. , "Gene Fusions for Purpose of Expression: An Introduction", "Methods of Enzymology", 1990, pp. 129-143, vol. 185.
Urry, D. et al. , "Phase-structure Transitions of the Elastin Polypentapeptide-water system within the framework of composition-temperature", "Biopolymers", 1985, pp. 2345-2346, vol. 24.
Urry, D. , "Entropic Elastic Processes in Protein Mechanisms. I. Elastic Structure Due to an Inverse Temperature Transition and . . . ", "Journal of Protein Chemistry", 1988, pp. 1-34, vol. 7, No. 1.
Urry, D. et al., "Temperature of Polypeptide Inverse Temperature Transition Depends on Mean Residue Hydrophobicity", "J. Am. Chem. Soc.", 1991, pp. 4346-4348, vol. 113.
Urry, D. , "Free Energy Transduction in Polypeptides and Proteins Based on Inverse Temperature Transitions", "Prog. Biophys. Molec. Biol.,", 1992, pp. 23-57, vol. 57.
Urry, D., "Physical Chemistry of Biological Free Energy Transduction as Demonstrated by Elastic Protein-Based Polymers", "J. Phys. Chem. B.", 1997, pp. 11007-11028, vol. 101, No. 51.
Co-pending U.S. Appl. No. 12/335,235.
Co-pending U.S. Appl. No. 12/522,139.

* cited by examiner

A=SD34–ELP4–60–IFNA2bSD
B=SD34–ELP1–90–IFNA2bSD
C=SD22–ELP4–60–IFNA2bSD
D=SD22–ELP1–90–IFNA2bSD
E=SD35–IFNA2bSD–ELP1–90
F=SD35–IFNA2bSD–ELP4–60
G=SD37–IFNA2bSD–ELP1–90
H=SD37–IFNA2bSD–ELP4–60
I=SD31–IFNA2bSD–ELP4–60
J=SD31–IFNA2bSD–ELP1–90

M=PROTEIN MARKER
1=SONICATE
2=PELLET
3=LYSATE

A=SD22–ELP1–90–IFNA2bSD
B=SD22–ELP4–60–IFNA2bSD
C=SD31–IFNA2bSD–ELP1–90
D=SD31–IFNA2bSD–ELP4–60
E=SD34–IFNA2bSD–ELP1–90
F=SD34–IFNA2bSD–ELP4–60

M=PROTEIN MARKER
1=SONICATE
2=PELLET
3=LYSATE
4=Tt1
5=Tt2

A=SD22ELP1–90–IFNA2bSD
B=SD22ELP4–60–IFNA2bSD
C=SD31ELP1–90–IFNA2bSD
D=SD31ELP4–60–IFNA2bSD
E=SD34ELP1–90–IFNA2bSD

M=PROTEIN MARKER
1=Tt2
2=Tt2+ELP1–90–TEV1
3=INSOLUBLE IN 1M NaCl
4=SOLUBLE IN 1M NaCl

SEQUENCE LISTING

<160> NUMBER OF SEQ ID NOS: 87

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Ile Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be be any amino acid, natural or
nonnatural

<400> SEQUENCE: 3

Xaa Gly Val Pro Gly
1 5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Val Gly Val Pro Gly
1 5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Val Pro Ala Val Gly
1 5

<210> SEQ ID NO 6
<211> LENGTH: 5
<212> TYPE: PRT
<213> ORGANISM: Artificial Sequence -continued
<220> FEATURE:
<223> OTHER INFORMATION: Synthetic Construct

<400> SEQUENCE: 6

Gly Val Gly Ile Pro
1 5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Val Gly Leu Pro Gly
1 5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be any amino acid, natural or
nonnatural

<400> SEQUENCE: 8

Val Pro Gly Xaa Gly
1 5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ala Val Gly Pro Gly
1 5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ile Pro Gly Val Gly
1 5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be any amino acid, natural or
nonnatural

<400> SEQUENCE: 11

-continued

Ile Pro Gly Xaa Gly
1 5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Leu Pro Gly Val Gly
1 5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be any amino acid, natural or nonnatural

<400> SEQUENCE: 13

Leu Pro Gly Xaa Gly
1 5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Val Ala Pro Gly Val Gly
1 5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Gly Val Gly Val Pro Gly Val Gly
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Val Pro Gly Phe Gly Val Gly Ala Gly
1 5

<210> SEQ ID NO 17
<211> LENGTH: 9
<212> TYPE: PRT
<213> ORGANISM: Artificial Sequence -continued
<220> FEATURE:
<223> OTHER INFORMATION: Synthetic Construct

<400> SEQUENCE: 17

Val Pro Gly Val Gly Val Pro Gly Gly
1               5

<210> SEQ ID NO 18
<211> LENGTH: 51
<212> TYPE: PRT
<213> ORGANISM: Artificial Sequence
<220> FEATURE:
<223> OTHER INFORMATION: Synthetic Construct

<400> SEQUENCE: 18

Gly Val Gly Val Pro Gly Val Gly Val Pro Gly Cys Cys Val Pro Gly
1               5                   10                  15

Ala Gly Val Pro Gly Val Gly Val Pro Gly Val Gly Val Pro Gly Val
            20                  25                  30

Gly Val Pro Gly Gly Gly Val Pro Gly Ala Gly Val Pro Gly Gly Gly
        35                  40                  45

Val Pro Gly
    50

<210> SEQ ID NO 19
<211> LENGTH: 153
<212> TYPE: DNA
<213> ORGANISM: Artificial Sequence
<220> FEATURE:
<223> OTHER INFORMATION: Synthetic Construct

<400> SEQUENCE: 19
ggcgtgggtg ttccgggcgt gggtgttccg ggttgctgcg tgccgggcgc aggtgttcct     60
ggtgtaggtg tgccgggtgt tggtgtgccg ggtgttggtg taccaggtgg cggtgttccg    120
ggtgcaggcg ttccgggtgg cggtgtgccg ggc                                 153

<210> SEQ ID NO 20
<211> LENGTH: 51
<212> TYPE: PRT
<213> ORGANISM: Artificial Sequence
<220> FEATURE:
<223> OTHER INFORMATION: Synthetic Construct

<400> SEQUENCE: 20

Gly Val Gly Val Pro Gly Val Gly Val Pro Gly Cys Gly Val Pro Gly
1               5                   10                  15

Ala Gly Val Pro Gly Val Gly Val Pro Gly Val Gly Val Pro Gly Val
            20                  25                  30

Gly Val Pro Gly Cys Gly Val Pro Gly Ala Gly Val Pro Gly Gly Gly
        35                  40                  45

Val Pro Gly
    50

<210> SEQ ID NO 21
<211> LENGTH: 153
<212> TYPE: DNA
<213> ORGANISM: Artificial Sequence
<220> FEATURE:
<223> OTHER INFORMATION: Synthetic construct

<400> SEQUENCE: 21
ggcgtgggtg ttccgggcgt gggtgttccg ggttgcgggg tgccgggcgc aggtgttcct     60
ggtgtaggtg tgccgggtgt tggtgtgccg ggtgttggtg taccaggttg cggtgttccg 120
ggtgcaggcg ttccgggtgg cggtgtgccg ggc 153

<210> SEQ ID NO 22
<211> LENGTH: 646
<212> TYPE: PRT
<213> ORGANISM: Artificial Sequence
<220> FEATURE:
<223> OTHER INFORMATION: Synthetic construct

<400> SEQUENCE: 22

```
Met Cys Cys Pro Met Gly Gly Pro Gly Val Gly Val Pro Gly Val Gly
1               5                   10                  15

Val Pro Gly Gly Gly Val Pro Gly Ala Gly Val Pro Gly Val Gly Val
            20                  25                  30

Pro Gly Val Gly Val Pro Gly Val Gly Val Pro Gly Gly Gly Val Pro
        35                  40                  45

Gly Ala Gly Val Pro Gly Gly Gly Val Pro Gly Val Gly Val Pro Gly
    50                  55                  60

Val Gly Val Pro Gly Gly Gly Val Pro Gly Ala Gly Val Pro Gly Val
65                  70                  75                  80

Gly Val Pro Gly Val Gly Val Pro Gly Val Gly Val Pro Gly Gly Gly
                85                  90                  95

Val Pro Gly Ala Gly Val Pro Gly Gly Gly Val Pro Gly Val Gly Val
            100                 105                 110

Pro Gly Val Gly Val Pro Gly Gly Gly Val Pro Gly Ala Gly Val Pro
        115                 120                 125

Gly Val Gly Val Pro Gly Val Gly Val Pro Gly Val Gly Val Pro Gly
    130                 135                 140

Gly Gly Val Pro Gly Ala Gly Val Pro Gly Gly Gly Val Pro Gly Val
145                 150                 155                 160

Gly Val Pro Gly Val Gly Val Pro Gly Gly Gly Val Pro Gly Ala Gly
                165                 170                 175

Val Pro Gly Val Gly Val Pro Gly Val Gly Val Pro Gly Val Gly Val
            180                 185                 190

Pro Gly Gly Gly Val Pro Gly Ala Gly Val Pro Gly Gly Gly Val Pro
        195                 200                 205

Gly Val Gly Val Pro Gly Val Gly Val Pro Gly Gly Gly Val Pro Gly
    210                 215                 220

Ala Gly Val Pro Gly Val Gly Val Pro Gly Val Gly Val Pro Gly Val
225                 230                 235                 240

Gly Val Pro Gly Gly Gly Val Pro Gly Ala Gly Val Pro Gly Gly Gly
                245                 250                 255

Val Pro Gly Val Gly Val Pro Gly Val Gly Val Pro Gly Gly Gly Val
            260                 265                 270

Pro Gly Ala Gly Val Pro Gly Val Gly Val Pro Gly Val Gly Val Pro
        275                 280                 285

Gly Val Gly Val Pro Gly Gly Gly Val Pro Gly Ala Gly Val Pro Gly
    290                 295                 300

Gly Gly Val Pro Gly Val Gly Val Pro Gly Val Gly Val Pro Gly Gly
305                 310                 315                 320

Gly Val Pro Gly Ala Gly Val Pro Gly Val Gly Val Pro Gly Val Gly
                325                 330                 335

Val Pro Gly Val Gly Val Pro Gly Gly Gly Val Pro Gly Ala Gly Val
```

-continued

```
            340                 345                 350

Pro Gly Gly Gly Val Pro Gly Val Gly Val Pro Gly Val Gly Val Pro
        355                 360                 365

Gly Gly Gly Val Pro Gly Ala Gly Val Pro Gly Val Gly Val Pro Gly
    370                 375                 380

Val Gly Val Pro Gly Val Gly Val Pro Gly Gly Gly Val Pro Gly Ala
385                 390                 395                 400

Gly Val Pro Gly Gly Gly Val Pro Gly Val Gly Val Pro Gly Val Gly
                405                 410                 415

Val Pro Gly Gly Gly Val Pro Gly Ala Gly Val Pro Gly Val Gly Val
            420                 425                 430

Pro Gly Val Gly Val Pro Gly Val Gly Val Pro Gly Gly Gly Val Pro
        435                 440                 445

Gly Ala Gly Val Pro Gly Gly Gly Val Pro Gly Trp Pro Ser Ser Gly
    450                 455                 460

Asp Tyr Asp Ile Pro Thr Thr Glu Asn Leu Tyr Phe Gln Gly Ala His
465                 470                 475                 480

Met Cys Asp Leu Pro Gln Thr His Ser Leu Gly Ser Arg Arg Thr Leu
                485                 490                 495

Met Leu Leu Ala Gln Met Arg Arg Ile Ser Leu Phe Ser Cys Leu Lys
            500                 505                 510

Asp Arg His Asp Phe Gly Phe Pro Gln Glu Glu Phe Gly Asn Gln Phe
        515                 520                 525

Gln Lys Ala Glu Thr Ile Pro Val Leu His Glu Met Ile Gln Gln Ile
    530                 535                 540

Phe Asn Leu Phe Ser Thr Lys Asp Ser Ser Ala Ala Trp Asp Glu Thr
545                 550                 555                 560

Leu Leu Asp Lys Phe Tyr Thr Glu Leu Tyr Gln Gln Leu Asn Asp Leu
                565                 570                 575

Glu Ala Cys Val Ile Gln Gly Val Gly Val Thr Glu Thr Pro Leu Met
            580                 585                 590

Lys Glu Asp Ser Ile Leu Ala Val Arg Lys Tyr Phe Gln Arg Ile Thr
        595                 600                 605

Leu Tyr Leu Lys Glu Lys Lys Tyr Ser Pro Cys Ala Trp Glu Val Val
    610                 615                 620

Arg Ala Glu Ile Met Arg Ser Phe Ser Leu Ser Thr Asn Leu Gln Glu
625                 630                 635                 640

Ser Leu Arg Ser Lys Glu
                645


<210> SEQ ID NO 23
<211> LENGTH: 496
<212> TYPE: PRT
<213> ORGANISM: Artificial Sequence
<220> FEATURE:
<223> OTHER INFORMATION: Synthetic construct

<400> SEQUENCE: 23

Met Cys Cys Pro Met Gly Gly Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
```

-continued

```
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Val Gly Val Pro Gly
    210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
    290                 295                 300

Val Gly Val Pro Gly Trp Pro Ser Ser Gly Asp Tyr Asp Ile Pro Thr
305                 310                 315                 320

Thr Glu Asn Leu Tyr Phe Gln Gly Ala His Met Cys Asp Leu Pro Gln
                325                 330                 335

Thr His Ser Leu Gly Ser Arg Arg Thr Leu Met Leu Leu Ala Gln Met
            340                 345                 350

Arg Arg Ile Ser Leu Phe Ser Cys Leu Lys Asp Arg His Asp Phe Gly
        355                 360                 365

Phe Pro Gln Glu Glu Phe Gly Asn Gln Phe Gln Lys Ala Glu Thr Ile
    370                 375                 380

Pro Val Leu His Glu Met Ile Gln Gln Ile Phe Asn Leu Phe Ser Thr
385                 390                 395                 400

Lys Asp Ser Ser Ala Ala Trp Asp Glu Thr Leu Leu Asp Lys Phe Tyr
                405                 410                 415

Thr Glu Leu Tyr Gln Gln Leu Asn Asp Leu Glu Ala Cys Val Ile Gln
            420                 425                 430

Gly Val Gly Val Thr Glu Thr Pro Leu Met Lys Glu Asp Ser Ile Leu
        435                 440                 445

Ala Val Arg Lys Tyr Phe Gln Arg Ile Thr Leu Tyr Leu Lys Glu Lys
    450                 455                 460

Lys Tyr Ser Pro Cys Ala Trp Glu Val Val Arg Ala Glu Ile Met Arg
465                 470                 475                 480
```

-continued

```
Ser Phe Ser Leu Ser Thr Asn Leu Gln Glu Ser Leu Arg Ser Lys Glu
                485                 490                 495


<210> SEQ ID NO 24
<211> LENGTH: 642
<212> TYPE: PRT
<213> ORGANISM: Artificial Sequence
<220> FEATURE:
<223> OTHER INFORMATION: Synthetic construct

<400> SEQUENCE: 24

Met Gly Gly Pro Gly Val Gly Val Pro Gly Val Gly Val Pro Gly Gly
1               5                   10                  15

Gly Val Pro Gly Ala Gly Val Pro Gly Val Gly Val Pro Gly Val Gly
            20                  25                  30

Val Pro Gly Val Gly Val Pro Gly Gly Gly Val Pro Gly Ala Gly Val
        35                  40                  45

Pro Gly Gly Gly Val Pro Gly Val Gly Val Pro Gly Val Gly Val Pro
    50                  55                  60

Gly Gly Gly Val Pro Gly Ala Gly Val Pro Gly Val Gly Val Pro Gly
65                  70                  75                  80

Val Gly Val Pro Gly Val Gly Val Pro Gly Gly Gly Val Pro Gly Ala
                85                  90                  95

Gly Val Pro Gly Gly Gly Val Pro Gly Val Gly Val Pro Gly Val Gly
            100                 105                 110

Val Pro Gly Gly Gly Val Pro Gly Ala Gly Val Pro Gly Val Gly Val
        115                 120                 125

Pro Gly Val Gly Val Pro Gly Val Gly Val Pro Gly Gly Gly Val Pro
    130                 135                 140

Gly Ala Gly Val Pro Gly Gly Gly Val Pro Gly Val Gly Val Pro Gly
145                 150                 155                 160

Val Gly Val Pro Gly Gly Gly Val Pro Gly Ala Gly Val Pro Gly Val
                165                 170                 175

Gly Val Pro Gly Val Gly Val Pro Gly Val Gly Val Pro Gly Gly Gly
            180                 185                 190

Val Pro Gly Ala Gly Val Pro Gly Gly Gly Val Pro Gly Val Gly Val
        195                 200                 205

Pro Gly Val Gly Val Pro Gly Gly Gly Val Pro Gly Ala Gly Val Pro
    210                 215                 220

Gly Val Gly Val Pro Gly Val Gly Val Pro Gly Val Gly Val Pro Gly
225                 230                 235                 240

Gly Gly Val Pro Gly Ala Gly Val Pro Gly Gly Gly Val Pro Gly Val
                245                 250                 255

Gly Val Pro Gly Val Gly Val Pro Gly Gly Gly Val Pro Gly Ala Gly
            260                 265                 270

Val Pro Gly Val Gly Val Pro Gly Val Gly Val Pro Gly Val Gly Val
        275                 280                 285

Pro Gly Gly Gly Val Pro Gly Ala Gly Val Pro Gly Gly Gly Val Pro
    290                 295                 300

Gly Val Gly Val Pro Gly Val Gly Val Pro Gly Gly Gly Val Pro Gly
305                 310                 315                 320

Ala Gly Val Pro Gly Val Gly Val Pro Gly Val Gly Val Pro Gly Val
                325                 330                 335

Gly Val Pro Gly Gly Gly Val Pro Gly Ala Gly Val Pro Gly Gly Gly
            340                 345                 350
```

-continued

```
Val Pro Gly Val Gly Val Pro Gly Val Gly Val Pro Gly Gly Gly Val
        355                 360                 365

Pro Gly Ala Gly Val Pro Gly Val Gly Val Pro Gly Val Gly Val Pro
    370                 375                 380

Gly Val Gly Val Pro Gly Gly Gly Val Pro Gly Ala Gly Val Pro Gly
385                 390                 395                 400

Gly Gly Val Pro Gly Val Gly Val Pro Gly Val Gly Val Pro Gly Gly
                405                 410                 415

Gly Val Pro Gly Ala Gly Val Pro Gly Val Gly Val Pro Gly Val Gly
            420                 425                 430

Val Pro Gly Val Gly Val Pro Gly Gly Gly Val Pro Gly Ala Gly Val
        435                 440                 445

Pro Gly Gly Gly Val Pro Gly Trp Pro Cys Cys Ser Ser Gly Asp Ile
    450                 455                 460

Pro Thr Thr Glu Asn Leu Tyr Phe Gln Gly Ala His Met Cys Asp Leu
465                 470                 475                 480

Pro Gln Thr His Ser Leu Gly Ser Arg Arg Thr Leu Met Leu Leu Ala
                485                 490                 495

Gln Met Arg Arg Ile Ser Leu Phe Ser Cys Leu Lys Asp Arg His Asp
            500                 505                 510

Phe Gly Phe Pro Gln Glu Glu Phe Gly Asn Gln Phe Gln Lys Ala Glu
        515                 520                 525

Thr Ile Pro Val Leu His Glu Met Ile Gln Gln Ile Phe Asn Leu Phe
    530                 535                 540

Ser Thr Lys Asp Ser Ser Ala Ala Trp Asp Glu Thr Leu Leu Asp Lys
545                 550                 555                 560

Phe Tyr Thr Glu Leu Tyr Gln Gln Leu Asn Asp Leu Glu Ala Cys Val
                565                 570                 575

Ile Gln Gly Val Gly Val Thr Glu Thr Pro Leu Met Lys Glu Asp Ser
            580                 585                 590

Ile Leu Ala Val Arg Lys Tyr Phe Gln Arg Ile Thr Leu Tyr Leu Lys
        595                 600                 605

Glu Lys Lys Tyr Ser Pro Cys Ala Trp Glu Val Val Arg Ala Glu Ile
    610                 615                 620

Met Arg Ser Phe Ser Leu Ser Thr Asn Leu Gln Glu Ser Leu Arg Ser
625                 630                 635                 640

Lys Glu


<210> SEQ ID NO 25
<211> LENGTH: 492
<212> TYPE: PRT
<213> ORGANISM: Artificial Sequence
<220> FEATURE:
<223> OTHER INFORMATION: Synthetic construct

<400> SEQUENCE: 25

Met Gly Gly Pro Gly Val Gly Val Pro Gly Val Gly Val Pro Gly Val
1               5                   10                  15

Gly Val Pro Gly Val Gly Val Pro Gly Val Gly Val Pro Gly Val Gly
            20                  25                  30

Val Pro Gly Val Gly Val Pro Gly Val Gly Val Pro Gly Val Gly Val
        35                  40                  45

Pro Gly Val Gly Val Pro Gly Val Gly Val Pro Gly Val Gly Val Pro
    50                  55                  60
```

-continued

```
Gly Val Gly Val Pro Gly Val Gly Val Pro Gly Val Gly Val Pro Gly
65                  70                  75                  80

Val Gly Val Pro Gly Val Gly Val Pro Gly Val Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Val Gly Val Pro Gly Val Gly Val Pro Gly Val Gly Val Pro
    130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Val Pro Gly Val Gly Val Pro Gly
225                 230                 235                 240

Val Gly Val Pro Gly Val Gly Val Pro Gly Val Gly Val Pro Gly Val
                245                 250                 255

Gly Val Pro Gly Val Gly Val Pro Gly Val Gly Val Pro Gly Val Gly
            260                 265                 270

Val Pro Gly Val Gly Val Pro Gly Val Gly Val Pro Gly Val Gly Val
        275                 280                 285

Pro Gly Val Gly Val Pro Gly Val Gly Val Pro Gly Val Gly Val Pro
    290                 295                 300

Gly Trp Pro Cys Cys Ser Ser Gly Asp Ile Pro Thr Thr Glu Asn Leu
305                 310                 315                 320

Tyr Phe Gln Gly Ala His Met Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460

Cys Ala Trp Glu Val Val Arg Ala Glu Ile Met Arg Ser Phe Ser Leu
465                 470                 475                 480

Ser Thr Asn Leu Gln Glu Ser Leu Arg Ser Lys Glu
```

-continued

```
            485                 490


<210> SEQ ID NO 26
<211> LENGTH: 642
<212> TYPE: PRT
<213> ORGANISM: Artificial Sequence
<220> FEATURE:
<223> OTHER INFORMATION: Synthetic construct

<400> SEQUENCE: 26

Met Gly Gly Pro Gly Val Gly Val Pro Gly Val Gly Val Pro Gly Gly
1               5                   10                  15

Gly Val Pro Gly Ala Gly Val Pro Gly Val Gly Val Pro Gly Val Gly
            20                  25                  30

Val Pro Gly Val Gly Val Pro Gly Gly Gly Val Pro Gly Ala Gly Val
        35                  40                  45

Pro Gly Gly Gly Val Pro Gly Val Gly Val Pro Gly Val Gly Val Pro
    50                  55                  60

Gly Gly Gly Val Pro Gly Ala Gly Val Pro Gly Val Gly Val Pro Gly
65                  70                  75                  80

Val Gly Val Pro Gly Val Gly Val Pro Gly Gly Gly Val Pro Gly Ala
                85                  90                  95

Gly Val Pro Gly Gly Gly Val Pro Gly Val Gly Val Pro Gly Val Gly
            100                 105                 110

Val Pro Gly Gly Gly Val Pro Gly Ala Gly Val Pro Gly Val Gly Val
        115                 120                 125

Pro Gly Val Gly Val Pro Gly Val Gly Val Pro Gly Gly Gly Val Pro
    130                 135                 140

Gly Ala Gly Val Pro Gly Gly Gly Val Pro Gly Val Gly Val Pro Gly
145                 150                 155                 160

Val Gly Val Pro Gly Gly Gly Val Pro Gly Ala Gly Val Pro Gly Val
                165                 170                 175

Gly Val Pro Gly Val Gly Val Pro Gly Val Gly Val Pro Gly Gly Gly
            180                 185                 190

Val Pro Gly Ala Gly Val Pro Gly Gly Gly Val Pro Gly Val Gly Val
        195                 200                 205

Pro Gly Val Gly Val Pro Gly Gly Gly Val Pro Gly Ala Gly Val Pro
    210                 215                 220

Gly Val Gly Val Pro Gly Val Gly Val Pro Gly Val Gly Val Pro Gly
225                 230                 235                 240

Gly Gly Val Pro Gly Ala Gly Val Pro Gly Gly Gly Val Pro Gly Val
                245                 250                 255

Gly Val Pro Gly Val Gly Val Pro Gly Gly Gly Val Pro Gly Ala Gly
            260                 265                 270

Val Pro Gly Val Gly Val Pro Gly Val Gly Val Pro Gly Val Gly Val
        275                 280                 285

Pro Gly Gly Gly Val Pro Gly Ala Gly Val Pro Gly Gly Gly Val Pro
    290                 295                 300

Gly Val Gly Val Pro Gly Val Gly Val Pro Gly Gly Gly Val Pro Gly
305                 310                 315                 320

Ala Gly Val Pro Gly Val Gly Val Pro Gly Val Gly Val Pro Gly Val
                325                 330                 335

Gly Val Pro Gly Gly Gly Val Pro Gly Ala Gly Val Pro Gly Gly Gly
            340                 345                 350

Val Pro Gly Val Gly Val Pro Gly Val Gly Val Pro Gly Gly Gly Val
```

-continued

```
        355                 360                 365

Pro Gly Ala Gly Val Pro Gly Val Gly Val Pro Gly Val Gly Val Pro
    370                 375                 380

Gly Val Gly Val Pro Gly Gly Gly Val Pro Gly Ala Gly Val Pro Gly
385                 390                 395                 400

Gly Gly Val Pro Gly Val Gly Val Pro Gly Val Gly Val Pro Gly Gly
                405                 410                 415

Gly Val Pro Gly Ala Gly Val Pro Gly Val Gly Val Pro Gly Val Gly
            420                 425                 430

Val Pro Gly Val Gly Val Pro Gly Gly Gly Val Pro Gly Ala Gly Val
        435                 440                 445

Pro Gly Gly Gly Val Pro Gly Trp Pro Ser Ser Gly Asp Tyr Asp Ile
    450                 455                 460

Pro Thr Thr Glu Asn Leu Tyr Phe Gln Gly Ala His Met Cys Asp Leu
465                 470                 475                 480

Pro Gln Thr His Ser Leu Gly Ser Arg Arg Thr Leu Met Leu Leu Ala
                485                 490                 495

Gln Met Arg Arg Ile Ser Leu Phe Ser Cys Leu Lys Asp Arg His Asp
            500                 505                 510

Phe Gly Phe Pro Gln Glu Glu Phe Gly Asn Gln Phe Gln Lys Ala Glu
        515                 520                 525

Thr Ile Pro Val Leu His Glu Met Ile Gln Gln Ile Phe Asn Leu Phe
    530                 535                 540

Ser Thr Lys Asp Ser Ser Ala Ala Trp Asp Glu Thr Leu Leu Asp Lys
545                 550                 555                 560

Phe Tyr Thr Glu Leu Tyr Gln Gln Leu Asn Asp Leu Glu Ala Cys Val
                565                 570                 575

Ile Gln Gly Val Gly Val Thr Glu Thr Pro Leu Met Lys Glu Asp Ser
            580                 585                 590

Ile Leu Ala Val Arg Lys Tyr Phe Gln Arg Ile Thr Leu Tyr Leu Lys
        595                 600                 605

Glu Lys Lys Tyr Ser Pro Cys Ala Trp Glu Val Val Arg Ala Glu Ile
    610                 615                 620

Met Arg Ser Phe Ser Leu Ser Thr Asn Leu Gln Glu Ser Leu Arg Ser
625                 630                 635                 640

Lys Glu


<210> SEQ ID NO 27
<211> LENGTH: 492
<212> TYPE: PRT
<213> ORGANISM: Artificial Sequence
<220> FEATURE:
<223> OTHER INFORMATION: Synthetic construct

<400> SEQUENCE: 27

Met Gly Gly Pro Gly Val Gly Val Pro Gly Val Gly Val Pro Gly Val
1               5                   10                  15

Gly Val Pro Gly Val Gly Val Pro Gly Val Gly Val Pro Gly Val Gly
            20                  25                  30

Val Pro Gly Val Gly Val Pro Gly Val Gly Val Pro Gly Val Gly Val
        35                  40                  45

Pro Gly Val Gly Val Pro Gly Val Gly Val Pro Gly Val Gly Val Pro
    50                  55                  60

Gly Val Gly Val Pro Gly Val Gly Val Pro Gly Val Gly Val Pro Gly
65                  70                  75                  80
```

-continued

```
Val Gly Val Pro Gly Val Gly Val Pro Gly Val Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Val Gly Val Pro Gly Val Gly Val Pro Gly Val Gly Val Pro
    130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Val Pro Gly Val Gly Val Pro Gly
225                 230                 235                 240

Val Gly Val Pro Gly Val Gly Val Pro Gly Val Gly Val Pro Gly Val
                245                 250                 255

Gly Val Pro Gly Val Gly Val Pro Gly Val Gly Val Pro Gly Val Gly
            260                 265                 270

Val Pro Gly Val Gly Val Pro Gly Val Gly Val Pro Gly Val Gly Val
        275                 280                 285

Pro Gly Val Gly Val Pro Gly Val Gly Val Pro Gly Val Gly Val Pro
    290                 295                 300

Gly Trp Pro Ser Ser Gly Asp Tyr Asp Ile Pro Thr Thr Glu Asn Leu
305                 310                 315                 320

Tyr Phe Gln Gly Ala His Met Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460

Cys Ala Trp Glu Val Val Arg Ala Glu Ile Met Arg Ser Phe Ser Leu
465                 470                 475                 480

Ser Thr Asn Leu Gln Glu Ser Leu Arg Ser Lys Glu
                485                 490
```

-continued

<210> SEQ ID NO 28
<211> LENGTH: 638
<212> TYPE: PRT
<213> ORGANISM: Artificial Sequence
<220> FEATURE:
<223> OTHER INFORMATION: Synthetic construct

<400> SEQUENCE: 28

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Cys
                165                 170                 175

Cys Gly Gln Gly Gly Met Gly Gly Pro Gly Val Gly Val Pro Gly Val
            180                 185                 190

Gly Val Pro Gly Gly Gly Val Pro Gly Ala Gly Val Pro Gly Val Gly
        195                 200                 205

Val Pro Gly Val Gly Val Pro Gly Val Gly Val Pro Gly Gly Gly Val
    210                 215                 220

Pro Gly Ala Gly Val Pro Gly Gly Gly Val Pro Gly Val Gly Val Pro
225                 230                 235                 240

Gly Val Gly Val Pro Gly Gly Gly Val Pro Gly Ala Gly Val Pro Gly
                245                 250                 255

Val Gly Val Pro Gly Val Gly Val Pro Gly Val Gly Val Pro Gly Gly
            260                 265                 270

Gly Val Pro Gly Ala Gly Val Pro Gly Gly Gly Val Pro Gly Val Gly
        275                 280                 285

Val Pro Gly Val Gly Val Pro Gly Gly Gly Val Pro Gly Ala Gly Val
    290                 295                 300

Pro Gly Val Gly Val Pro Gly Val Gly Val Pro Gly Val Gly Val Pro
305                 310                 315                 320

Gly Gly Gly Val Pro Gly Ala Gly Val Pro Gly Gly Gly Val Pro Gly
                325                 330                 335

Val Gly Val Pro Gly Val Gly Val Pro Gly Gly Gly Val Pro Gly Ala
            340                 345                 350

Gly Val Pro Gly Val Gly Val Pro Gly Val Gly Val Pro Gly Val Gly
        355                 360                 365
```

-continued

```
Val Pro Gly Gly Gly Val Pro Gly Ala Gly Val Pro Gly Gly Gly Val
    370                 375                 380

Pro Gly Val Gly Val Pro Gly Val Gly Val Pro Gly Gly Gly Val Pro
385                 390                 395                 400

Gly Ala Gly Val Pro Gly Val Gly Val Pro Gly Val Gly Val Pro Gly
                405                 410                 415

Val Gly Val Pro Gly Gly Gly Val Pro Gly Ala Gly Val Pro Gly Gly
            420                 425                 430

Gly Val Pro Gly Val Gly Val Pro Gly Val Gly Val Pro Gly Gly Gly
        435                 440                 445

Val Pro Gly Ala Gly Val Pro Gly Val Gly Val Pro Gly Val Gly Val
    450                 455                 460

Pro Gly Val Gly Val Pro Gly Gly Gly Val Pro Gly Ala Gly Val Pro
465                 470                 475                 480

Gly Gly Gly Val Pro Gly Val Gly Val Pro Gly Val Gly Val Pro Gly
                485                 490                 495

Gly Gly Val Pro Gly Ala Gly Val Pro Gly Val Gly Val Pro Gly Val
            500                 505                 510

Gly Val Pro Gly Val Gly Val Pro Gly Gly Gly Val Pro Gly Ala Gly
        515                 520                 525

Val Pro Gly Gly Gly Val Pro Gly Val Gly Val Pro Gly Val Gly Val
    530                 535                 540

Pro Gly Gly Gly Val Pro Gly Ala Gly Val Pro Gly Val Gly Val Pro
545                 550                 555                 560

Gly Val Gly Val Pro Gly Val Gly Val Pro Gly Gly Gly Val Pro Gly
                565                 570                 575

Ala Gly Val Pro Gly Gly Gly Val Pro Gly Val Gly Val Pro Gly Val
            580                 585                 590

Gly Val Pro Gly Gly Gly Val Pro Gly Ala Gly Val Pro Gly Val Gly
        595                 600                 605

Val Pro Gly Val Gly Val Pro Gly Val Gly Val Pro Gly Gly Gly Val
    610                 615                 620

Pro Gly Ala Gly Val Pro Gly Gly Gly Val Pro Gly Trp Pro
625                 630                 635


<210> SEQ ID NO 29
<211> LENGTH: 488
<212> TYPE: PRT
<213> ORGANISM: Artificial Sequence
<220> FEATURE:
<223> OTHER INFORMATION: Synthetic construct

<400> SEQUENCE: 29

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95
```

-continued

```
Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Cys
                165                 170                 175

Cys Gly Gln Gly Gly Met Gly Gly Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285

Val Pro Gly Val Gly Val Pro Gly Val Gly Val Pro Gly Val Gly Val
    290                 295                 300

Pro Gly Val Gly Val Pro Gly Val Gly Val Pro Gly Val Gly Val Pro
305                 310                 315                 320

Gly Val Gly Val Pro Gly Val Gly Val Pro Gly Val Gly Val Pro Gly
                325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
        355                 360                 365

Val Pro Gly Val Gly Val Pro Gly Val Gly Val Pro Gly Val Gly Val
    370                 375                 380

Pro Gly Val Gly Val Pro Gly Val Gly Val Pro Gly Val Gly Val Pro
385                 390                 395                 400

Gly Val Gly Val Pro Gly Val Gly Val Pro Gly Val Gly Val Pro Gly
                405                 410                 415

Val Gly Val Pro Gly Val Gly Val Pro Gly Val Gly Val Pro Gly Val
            420                 425                 430

Gly Val Pro Gly Val Gly Val Pro Gly Val Gly Val Pro Gly Val Gly
        435                 440                 445

Val Pro Gly Val Gly Val Pro Gly Val Gly Val Pro Gly Val Gly Val
    450                 455                 460

Pro Gly Val Gly Val Pro Gly Val Gly Val Pro Gly Val Gly Val Pro
465                 470                 475                 480

Gly Val Gly Val Pro Gly Trp Pro
                485
```

<210> SEQ ID NO 30
<211> LENGTH: 634
<212> TYPE: PRT

-continued

<213> ORGANISM: Artificial Sequence
<220> FEATURE:
<223> OTHER INFORMATION: Synthetic construct

<400> SEQUENCE: 30

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Met
                165                 170                 175

Gly Gly Pro Gly Val Gly Val Pro Gly Val Gly Val Pro Gly Gly Gly
            180                 185                 190

Val Pro Gly Ala Gly Val Pro Gly Val Gly Val Pro Gly Val Gly Val
        195                 200                 205

Pro Gly Val Gly Val Pro Gly Gly Gly Val Pro Gly Ala Gly Val Pro
    210                 215                 220

Gly Gly Gly Val Pro Gly Val Gly Val Pro Gly Val Gly Val Pro Gly
225                 230                 235                 240

Gly Gly Val Pro Gly Ala Gly Val Pro Gly Val Gly Val Pro Gly Val
                245                 250                 255

Gly Val Pro Gly Val Gly Val Pro Gly Gly Gly Val Pro Gly Ala Gly
            260                 265                 270

Val Pro Gly Gly Gly Val Pro Gly Val Gly Val Pro Gly Val Gly Val
        275                 280                 285

Pro Gly Gly Gly Val Pro Gly Ala Gly Val Pro Gly Val Gly Val Pro
    290                 295                 300

Gly Val Gly Val Pro Gly Val Gly Val Pro Gly Gly Gly Val Pro Gly
305                 310                 315                 320

Ala Gly Val Pro Gly Gly Gly Val Pro Gly Val Gly Val Pro Gly Val
                325                 330                 335

Gly Val Pro Gly Gly Gly Val Pro Gly Ala Gly Val Pro Gly Val Gly
            340                 345                 350

Val Pro Gly Val Gly Val Pro Gly Val Gly Val Pro Gly Gly Gly Val
        355                 360                 365

Pro Gly Ala Gly Val Pro Gly Gly Gly Val Pro Gly Val Gly Val Pro
    370                 375                 380

Gly Val Gly Val Pro Gly Gly Gly Val Pro Gly Ala Gly Val Pro Gly
```

-continued

```
385                 390                 395                 400

Val Gly Val Pro Gly Val Gly Val Pro Gly Val Gly Val Pro Gly Gly
                405                 410                 415

Gly Val Pro Gly Ala Gly Val Pro Gly Gly Gly Val Pro Gly Val Gly
            420                 425                 430

Val Pro Gly Val Gly Val Pro Gly Gly Gly Val Pro Gly Ala Gly Val
        435                 440                 445

Pro Gly Val Gly Val Pro Gly Val Gly Val Pro Gly Val Gly Val Pro
    450                 455                 460

Gly Gly Gly Val Pro Gly Ala Gly Val Pro Gly Gly Gly Val Pro Gly
465                 470                 475                 480

Val Gly Val Pro Gly Val Gly Val Pro Gly Gly Gly Val Pro Gly Ala
                485                 490                 495

Gly Val Pro Gly Val Gly Val Pro Gly Val Gly Val Pro Gly Val Gly
            500                 505                 510

Val Pro Gly Gly Gly Val Pro Gly Ala Gly Val Pro Gly Gly Gly Val
        515                 520                 525

Pro Gly Val Gly Val Pro Gly Val Gly Val Pro Gly Gly Gly Val Pro
    530                 535                 540

Gly Ala Gly Val Pro Gly Val Gly Val Pro Gly Val Gly Val Pro Gly
545                 550                 555                 560

Val Gly Val Pro Gly Gly Gly Val Pro Gly Ala Gly Val Pro Gly Gly
                565                 570                 575

Gly Val Pro Gly Val Gly Val Pro Gly Val Gly Val Pro Gly Gly Gly
            580                 585                 590

Val Pro Gly Ala Gly Val Pro Gly Val Gly Val Pro Gly Val Gly Val
        595                 600                 605

Pro Gly Val Gly Val Pro Gly Gly Gly Val Pro Gly Ala Gly Val Pro
    610                 615                 620

Gly Gly Gly Val Pro Gly Trp Pro Cys Cys
625                 630


<210> SEQ ID NO 31
<211> LENGTH: 484
<212> TYPE: PRT
<213> ORGANISM: Artificial Sequence
<220> FEATURE:
<223> OTHER INFORMATION: Synthetic construct

<400> SEQUENCE: 31

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
```

-continued

```
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Met
                165                 170                 175

Gly Gly Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Val Pro Gly Val Gly Val Pro Gly
225                 230                 235                 240

Val Gly Val Pro Gly Val Gly Val Pro Gly Val Gly Val Pro Gly Val
                245                 250                 255

Gly Val Pro Gly Val Gly Val Pro Gly Val Gly Val Pro Gly Val Gly
            260                 265                 270

Val Pro Gly Val Gly Val Pro Gly Val Gly Val Pro Gly Val Gly Val
        275                 280                 285

Pro Gly Val Gly Val Pro Gly Val Gly Val Pro Gly Val Gly Val Pro
    290                 295                 300

Gly Val Gly Val Pro Gly Val Gly Val Pro Gly Val Gly Val Pro Gly
305                 310                 315                 320

Val Gly Val Pro Gly Val Gly Val Pro Gly Val Gly Val Pro Gly Val
                325                 330                 335

Gly Val Pro Gly Val Gly Val Pro Gly Val Gly Val Pro Gly Val Gly
            340                 345                 350

Val Pro Gly Val Gly Val Pro Gly Val Gly Val Pro Gly Val Gly Val
        355                 360                 365

Pro Gly Val Gly Val Pro Gly Val Gly Val Pro Gly Val Gly Val Pro
    370                 375                 380

Gly Val Gly Val Pro Gly Val Gly Val Pro Gly Val Gly Val Pro Gly
385                 390                 395                 400

Val Gly Val Pro Gly Val Gly Val Pro Gly Val Gly Val Pro Gly Val
                405                 410                 415

Gly Val Pro Gly Val Gly Val Pro Gly Val Gly Val Pro Gly Val Gly
            420                 425                 430

Val Pro Gly Val Gly Val Pro Gly Val Gly Val Pro Gly Val Gly Val
        435                 440                 445

Pro Gly Val Gly Val Pro Gly Val Gly Val Pro Gly Val Gly Val Pro
    450                 455                 460

Gly Val Gly Val Pro Gly Val Gly Val Pro Gly Val Gly Val Pro Gly
465                 470                 475                 480

Trp Pro Cys Cys
```

```
<210> SEQ ID NO 32
<211> LENGTH: 632
<212> TYPE: PRT
<213> ORGANISM: Artificial Sequence
<220> FEATURE:
<223> OTHER INFORMATION: Synthetic construct

<400> SEQUENCE: 32
```

-continued

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Met
                165                 170                 175

Gly Gly Pro Gly Val Gly Val Pro Gly Val Gly Val Pro Gly Gly Gly
            180                 185                 190

Val Pro Gly Ala Gly Val Pro Gly Val Gly Val Pro Gly Val Gly Val
        195                 200                 205

Pro Gly Val Gly Val Pro Gly Gly Gly Val Pro Gly Ala Gly Val Pro
    210                 215                 220

Gly Gly Gly Val Pro Gly Val Gly Val Pro Gly Val Gly Val Pro Gly
225                 230                 235                 240

Gly Gly Val Pro Gly Ala Gly Val Pro Gly Val Gly Val Pro Gly Val
                245                 250                 255

Gly Val Pro Gly Val Gly Val Pro Gly Gly Gly Val Pro Gly Ala Gly
            260                 265                 270

Val Pro Gly Gly Gly Val Pro Gly Val Gly Val Pro Gly Val Gly Val
        275                 280                 285

Pro Gly Gly Gly Val Pro Gly Ala Gly Val Pro Gly Val Gly Val Pro
    290                 295                 300

Gly Val Gly Val Pro Gly Val Gly Val Pro Gly Gly Gly Val Pro Gly
305                 310                 315                 320

Ala Gly Val Pro Gly Gly Gly Val Pro Gly Val Gly Val Pro Gly Val
                325                 330                 335

Gly Val Pro Gly Gly Gly Val Pro Gly Ala Gly Val Pro Gly Val Gly
            340                 345                 350

Val Pro Gly Val Gly Val Pro Gly Val Gly Val Pro Gly Gly Gly Val
        355                 360                 365

Pro Gly Ala Gly Val Pro Gly Gly Gly Val Pro Gly Val Gly Val Pro
    370                 375                 380

Gly Val Gly Val Pro Gly Gly Gly Val Pro Gly Ala Gly Val Pro Gly
385                 390                 395                 400

Val Gly Val Pro Gly Val Gly Val Pro Gly Val Gly Val Pro Gly Gly
                405                 410                 415
```

-continued

```
Gly Val Pro Gly Ala Gly Val Pro Gly Gly Gly Val Pro Gly Val Gly
            420                 425                 430

Val Pro Gly Val Gly Val Pro Gly Gly Gly Val Pro Gly Ala Gly Val
        435                 440                 445

Pro Gly Val Gly Val Pro Gly Val Gly Val Pro Gly Val Gly Val Pro
    450                 455                 460

Gly Gly Gly Val Pro Gly Ala Gly Val Pro Gly Gly Gly Val Pro Gly
465                 470                 475                 480

Val Gly Val Pro Gly Val Gly Val Pro Gly Gly Gly Val Pro Gly Ala
                485                 490                 495

Gly Val Pro Gly Val Gly Val Pro Gly Val Gly Val Pro Gly Val Gly
            500                 505                 510

Val Pro Gly Gly Gly Val Pro Gly Ala Gly Val Pro Gly Gly Gly Val
        515                 520                 525

Pro Gly Val Gly Val Pro Gly Val Gly Val Pro Gly Gly Gly Val Pro
    530                 535                 540

Gly Ala Gly Val Pro Gly Val Gly Val Pro Gly Val Gly Val Pro Gly
545                 550                 555                 560

Val Gly Val Pro Gly Gly Gly Val Pro Gly Ala Gly Val Pro Gly Gly
                565                 570                 575

Gly Val Pro Gly Val Gly Val Pro Gly Val Gly Val Pro Gly Gly Gly
            580                 585                 590

Val Pro Gly Ala Gly Val Pro Gly Val Gly Val Pro Gly Val Gly Val
        595                 600                 605

Pro Gly Val Gly Val Pro Gly Gly Gly Val Pro Gly Ala Gly Val Pro
    610                 615                 620

Gly Gly Gly Val Pro Gly Trp Pro
625                 630
```

<210> SEQ ID NO 33
<211> LENGTH: 482
<212> TYPE: PRT
<213> ORGANISM: Artificial Sequence
<220> FEATURE:
<223> OTHER INFORMATION: Synthetic construct

<400> SEQUENCE: 33

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140
```

-continued

```
Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln Gly Gly Met
                165                 170                 175

Gly Gly Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Val Pro Gly Val Gly Val Pro Gly
225                 230                 235                 240

Val Gly Val Pro Gly Val Gly Val Pro Gly Val Gly Val Pro Gly Val
                245                 250                 255

Gly Val Pro Gly Val Gly Val Pro Gly Val Gly Val Pro Gly Val Gly
            260                 265                 270

Val Pro Gly Val Gly Val Pro Gly Val Gly Val Pro Gly Val Gly Val
        275                 280                 285

Pro Gly Val Gly Val Pro Gly Val Gly Val Pro Gly Val Gly Val Pro
    290                 295                 300

Gly Val Gly Val Pro Gly Val Gly Val Pro Gly Val Gly Val Pro Gly
305                 310                 315                 320

Val Gly Val Pro Gly Val Gly Val Pro Gly Val Gly Val Pro Gly Val
                325                 330                 335

Gly Val Pro Gly Val Gly Val Pro Gly Val Gly Val Pro Gly Val Gly
            340                 345                 350

Val Pro Gly Val Gly Val Pro Gly Val Gly Val Pro Gly Val Gly Val
        355                 360                 365

Pro Gly Val Gly Val Pro Gly Val Gly Val Pro Gly Val Gly Val Pro
    370                 375                 380

Gly Val Gly Val Pro Gly Val Gly Val Pro Gly Val Gly Val Pro Gly
385                 390                 395                 400

Val Gly Val Pro Gly Val Gly Val Pro Gly Val Gly Val Pro Gly Val
                405                 410                 415

Gly Val Pro Gly Val Gly Val Pro Gly Val Gly Val Pro Gly Val Gly
            420                 425                 430

Val Pro Gly Val Gly Val Pro Gly Val Gly Val Pro Gly Val Gly Val
        435                 440                 445

Pro Gly Val Gly Val Pro Gly Val Gly Val Pro Gly Val Gly Val Pro
    450                 455                 460

Gly Val Gly Val Pro Gly Val Gly Val Pro Gly Val Gly Val Pro Gly
465                 470                 475                 480

Trp Pro
```

<210> SEQ ID NO 34
<211> LENGTH: 5123
<212> TYPE: DNA
<213> ORGANISM: Artificial Sequence
<220> FEATURE:
<223> OTHER INFORMATION: Synthetic construct

<400> SEQUENCE: 34

```
ttcttgaaga cgaaagggcc tcgtgatacg cctattttta taggttaatg tcatgataat      60

aatggtttct tagacgtcag gtggcacttt tcggggaaat gtgcgcggaa cccctatttg     120
```

-continued

```
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttttcctg tttggtcact gatgcctccg   2460
tgtaaggggg atttctgttc atgggggtaa tgataccgat gaaacgagag aggatgctca   2520
```

-continued

```
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgt gctgccccat gggtgggccg   3060
ggcgtgggtg ttccgggcgt gggtgttccg ggtggcggtg tgccgggcgc aggtgttcct   3120
ggtgtaggtg tgccgggtgt tggtgtgccg ggtgttggtg taccaggtgg cggtgttccg   3180
ggtgcaggcg ttccgggtgg cggtgtgccg ggcgtgggtg ttccgggcgt gggtgttccg   3240
ggtggcggtg tgccgggcgc aggtgttcct ggtgtaggtg tgccgggtgt tggtgtgccg   3300
ggtgttggtg taccaggtgg cggtgttccg ggtgcaggcg ttccgggtgg cggtgtgccg   3360
ggcgtgggtg ttccgggcgt gggtgttccg ggtggcggtg tgccgggcgc aggtgttcct   3420
ggtgtaggtg tgccgggtgt tggtgtgccg ggtgttggtg taccaggtgg cggtgttccg   3480
ggtgcaggcg ttccgggtgg cggtgtgccg ggcgtgggtg ttccgggcgt gggtgttccg   3540
ggtggcggtg tgccgggcgc aggtgttcct ggtgtaggtg tgccgggtgt tggtgtgccg   3600
ggtgttggtg taccaggtgg cggtgttccg ggtgcaggcg ttccgggtgg cggtgtgccg   3660
ggcgtgggtg ttccgggcgt gggtgttccg ggtggcggtg tgccgggcgc aggtgttcct   3720
ggtgtaggtg tgccgggtgt tggtgtgccg ggtgttggtg taccaggtgg cggtgttccg   3780
ggtgcaggcg ttccgggtgg cggtgtgccg ggcgtgggtg ttccgggcgt gggtgttccg   3840
ggtggcggtg tgccgggcgc aggtgttcct ggtgtaggtg tgccgggtgt tggtgtgccg   3900
ggtgttggtg taccaggtgg cggtgttccg ggtgcaggcg ttccgggtgg cggtgtgccg   3960
ggcgtgggtg ttccgggcgt gggtgttccg ggtggcggtg tgccgggcgc aggtgttcct   4020
ggtgtaggtg tgccgggtgt tggtgtgccg ggtgttggtg taccaggtgg cggtgttccg   4080
ggtgcaggcg ttccgggtgg cggtgtgccg ggcgtgggtg ttccgggcgt gggtgttccg   4140
ggtggcggtg tgccgggcgc aggtgttcct ggtgtaggtg tgccgggtgt tggtgtgccg   4200
ggtgttggtg taccaggtgg cggtgttccg ggtgcaggcg ttccgggtgg cggtgtgccg   4260
ggcgtgggtg ttccgggcgt gggtgttccg ggtggcggtg tgccgggcgc aggtgttcct   4320
ggtgtaggtg tgccgggtgt tggtgtgccg ggtgttggtg taccaggtgg cggtgttccg   4380
ggtgcaggcg ttccgggtgg cggtgtgccg ggctggccga gcagcggtga ttacgatatc   4440
ccaacgaccg aaaacctgta ttttcagggc gcccatatgt gtgatctgcc tcaaacccac   4500
agcctgggta gcaggaggac cttgatgctc ctggcacaga tgaggagaat ctctcttttc   4560
tcctgcttga aggacagaca tgactttgga tttccccagg aggagtttgg caaccagttc   4620
caaaaggctg aaaccatccc tgtcctccat gagatgatcc agcagatctt caatctcttc   4680
agcacaaagg actcatctgc tgcttgggat gagaccctcc tagacaaatt ctacactgaa   4740
ctctaccagc agctgaatga cctggaagcc tgtgtgatac agggggtggg ggtgacagag   4800
actcccctga tgaaggagga ctccattctg gctgtgagga aatacttcca aagaatcact   4860
```

-continued

```
ctctatctga aagagaagaa atacagccct tgtgcctggg aggttgtcag agcagaaatc   4920

atgagatctt tttctttgtc aacaaacttg caagaaagtt taagaagtaa ggaataactc   4980

gagcagatcc ggctgctaac aaagcccgaa aggaagctga gttggctgct gccaccgctg   5040

agcaataact agcataaccc cttggggcct ctaaacgggt cttgaggggt tttttgctga   5100

aaggaggaac tatatccgga taa                                           5123
```

<210> SEQ ID NO 35
<211> LENGTH: 4673
<212> TYPE: DNA
<213> ORGANISM: Artificial Sequence
<220> FEATURE:
<223> OTHER INFORMATION: Synthetic construct

<400> SEQUENCE: 35

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840

ggataaagtt gcaggaccac ttctgcgctc ggcccttccg gctggctggt ttattgctga    900

taaatctgga gccggtgagc gtgggtctcg cggtatcatt gcagcactgg ggccagatgg    960

taagccctcc cgtatcgtag ttatctacac gacggggagt caggcaacta tggatgaacg   1020

aaatagacag atcgctgaga taggtgcctc actgattaag cattggtaac tgtcagacca   1080

agtttactca tatatacttt agattgattt aaaacttcat ttttaattta aaaggatcta   1140

ggtgaagatc ctttttgata atctcatgac caaaatccct taacgtgagt tttcgttcca   1200

ctgagcgtca gaccccgtag aaaagatcaa aggatcttct tgagatcctt tttttctgcg   1260

cgtaatctgc tgcttgcaaa caaaaaaacc accgctacca gcggtggttt gtttgccgga   1320

tcaagagcta ccaactcttt ttccgaaggt aactggcttc agcagagcgc agataccaaa   1380

tactgtcctt ctagtgtagc cgtagttagg ccaccacttc aagaactctg tagcaccgcc   1440

tacatacctc gctctgctaa tcctgttacc agtggctgct gccagtggcg ataagtcgtg   1500

tcttaccggg ttggactcaa gacgatagtt accggataag gcgcagcggt cgggctgaac   1560

ggggggttcg tgcacacagc ccagcttgga gcgaacgacc tacaccgaac tgagatacct   1620

acagcgtgag ctatgagaaa gcgccacgct tcccgaaggg agaaaggcgg acaggtatcc   1680

ggtaagcggc agggtcggaa caggagagcg cacgagggag cttccagggg gaaacgcctg   1740

gtatctttat agtcctgtcg ggtttcgcca cctctgactt gagcgtcgat ttttgtgatg   1800
```

-continued

```
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgt gctgccccat gggtgggccg   3060
ggcgtgggtg ttccgggcgt aggtgtccca ggtgtgggcg taccgggcgt tggtgttcct   3120
ggtgtcggcg tgccgggcgt gggtgttccg ggcgtaggtg tcccaggtgt gggcgtaccg   3180
ggcgttggtg ttcctggtgt cggcgtgccg ggcgtgggtg ttccgggcgt aggtgtccca   3240
ggtgtgggcg taccgggcgt tggtgttcct ggtgtcggcg tgccgggcgt gggtgttccg   3300
ggcgtaggtg tcccaggtgt gggcgtaccg ggcgttggtg ttcctggtgt cggcgtgccg   3360
ggcgtgggtg ttccgggcgt aggtgtccca ggtgtgggcg taccgggcgt tggtgttcct   3420
ggtgtcggcg tgccgggcgt gggtgttccg ggcgtaggtg tcccaggtgt gggcgtaccg   3480
ggcgttggtg ttcctggtgt cggcgtgccg ggcgtgggtg ttccgggcgt aggtgtccca   3540
ggtgtgggcg taccgggcgt tggtgttcct ggtgtcggcg tgccgggcgt gggtgttccg   3600
ggcgtaggtg tcccaggtgt gggcgtaccg ggcgttggtg ttcctggtgt cggcgtgccg   3660
ggcgtgggtg ttccgggcgt aggtgtccca ggtgtgggcg taccgggcgt tggtgttcct   3720
ggtgtcggcg tgccgggcgt gggtgttccg ggcgtaggtg tcccaggtgt gggcgtaccg   3780
ggcgttggtg ttcctggtgt cggcgtgccg ggcgtgggtg ttccgggcgt aggtgtccca   3840
ggtgtgggcg taccgggcgt tggtgttcct ggtgtcggcg tgccgggcgt gggtgttccg   3900
ggcgtaggtg tcccaggtgt gggcgtaccg ggcgttggtg ttcctggtgt cggcgtgccg   3960
ggctggccga gcagcggtga ttacgatatc ccaacgaccg aaaacctgta ttttcagggc   4020
gcccatatgt gtgatctgcc tcaaacccac agcctgggta gcaggaggac cttgatgctc   4080
ctggcacaga tgaggagaat ctctcttttc tcctgcttga aggacagaca tgactttgga   4140
```

-continued

```
tttccccagg aggagtttgg caaccagttc caaaaggctg aaaccatccc tgtcctccat   4200

gagatgatcc agcagatctt caatctcttc agcacaaagg actcatctgc tgcttgggat   4260

gagaccctcc tagacaaatt ctacactgaa ctctaccagc agctgaatga cctggaagcc   4320

tgtgtgatac agggggtggg ggtgacagag actcccctga tgaaggagga ctccattctg   4380

gctgtgagga aatacttcca aagaatcact ctctatctga aagagaagaa atacagccct   4440

tgtgcctggg aggttgtcag agcagaaatc atgagatctt tttctttgtc aacaaacttg   4500

caagaaagtt taagaagtaa ggaataactc gagcagatcc ggctgctaac aaagcccgaa   4560

aggaagctga gttggctgct gccaccgctg agcaataact agcataaccc cttggggcct   4620

ctaaacgggt cttgaggggt tttttgctga aaggaggaac tatatccgga taa          4673
```

<210> SEQ ID NO 36
<211> LENGTH: 5111
<212> TYPE: DNA
<213> ORGANISM: Artificial Sequence
<220> FEATURE:
<223> OTHER INFORMATION: Synthetic construct

<400> SEQUENCE: 36

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840

ggataaagtt gcaggaccac ttctgcgctc ggcccttccg gctggctggt ttattgctga    900

taaatctgga gccggtgagc gtgggtctcg cggtatcatt gcagcactgg ggccagatgg    960

taagccctcc cgtatcgtag ttatctacac gacggggagt caggcaacta tggatgaacg   1020

aaatagacag atcgctgaga taggtgcctc actgattaag cattggtaac tgtcagacca   1080

agtttactca tatatacttt agattgattt aaaacttcat ttttaattta aaaggatcta   1140

ggtgaagatc ctttttgata atctcatgac caaaatccct taacgtgagt tttcgttcca   1200

ctgagcgtca gaccccgtag aaaagatcaa aggatcttct tgagatcctt tttttctgcg   1260

cgtaatctgc tgcttgcaaa caaaaaaacc accgctacca gcggtggttt gtttgccgga   1320

tcaagagcta ccaactcttt ttccgaaggt aactggcttc agcagagcgc agataccaaa   1380

tactgtcctt ctagtgtagc cgtagttagg ccaccacttc aagaactctg tagcaccgcc   1440

tacatacctc gctctgctaa tcctgttacc agtggctgct gccagtggcg ataagtcgtg   1500

tcttaccggg ttggactcaa gacgatagtt accggataag gcgcagcggt cgggctgaac   1560
```

-continued

```
gggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg    2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgg gtgggccggg cgtgggtgtt   3060
ccgggcgtgg gtgttccggg tggcggtgtg ccgggcgcag gtgttcctgg tgtaggtgtg   3120
ccgggtgttg gtgtgccggg tgttggtgta ccaggtggcg gtgttccggg tgcaggcgtt   3180
ccgggtggcg gtgtgccggg cgtgggtgtt ccgggcgtgg gtgttccggg tggcggtgtg   3240
ccgggcgcag gtgttcctgg tgtaggtgtg ccgggtgttg gtgtgccggg tgttggtgta   3300
ccaggtggcg gtgttccggg tgcaggcgtt ccgggtggcg gtgtgccggg cgtgggtgtt   3360
ccgggcgtgg gtgttccggg tggcggtgtg ccgggcgcag gtgttcctgg tgtaggtgtg   3420
ccgggtgttg gtgtgccggg tgttggtgta ccaggtggcg gtgttccggg tgcaggcgtt   3480
ccgggtggcg gtgtgccggg cgtgggtgtt ccgggcgtgg gtgttccggg tggcggtgtg   3540
ccgggcgcag gtgttcctgg tgtaggtgtg ccgggtgttg gtgtgccggg tgttggtgta   3600
ccaggtggcg gtgttccggg tgcaggcgtt ccgggtggcg gtgtgccggg cgtgggtgtt   3660
ccgggcgtgg gtgttccggg tggcggtgtg ccgggcgcag gtgttcctgg tgtaggtgtg   3720
ccgggtgttg gtgtgccggg tgttggtgta ccaggtggcg gtgttccggg tgcaggcgtt   3780
ccgggtggcg gtgtgccggg cgtgggtgtt ccgggcgtgg gtgttccggg tggcggtgtg   3840
ccgggcgcag gtgttcctgg tgtaggtgtg ccgggtgttg gtgtgccggg tgttggtgta   3900
```

-continued

```
ccaggtggcg gtgttccggg tgcaggcgtt ccgggtggcg gtgtgccggg cgtgggtgtt   3960

ccgggcgtgg gtgttccggg tggcggtgtg ccgggcgcag gtgttcctgg tgtaggtgtg   4020

ccgggtgttg gtgtgccggg tgttggtgta ccaggtggcg gtgttccggg tgcaggcgtt   4080

ccgggtggcg gtgtgccggg cgtgggtgtt ccgggcgtgg gtgttccggg tggcggtgtg   4140

ccgggcgcag gtgttcctgg tgtaggtgtg ccgggtgttg gtgtgccggg tgttggtgta   4200

ccaggtggcg gtgttccggg tgcaggcgtt ccgggtggcg gtgtgccggg cgtgggtgtt   4260

ccgggcgtgg gtgttccggg tggcggtgtg ccgggcgcag gtgttcctgg tgtaggtgtg   4320

ccgggtgttg gtgtgccggg tgttggtgta ccaggtggcg gtgttccggg tgcaggcgtt   4380

ccgggtggcg gtgtgccggg ctggccgtgc tgcagcagcg gtgatatccc aacgaccgaa   4440

aacctgtatt ttcagggcgc ccatatgtgt gatctgcctc aaacccacag cctgggtagc   4500

aggaggacct tgatgctcct ggcacagatg aggagaatct ctcttttctc ctgcttgaag   4560

gacagacatg actttggatt tccccaggag gagtttggca accagttcca aaaggctgaa   4620

accatccctg tcctccatga gatgatccag cagatcttca atctcttcag cacaaaggac   4680

tcatctgctg cttgggatga gaccctccta gacaaattct acactgaact ctaccagcag   4740

ctgaatgacc tggaagcctg tgtgatacag ggggtggggg tgacagagac tcccctgatg   4800

aaggaggact ccattctggc tgtgaggaaa tacttccaaa gaatcactct ctatctgaaa   4860

gagaagaaat acagcccttg tgcctgggag gttgtcagag cagaaatcat gagatctttt   4920

tctttgtcaa caaacttgca agaaagttta agaagtaagg aataactcga gcagatccgg   4980

ctgctaacaa agcccgaaag gaagctgagt tggctgctgc caccgctgag caataactag   5040

cataacccct tggggcctct aaacgggtct tgaggggttt tttgctgaaa ggaggaacta   5100

tatccggata a                                                         5111
```

<210> SEQ ID NO 37
<211> LENGTH: 4661
<212> TYPE: DNA
<213> ORGANISM: Artificial Sequence
<220> FEATURE:
<223> OTHER INFORMATION: Synthetic construct

<400> SEQUENCE: 37

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840
```

-continued

```
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgg gtgggccggg cgtgggtgtt   3060
ccgggcgtag gtgtcccagg tgtgggcgta ccgggcgttg gtgttcctgg tgtcggcgtg   3120
ccgggcgtgg gtgttccggg cgtaggtgtc ccaggtgtgg gcgtaccggg cgttggtgtt   3180
```

-continued

```
cctggtgtcg gcgtgccggg cgtgggtgtt ccgggcgtag gtgtcccagg tgtgggcgta   3240
ccgggcgttg gtgttcctgg tgtcggcgtg ccgggcgtgg gtgttccggg cgtaggtgtc   3300
ccaggtgtgg gcgtaccggg cgttggtgtt cctggtgtcg gcgtgccggg cgtgggtgtt   3360
ccgggcgtag gtgtcccagg tgtgggcgta ccgggcgttg gtgttcctgg tgtcggcgtg   3420
ccgggcgtgg gtgttccggg cgtaggtgtc ccaggtgtgg gcgtaccggg cgttggtgtt   3480
cctggtgtcg gcgtgccggg cgtgggtgtt ccgggcgtag gtgtcccagg tgtgggcgta   3540
ccgggcgttg gtgttcctgg tgtcggcgtg ccgggcgtgg gtgttccggg cgtaggtgtc   3600
ccaggtgtgg gcgtaccggg cgttggtgtt cctggtgtcg gcgtgccggg cgtgggtgtt   3660
ccgggcgtag gtgtcccagg tgtgggcgta ccgggcgttg gtgttcctgg tgtcggcgtg   3720
ccgggcgtgg gtgttccggg cgtaggtgtc ccaggtgtgg gcgtaccggg cgttggtgtt   3780
cctggtgtcg gcgtgccggg cgtgggtgtt ccgggcgtag gtgtcccagg tgtgggcgta   3840
ccgggcgttg gtgttcctgg tgtcggcgtg ccgggcgtgg gtgttccggg cgtaggtgtc   3900
ccaggtgtgg gcgtaccggg cgttggtgtt cctggtgtcg gcgtgccggg ctggccgtgc   3960
tgcagcagcg gtgatatccc aacgaccgaa aacctgtatt ttcagggcgc ccatatgtgt   4020
gatctgcctc aaacccacag cctgggtagc aggaggacct tgatgctcct ggcacagatg   4080
aggagaatct ctcttttctc ctgcttgaag gacagacatg actttggatt tccccaggag   4140
gagtttggca accagttcca aaaggctgaa accatccctg tcctccatga gatgatccag   4200
cagatcttca atctcttcag cacaaaggac tcatctgctg cttgggatga gaccctccta   4260
gacaaattct acactgaact ctaccagcag ctgaatgacc tggaagcctg tgtgatacag   4320
ggggtggggg tgacagagac tcccctgatg aaggaggact ccattctggc tgtgaggaaa   4380
tacttccaaa gaatcactct ctatctgaaa gagaagaaat acagcccttg tgcctgggag   4440
gttgtcagag cagaaatcat gagatctttt tctttgtcaa caaacttgca agaaagttta   4500
agaagtaagg aataactcga gcagatccgg ctgctaacaa agcccgaaag gaagctgagt   4560
tggctgctgc caccgctgag caataactag cataacccct tggggcctct aaacgggtct   4620
tgaggggttt tttgctgaaa ggaggaacta tatccggata a                        4661
```

<210> SEQ ID NO 38
<211> LENGTH: 5111
<212> TYPE: DNA
<213> ORGANISM: Artificial Sequence
<220> FEATURE:
<223> OTHER INFORMATION: Synthetic construct

<400> SEQUENCE: 38

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
```

-continued

```
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
```

-continued

```
tctcgatccc gcgaaattaa tacgactcac tatagggaga ccacaacggt ttccctctag   3000

aaataatttt gtttaacttt aagaaggaga tataccatgg gtgggccggg cgtgggtgtt   3060

ccgggcgtgg gtgttccggg tggcggtgtg ccgggcgcag gtgttcctgg tgtaggtgtg   3120

ccgggtgttg gtgtgccggg tgttggtgta ccaggtggcg gtgttccggg tgcaggcgtt   3180

ccgggtggcg gtgtgccggg cgtgggtgtt ccgggcgtgg gtgttccggg tggcggtgtg   3240

ccgggcgcag gtgttcctgg tgtaggtgtg ccgggtgttg gtgtgccggg tgttggtgta   3300

ccaggtggcg gtgttccggg tgcaggcgtt ccgggtggcg gtgtgccggg cgtgggtgtt   3360

ccgggcgtgg gtgttccggg tggcggtgtg ccgggcgcag gtgttcctgg tgtaggtgtg   3420

ccgggtgttg gtgtgccggg tgttggtgta ccaggtggcg gtgttccggg tgcaggcgtt   3480

ccgggtggcg gtgtgccggg cgtgggtgtt ccgggcgtgg gtgttccggg tggcggtgtg   3540

ccgggcgcag gtgttcctgg tgtaggtgtg ccgggtgttg gtgtgccggg tgttggtgta   3600

ccaggtggcg gtgttccggg tgcaggcgtt ccgggtggcg gtgtgccggg cgtgggtgtt   3660

ccgggcgtgg gtgttccggg tggcggtgtg ccgggcgcag gtgttcctgg tgtaggtgtg   3720

ccgggtgttg gtgtgccggg tgttggtgta ccaggtggcg gtgttccggg tgcaggcgtt   3780

ccgggtggcg gtgtgccggg cgtgggtgtt ccgggcgtgg gtgttccggg tggcggtgtg   3840

ccgggcgcag gtgttcctgg tgtaggtgtg ccgggtgttg gtgtgccggg tgttggtgta   3900

ccaggtggcg gtgttccggg tgcaggcgtt ccgggtggcg gtgtgccggg cgtgggtgtt   3960

ccgggcgtgg gtgttccggg tggcggtgtg ccgggcgcag gtgttcctgg tgtaggtgtg   4020

ccgggtgttg gtgtgccggg tgttggtgta ccaggtggcg gtgttccggg tgcaggcgtt   4080

ccgggtggcg gtgtgccggg cgtgggtgtt ccgggcgtgg gtgttccggg tggcggtgtg   4140

ccgggcgcag gtgttcctgg tgtaggtgtg ccgggtgttg gtgtgccggg tgttggtgta   4200

ccaggtggcg gtgttccggg tgcaggcgtt ccgggtggcg gtgtgccggg cgtgggtgtt   4260

ccgggcgtgg gtgttccggg tggcggtgtg ccgggcgcag gtgttcctgg tgtaggtgtg   4320

ccgggtgttg gtgtgccggg tgttggtgta ccaggtggcg gtgttccggg tgcaggcgtt   4380

ccgggtggcg gtgtgccggg ctggccgagc agcggtgatt acgatatccc aacgaccgaa   4440

aacctgtatt ttcagggcgc ccatatgtgt gatctgcctc aaacccacag cctgggtagc   4500

aggaggacct tgatgctcct ggcacagatg aggagaatct ctcttttctc ctgcttgaag   4560

gacagacatg actttggatt tccccaggag gagtttggca accagttcca aaaggctgaa   4620

accatccctg tcctccatga gatgatccag cagatcttca atctcttcag cacaaaggac   4680

tcatctgctg cttgggatga gaccctccta gacaaattct acactgaact ctaccagcag   4740

ctgaatgacc tggaagcctg tgtgatacag ggggtggggg tgacagagac tcccctgatg   4800

aaggaggact ccattctggc tgtgaggaaa tacttccaaa gaatcactct ctatctgaaa   4860

gagaagaaat acagcccttg tgcctgggag gttgtcagag cagaaatcat gagatctttt   4920

tctttgtcaa caaacttgca agaaagttta agaagtaagg aataactcga gcagatccgg   4980

ctgctaacaa agcccgaaag gaagctgagt tggctgctgc caccgctgag caataactag   5040

cataacccct tggggcctct aaacgggtct tgaggggttt tttgctgaaa ggaggaacta   5100

tatccggata a                                                        5111
```

<210> SEQ ID NO 39
<211> LENGTH: 4661
<212> TYPE: DNA
<213> ORGANISM: Artificial Sequence -continued
<220> FEATURE:
<223> OTHER INFORMATION: Synthetic construct

<400> SEQUENCE: 39
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440
tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680
ggtaagcggc agggtcggaa caggagagcg cacgagggag cttccagggg gaaacgcctg 1740
gtatctttat agtcctgtcg ggtttcgcca cctctgactt gagcgtcgat ttttgtgatg 1800
ctcgtcaggg gggcggagcc tatggaaaaa cgccagcaac gcggcctttt tacggttcct 1860
ggccttttgc tggccttttg ctcacatgtt ctttcctgcg ttatcccctg attctgtgga 1920
taaccgtatt accgcctttg agtgagctga taccgctcgc cgcagccgaa cgaccgagcg 1980
cagcgagtca gtgagcgagg aagcggaaga gcgcctgatg cggtattttc tccttacgca 2040
tctgtgcggt atttcacacc gcatatatgg tgcactctca gtacaatctg ctctgatgcc 2100
gcatagttaa gccagtatac actccgctat cgctacgtga ctgggtcatg gctgcgcccc 2160
gacacccgcc aacacccgct gacgcgccct gacgggcttg tctgctcccg gcatccgctt 2220

-continued

```
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg    2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgg gtgggccggg cgtgggtgtt   3060
ccgggcgtag gtgtcccagg tgtgggcgta ccgggcgttg gtgttcctgg tgtcggcgtg   3120
ccgggcgtgg gtgttccggg cgtaggtgtc ccaggtgtgg gcgtaccggg cgttggtgtt   3180
cctggtgtcg gcgtgccggg cgtgggtgtt ccgggcgtag gtgtcccagg tgtgggcgta   3240
ccgggcgttg gtgttcctgg tgtcggcgtg ccgggcgtgg gtgttccggg cgtaggtgtc   3300
ccaggtgtgg gcgtaccggg cgttggtgtt cctggtgtcg gcgtgccggg cgtgggtgtt   3360
ccgggcgtag gtgtcccagg tgtgggcgta ccgggcgttg gtgttcctgg tgtcggcgtg   3420
ccgggcgtgg gtgttccggg cgtaggtgtc ccaggtgtgg gcgtaccggg cgttggtgtt   3480
cctggtgtcg gcgtgccggg cgtgggtgtt ccgggcgtag gtgtcccagg tgtgggcgta   3540
ccgggcgttg gtgttcctgg tgtcggcgtg ccgggcgtgg gtgttccggg cgtaggtgtc   3600
ccaggtgtgg gcgtaccggg cgttggtgtt cctggtgtcg gcgtgccggg cgtgggtgtt   3660
ccgggcgtag gtgtcccagg tgtgggcgta ccgggcgttg gtgttcctgg tgtcggcgtg   3720
ccgggcgtgg gtgttccggg cgtaggtgtc ccaggtgtgg gcgtaccggg cgttggtgtt   3780
cctggtgtcg gcgtgccggg cgtgggtgtt ccgggcgtag gtgtcccagg tgtgggcgta   3840
ccgggcgttg gtgttcctgg tgtcggcgtg ccgggcgtgg gtgttccggg cgtaggtgtc   3900
ccaggtgtgg gcgtaccggg cgttggtgtt cctggtgtcg gcgtgccggg ctggccgagc   3960
agcggtgatt acgatatccc aacgaccgaa aacctgtatt ttcagggcgc ccatatgtgt   4020
gatctgcctc aaacccacag cctgggtagc aggaggacct tgatgctcct ggcacagatg   4080
aggagaatct ctcttttctc ctgcttgaag gacagacatg actttggatt tccccaggag   4140
gagtttggca accagttcca aaaggctgaa accatccctg tcctccatga gatgatccag   4200
cagatcttca atctcttcag cacaaaggac tcatctgctg cttgggatga gaccctccta   4260
gacaaattct acactgaact ctaccagcag ctgaatgacc tggaagcctg tgtgatacag   4320
ggggtggggg tgacagagac tcccctgatg aaggaggact ccattctggc tgtgaggaaa   4380
tacttccaaa gaatcactct ctatctgaaa gagaagaaat acagcccttg tgcctgggag   4440
gttgtcagag cagaaatcat gagatctttt tctttgtcaa caaacttgca agaaagttta   4500
agaagtaagg aataactcga gcagatccgg ctgctaacaa agcccgaaag gaagctgagt   4560
tggctgctgc caccgctgag caataactag cataacccct tggggcctct aaacgggtct   4620
```

-continued tgaggggttt tttgctgaaa ggaggaacta tatccggata a 4661

<210> SEQ ID NO 40
<211> LENGTH: 5173
<212> TYPE: DNA
<213> ORGANISM: Artificial Sequence
<220> FEATURE:
<223> OTHER INFORMATION: Synthetic construct

<400> SEQUENCE: 40
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440
tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680
ggtaagcggc agggtcggaa caggagagcg cacgagggag cttccagggg gaaacgcctg 1740
gtatctttat agtcctgtcg ggtttcgcca cctctgactt gagcgtcgat ttttgtgatg 1800
ctcgtcaggg gggcggagcc tatggaaaaa cgccagcaac gcggcctttt tacggttcct 1860
ggccttttgc tggccttttg ctcacatgtt ctttcctgcg ttatcccctg attctgtgga 1920
taaccgtatt accgcctttg agtgagctga taccgctcgc cgcagccgaa cgaccgagcg 1980

-continued

```
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg tgtgatctgc ctcaaaccca   3060
cagcctgggt agcaggagga ccttgatgct cctggcacag atgaggagaa tctctctttt   3120
ctcctgcttg aaggacagac atgactttgg atttccccag gaggagtttg gcaaccagtt   3180
ccaaaaggct gaaaccatcc ctgtcctcca tgagatgatc cagcagatct tcaatctctt   3240
cagcacaaag gactcatctg ctgcttggga tgagaccctc ctagacaaat tctacactga   3300
actctaccag cagctgaatg acctggaagc ctgtgtgata caggggggtgg gggtgacaga   3360
gactcccctg atgaaggagg actccattct ggctgtgagg aaatacttcc aaagaatcac   3420
tctctatctg aaagagaaga aatacagccc ttgtgcctgg gaggttgtca gagcagaaat   3480
catgagatct ttttctttgt caacaaactt gcaagaaagt ttaagaagta aggaactcga   3540
gaacctgtat ttccagggcg ggtgctgcgg ccaaggcggc atgggtgggc cgggcgtggg   3600
tgttccgggc gtgggtgttc cgggtggcgg tgtgccgggc gcaggtgttc ctggtgtagg   3660
tgtgccgggt gttggtgtgc cgggtgttgg tgtaccaggt ggcggtgttc cgggtgcagg   3720
cgttccgggt ggcggtgtgc cgggcgtggg tgttccgggc gtgggtgttc cgggtggcgg   3780
tgtgccgggc gcaggtgttc ctggtgtagg tgtgccgggt gttggtgtgc cgggtgttgg   3840
tgtaccaggt ggcggtgttc cgggtgcagg cgttccgggt ggcggtgtgc cgggcgtggg   3900
tgttccgggc gtgggtgttc cgggtggcgg tgtgccgggc gcaggtgttc ctggtgtagg   3960
tgtgccgggt gttggtgtgc cgggtgttgg tgtaccaggt ggcggtgttc cgggtgcagg   4020
cgttccgggt ggcggtgtgc cgggcgtggg tgttccgggc gtgggtgttc cgggtggcgg   4080
tgtgccgggc gcaggtgttc ctggtgtagg tgtgccgggt gttggtgtgc cgggtgttgg   4140
tgtaccaggt ggcggtgttc cgggtgcagg cgttccgggt ggcggtgtgc cgggcgtggg   4200
tgttccgggc gtgggtgttc cgggtggcgg tgtgccgggc gcaggtgttc ctggtgtagg   4260
tgtgccgggt gttggtgtgc cgggtgttgg tgtaccaggt ggcggtgttc cgggtgcagg   4320
cgttccgggt ggcggtgtgc cgggcgtggg tgttccgggc gtgggtgttc cgggtggcgg   4380
```

-continued tgtgccgggc gcaggtgttc ctggtgtagg tgtgccgggt gttggtgtgc cgggtgttgg 4440
tgtaccaggt ggcggtgttc cgggtgcagg cgttccgggt ggcggtgtgc cgggcgtggg 4500
tgttccgggc gtgggtgttc cgggtggcgg tgtgccgggc gcaggtgttc ctggtgtagg 4560
tgtgccgggt gttggtgtgc cgggtgttgg tgtaccaggt ggcggtgttc cgggtgcagg 4620
cgttccgggt ggcggtgtgc cgggcgtggg tgttccgggc gtgggtgttc cgggtggcgg 4680
tgtgccgggc gcaggtgttc ctggtgtagg tgtgccgggt gttggtgtgc cgggtgttgg 4740
tgtaccaggt ggcggtgttc cgggtgcagg cgttccgggt ggcggtgtgc cgggcgtggg 4800
tgttccgggc gtgggtgttc cgggtggcgg tgtgccgggc gcaggtgttc ctggtgtagg 4860
tgtgccgggt gttggtgtgc cgggtgttgg tgtaccaggt ggcggtgttc cgggtgcagg 4920
cgttccgggt ggcggtgtgc cgggctggcc gtgataagct agcatgactg gtggacagca 4980
aatgggtcgg atccgaattc tgcagatatc catcacactg gcggccgctc gagcagatcc 5040
ggctgctaac aaagcccgaa aggaagctga gttggctgct gccaccgctg agcaataact 5100
agcataaccc cttggggcct ctaaacgggt cttgaggggt tttttgctga aaggaggaac 5160
tatatccgga taa 5173

<210> SEQ ID NO 41
<211> LENGTH: 4723
<212> TYPE: DNA
<213> ORGANISM: Artificial Sequence
<220> FEATURE:
<223> OTHER INFORMATION: Synthetic construct

<400> SEQUENCE: 41
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200

-continued

```
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg tgtgatctgc ctcaaaccca   3060
cagcctgggt agcaggagga ccttgatgct cctggcacag atgaggagaa tctctctttt   3120
ctcctgcttg aaggacagac atgactttgg atttccccag gaggagtttg gcaaccagtt   3180
ccaaaaggct gaaaccatcc ctgtcctcca tgagatgatc cagcagatct tcaatctctt   3240
cagcacaaag gactcatctg ctgcttggga tgagaccctc ctagacaaat tctacactga   3300
actctaccag cagctgaatg acctggaagc ctgtgtgata caggggggtgg gggtgacaga   3360
gactcccctg atgaaggagg actccattct ggctgtgagg aaatacttcc aaagaatcac   3420
tctctatctg aaagagaaga aatacagccc ttgtgcctgg gaggttgtca gagcagaaat   3480
catgagatct tttctctttgt caacaaactt gcaagaaagt ttaagaagta aggaactcga   3540
gaacctgtat ttccagggcg ggtgctgcgg ccaaggcggc atgggtgggc cgggcgtggg   3600
```

-continued tgttccgggc gtaggtgtcc caggtgtggg cgtaccgggc gttggtgttc ctggtgtcgg 3660
cgtgccgggc gtgggtgttc cgggcgtagg tgtcccaggt gtgggcgtac cgggcgttgg 3720
tgttcctggt gtcggcgtgc cgggcgtggg tgttccgggc gtaggtgtcc caggtgtggg 3780
cgtaccgggc gttggtgttc ctggtgtcgg cgtgccgggc gtgggtgttc cgggcgtagg 3840
tgtcccaggt gtgggcgtac cgggcgttgg tgttcctggt gtcggcgtgc cgggcgtggg 3900
tgttccgggc gtaggtgtcc caggtgtggg cgtaccgggc gttggtgttc ctggtgtcgg 3960
cgtgccgggc gtgggtgttc cgggcgtagg tgtcccaggt gtgggcgtac cgggcgttgg 4020
tgttcctggt gtcggcgtgc cgggcgtggg tgttccgggc gtaggtgtcc caggtgtggg 4080
cgtaccgggc gttggtgttc ctggtgtcgg cgtgccgggc gtgggtgttc cgggcgtagg 4140
tgtcccaggt gtgggcgtac cgggcgttgg tgttcctggt gtcggcgtgc cgggcgtggg 4200
tgttccgggc gtaggtgtcc caggtgtggg cgtaccgggc gttggtgttc ctggtgtcgg 4260
cgtgccgggc gtgggtgttc cgggcgtagg tgtcccaggt gtgggcgtac cgggcgttgg 4320
tgttcctggt gtcggcgtgc cgggcgtggg tgttccgggc gtaggtgtcc caggtgtggg 4380
cgtaccgggc gttggtgttc ctggtgtcgg cgtgccgggc gtgggtgttc cgggcgtagg 4440
tgtcccaggt gtgggcgtac cgggcgttgg tgttcctggt gtcggcgtgc cgggctggcc 4500
gtgataagct agcatgactg gtggacagca aatgggtcgg atccgaattc tgcagatatc 4560
catcacactg gcggccgctc gagcagatcc ggctgctaac aaagcccgaa aggaagctga 4620
gttggctgct gccaccgctg agcaataact agcataaccc cttggggcct ctaaacgggt 4680
cttgaggggt tttttgctga aaggaggaac tatatccgga taa 4723

<210> SEQ ID NO 42
<211> LENGTH: 5211
<212> TYPE: DNA
<213> ORGANISM: Artificial Sequence
<220> FEATURE:
<223> OTHER INFORMATION: Synthetic construct

<400> SEQUENCE: 42
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900

-continued

```
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg    2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg tgtgatctgc ctcaaaccca   3060
cagcctgggt agcaggagga ccttgatgct cctggcacag atgaggagaa tctctctttt   3120
ctcctgcttg aaggacagac atgactttgg atttccccag gaggagtttg gcaaccagtt   3180
ccaaaaggct gaaaccatcc ctgtcctcca tgagatgatc cagcagatct tcaatctctt   3240
cagcacaaag gactcatctg ctgcttggga tgagaccctc ctagacaaat tctacactga   3300
```

-continued

```
actctaccag cagctgaatg acctggaagc ctgtgtgata caggggtgg gggtgacaga   3360

gactcccctg atgaaggagg actccattct ggctgtgagg aaatacttcc aaagaatcac   3420

tctctatctg aaagagaaga aatacagccc ttgtgcctgg gaggttgtca gagcagaaat   3480

catgagatct ttttctttgt caacaaactt gcaagaaagt ttaagaagta aggaactcga   3540

gaacctgtat ttccaaggcg gcatgggtgg gccgggcgtg ggtgttccgg gcgtgggtgt   3600

tccgggtggc ggtgtgccgg gcgcaggtgt tcctggtgta ggtgtgccgg gtgttggtgt   3660

gccgggtgtt ggtgtaccag gtggcggtgt tccgggtgca ggcgttccgg gtggcggtgt   3720

gccgggcgtg ggtgttccgg gcgtgggtgt tccgggtggc ggtgtgccgg gcgcaggtgt   3780

tcctggtgta ggtgtgccgg gtgttggtgt gccgggtgtt ggtgtaccag gtggcggtgt   3840

tccgggtgca ggcgttccgg gtggcggtgt gccgggcgtg ggtgttccgg gcgtgggtgt   3900

tccgggtggc ggtgtgccgg gcgcaggtgt tcctggtgta ggtgtgccgg gtgttggtgt   3960

gccgggtgtt ggtgtaccag gtggcggtgt tccgggtgca ggcgttccgg gtggcggtgt   4020

gccgggcgtg ggtgttccgg gcgtgggtgt tccgggtggc ggtgtgccgg gcgcaggtgt   4080

tcctggtgta ggtgtgccgg gtgttggtgt gccgggtgtt ggtgtaccag gtggcggtgt   4140

tccgggtgca ggcgttccgg gtggcggtgt gccgggcgtg ggtgttccgg gcgtgggtgt   4200

tccgggtggc ggtgtgccgg gcgcaggtgt tcctggtgta ggtgtgccgg gtgttggtgt   4260

gccgggtgtt ggtgtaccag gtggcggtgt tccgggtgca ggcgttccgg gtggcggtgt   4320

gccgggcgtg ggtgttccgg gcgtgggtgt tccgggtggc ggtgtgccgg gcgcaggtgt   4380

tcctggtgta ggtgtgccgg gtgttggtgt gccgggtgtt ggtgtaccag gtggcggtgt   4440

tccgggtgca ggcgttccgg gtggcggtgt gccgggcgtg ggtgttccgg gcgtgggtgt   4500

tccgggtggc ggtgtgccgg gcgcaggtgt tcctggtgta ggtgtgccgg gtgttggtgt   4560

gccgggtgtt ggtgtaccag gtggcggtgt tccgggtgca ggcgttccgg gtggcggtgt   4620

gccgggcgtg ggtgttccgg gcgtgggtgt tccgggtggc ggtgtgccgg gcgcaggtgt   4680

tcctggtgta ggtgtgccgg gtgttggtgt gccgggtgtt ggtgtaccag gtggcggtgt   4740

tccgggtgca ggcgttccgg gtggcggtgt gccgggcgtg ggtgttccgg gcgtgggtgt   4800

tccgggtggc ggtgtgccgg gcgcaggtgt tcctggtgta ggtgtgccgg gtgttggtgt   4860

gccgggtgtt ggtgtaccag gtggcggtgt tccgggtgca ggcgttccgg gtggcggtgt   4920

gccgggctgg ccttgctgct gataagctag catgactggt ggacagcaaa tgggtcggga   4980

ttcaagcttg gtaccgagct cggatccact agtaacggcc gccagtgtgc tggaattctg   5040

cagatatcca tcacactggc ggccgctcga gcagatccgg ctgctaacaa agcccgaaag   5100

gaagctgagt tggctgctgc caccgctgag caataactag cataacccct tggggcctct   5160

aaacgggtct tgaggggttt tttgctgaaa ggaggaacta tatccggata a            5211
```

<210> SEQ ID NO 43
<211> LENGTH: 4761
<212> TYPE: DNA
<213> ORGANISM: Artificial Sequence
<220> FEATURE:
<223> OTHER INFORMATION: Synthetic construct

<400> SEQUENCE: 43

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120
```

-continued

```
tttatttttc taaatacatt caaatatgta tccgctcatg agacaataac cctgataaat    180
gcttcaataa tattgaaaaa ggaagagtat gagtattcaa catttccgtg tcgcccttat    240
tcccttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
```

-continued

```
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg tgtgatctgc ctcaaaccca   3060
cagcctgggt agcaggagga ccttgatgct cctggcacag atgaggagaa tctctctttt   3120
ctcctgcttg aaggacagac atgactttgg atttccccag gaggagtttg gcaaccagtt   3180
ccaaaaggct gaaaccatcc ctgtcctcca tgagatgatc cagcagatct tcaatctctt   3240
cagcacaaag gactcatctg ctgcttggga tgagaccctc ctagacaaat tctacactga   3300
actctaccag cagctgaatg acctggaagc ctgtgtgata caggggggtgg gggtgacaga   3360
gactcccctg atgaaggagg actccattct ggctgtgagg aaatacttcc aaagaatcac   3420
tctctatctg aaagagaaga aatacagccc ttgtgcctgg gaggttgtca gagcagaaat   3480
catgagatct tttttctttgt caacaaactt gcaagaaagt ttaagaagta aggaactcga   3540
gaacctgtat ttccaaggcg gcatgggtgg gccgggcgtg ggtgttccgg gcgtaggtgt   3600
cccaggtgtg ggcgtaccgg gcgttggtgt tcctggtgtc ggcgtgccgg gcgtgggtgt   3660
tccgggcgta ggtgtcccag gtgtgggcgt accgggcgtt ggtgttcctg gtgtcggcgt   3720
gccgggcgtg ggtgttccgg gcgtaggtgt cccaggtgtg ggcgtaccgg gcgttggtgt   3780
tcctggtgtc ggcgtgccgg gcgtgggtgt tccgggcgta ggtgtcccag gtgtgggcgt   3840
accgggcgtt ggtgttcctg gtgtcggcgt gccgggcgtg ggtgttccgg gcgtaggtgt   3900
cccaggtgtg ggcgtaccgg gcgttggtgt tcctggtgtc ggcgtgccgg gcgtgggtgt   3960
tccgggcgta ggtgtcccag gtgtgggcgt accgggcgtt ggtgttcctg gtgtcggcgt   4020
gccgggcgtg ggtgttccgg gcgtaggtgt cccaggtgtg ggcgtaccgg gcgttggtgt   4080
tcctggtgtc ggcgtgccgg gcgtgggtgt tccgggcgta ggtgtcccag gtgtgggcgt   4140
accgggcgtt ggtgttcctg gtgtcggcgt gccgggcgtg ggtgttccgg gcgtaggtgt   4200
cccaggtgtg ggcgtaccgg gcgttggtgt tcctggtgtc ggcgtgccgg gcgtgggtgt   4260
tccgggcgta ggtgtcccag gtgtgggcgt accgggcgtt ggtgttcctg gtgtcggcgt   4320
gccgggcgtg ggtgttccgg gcgtaggtgt cccaggtgtg ggcgtaccgg gcgttggtgt   4380
tcctggtgtc ggcgtgccgg gcgtgggtgt tccgggcgta ggtgtcccag gtgtgggcgt   4440
accgggcgtt ggtgttcctg gtgtcggcgt gccgggctgg ccttgctgct gataagctag   4500
catgactggt ggacagcaaa tgggtcggga ttcaagcttg gtaccgagct cggatccact   4560
agtaacggcc gccagtgtgc tggaattctg cagatatcca tcacactggc ggccgctcga   4620
gcagatccgg ctgctaacaa agcccgaaag gaagctgagt tggctgctgc caccgctgag   4680
caataactag cataacccct tggggcctct aaacgggtct tgaggggttt tttgctgaaa   4740
ggaggaacta tatccggata a                                              4761
```

<210> SEQ ID NO 44

-continued

<211> LENGTH: 5155
<212> TYPE: DNA
<213> ORGANISM: Artificial Sequence
<220> FEATURE:
<223> OTHER INFORMATION: Synthetic construct

<400> SEQUENCE: 44
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440
tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680
ggtaagcggc agggtcggaa caggagagcg cacgagggag cttccagggg gaaacgcctg 1740
gtatctttat agtcctgtcg ggtttcgcca cctctgactt gagcgtcgat ttttgtgatg 1800
ctcgtcaggg gggcggagcc tatggaaaaa cgccagcaac gcggcctttt tacggttcct 1860
ggccttttgc tggccttttg ctcacatgtt ctttcctgcg ttatcccctg attctgtgga 1920
taaccgtatt accgcctttg agtgagctga taccgctcgc cgcagccgaa cgaccgagcg 1980
cagcgagtca gtgagcgagg aagcggaaga gcgcctgatg cggtattttc tccttacgca 2040
tctgtgcggt atttcacacc gcatatatgg tgcactctca gtacaatctg ctctgatgcc 2100
gcatagttaa gccagtatac actccgctat cgctacgtga ctgggtcatg gctgcgcccc 2160

-continued

```
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg tgtgatctgc ctcaaaccca   3060
cagcctgggt agcaggagga ccttgatgct cctggcacag atgaggagaa tctctctttt   3120
ctcctgcttg aaggacagac atgactttgg atttccccag gaggagtttg gcaaccagtt   3180
ccaaaaggct gaaaccatcc ctgtcctcca tgagatgatc cagcagatct tcaatctctt   3240
cagcacaaag gactcatctg ctgcttggga tgagaccctc ctagacaaat tctacactga   3300
actctaccag cagctgaatg acctggaagc ctgtgtgata caggggggtgg gggtgacaga   3360
gactcccctg atgaaggagg actccattct ggctgtgagg aaatacttcc aaagaatcac   3420
tctctatctg aaagagaaga aatacagccc ttgtgcctgg gaggttgtca gagcagaaat   3480
catgagatct ttttctttgt caacaaactt gcaagaaagt ttaagaagta aggaactcga   3540
gaacctgtat ttccaaggcg gcatgggtgg gccgggcgtg ggtgttccgg gcgtgggtgt   3600
tccgggtggc ggtgtgccgg gcgcaggtgt tcctggtgta ggtgtgccgg gtgttggtgt   3660
gccgggtgtt ggtgtaccag gtggcggtgt tccgggtgca ggcgttccgg gtggcggtgt   3720
gccgggcgtg ggtgttccgg gcgtgggtgt tccgggtggc ggtgtgccgg gcgcaggtgt   3780
tcctggtgta ggtgtgccgg gtgttggtgt gccgggtgtt ggtgtaccag gtggcggtgt   3840
tccgggtgca ggcgttccgg gtggcggtgt gccgggcgtg ggtgttccgg gcgtgggtgt   3900
tccgggtggc ggtgtgccgg gcgcaggtgt tcctggtgta ggtgtgccgg gtgttggtgt   3960
gccgggtgtt ggtgtaccag gtggcggtgt tccgggtgca ggcgttccgg gtggcggtgt   4020
gccgggcgtg ggtgttccgg gcgtgggtgt tccgggtggc ggtgtgccgg gcgcaggtgt   4080
tcctggtgta ggtgtgccgg gtgttggtgt gccgggtgtt ggtgtaccag gtggcggtgt   4140
tccgggtgca ggcgttccgg gtggcggtgt gccgggcgtg ggtgttccgg gcgtgggtgt   4200
tccgggtggc ggtgtgccgg gcgcaggtgt tcctggtgta ggtgtgccgg gtgttggtgt   4260
gccgggtgtt ggtgtaccag gtggcggtgt tccgggtgca ggcgttccgg gtggcggtgt   4320
gccgggcgtg ggtgttccgg gcgtgggtgt tccgggtggc ggtgtgccgg gcgcaggtgt   4380
tcctggtgta ggtgtgccgg gtgttggtgt gccgggtgtt ggtgtaccag gtggcggtgt   4440
tccgggtgca ggcgttccgg gtggcggtgt gccgggcgtg ggtgttccgg gcgtgggtgt   4500
```

-continued

```
tccgggtggc ggtgtgccgg gcgcaggtgt tcctggtgta ggtgtgccgg gtgttggtgt   4560

gccgggtgtt ggtgtaccag gtggcggtgt tccgggtgca ggcgttccgg gtggcggtgt   4620

gccgggcgtg ggtgttccgg gcgtgggtgt tccgggtggc ggtgtgccgg gcgcaggtgt   4680

tcctggtgta ggtgtgccgg gtgttggtgt gccgggtgtt ggtgtaccag gtggcggtgt   4740

tccgggtgca ggcgttccgg gtggcggtgt gccgggcgtg ggtgttccgg gcgtgggtgt   4800

tccgggtggc ggtgtgccgg gcgcaggtgt tcctggtgta ggtgtgccgg gtgttggtgt   4860

gccgggtgtt ggtgtaccag gtggcggtgt tccgggtgca ggcgttccgg gtggcggtgt   4920

gccgggctgg ccgtgataag ctagcatgac tggtggacag caaatgggtc ggatccgaat   4980

tctgcagata tccatcacac tggcggccgc tcgagcagat ccggctgcta acaaagcccg   5040

aaaggaagct gagttggctg ctgccaccgc tgagcaataa ctagcataac cccttggggc   5100

ctctaaacgg gtcttgaggg gttttttgct gaaaggagga actatatccg gataa        5155
```

<210> SEQ ID NO 45
<211> LENGTH: 4705
<212> TYPE: DNA
<213> ORGANISM: Artificial Sequence
<220> FEATURE:
<223> OTHER INFORMATION: Synthetic construct

<400> SEQUENCE: 45

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840

ggataaagtt gcaggaccac ttctgcgctc ggcccttccg gctggctggt ttattgctga    900

taaatctgga gccggtgagc gtgggtctcg cggtatcatt gcagcactgg ggccagatgg    960

taagccctcc cgtatcgtag ttatctacac gacggggagt caggcaacta tggatgaacg   1020

aaatagacag atcgctgaga taggtgcctc actgattaag cattggtaac tgtcagacca   1080

agtttactca tatatacttt agattgattt aaaacttcat ttttaattta aaaggatcta   1140

ggtgaagatc ctttttgata atctcatgac caaaatccct taacgtgagt tttcgttcca   1200

ctgagcgtca gaccccgtag aaaagatcaa aggatcttct tgagatcctt tttttctgcg   1260

cgtaatctgc tgcttgcaaa caaaaaaacc accgctacca gcggtggttt gtttgccgga   1320

tcaagagcta ccaactcttt ttccgaaggt aactggcttc agcagagcgc agataccaaa   1380

tactgtcctt ctagtgtagc cgtagttagg ccaccacttc aagaactctg tagcaccgcc   1440
```

-continued tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680
ggtaagcggc agggtcggaa caggagagcg cacgagggag cttccagggg gaaacgcctg 1740
gtatctttat agtcctgtcg ggtttcgcca cctctgactt gagcgtcgat ttttgtgatg 1800
ctcgtcaggg gggcggagcc tatggaaaaa cgccagcaac gcggcctttt tacggttcct 1860
ggccttttgc tggccttttg ctcacatgtt ctttcctgcg ttatcccctg attctgtgga 1920
taaccgtatt accgcctttg agtgagctga taccgctcgc cgcagccgaa cgaccgagcg 1980
cagcgagtca gtgagcgagg aagcggaaga gcgcctgatg cggtattttc tccttacgca 2040
tctgtgcggt atttcacacc gcatatatgg tgcactctca gtacaatctg ctctgatgcc 2100
gcatagttaa gccagtatac actccgctat cgctacgtga ctgggtcatg gctgcgcccc 2160
gacacccgcc aacacccgct gacgcgccct gacgggcttg tctgctcccg gcatccgctt 2220
acagacaagc tgtgaccgtc tccgggagct gcatgtgtca gaggttttca ccgtcatcac 2280
cgaaacgcgc gaggcagctg cggtaaagct catcagcgtg gtcgtgaagc gattcacaga 2340
tgtctgcctg ttcatccgcg tccagctcgt tgagtttctc cagaagcgtt aatgtctggc 2400
ttctgataaa gcgggccatg ttaagggcgg tttttcctg tttggtcact gatgcctccg 2460
tgtaaggggg atttctgttc atgggggtaa tgataccgat gaaacgagag aggatgctca 2520
cgatacgggt tactgatgat gaacatgccc ggttactgga acgttgtgag ggtaaacaac 2580
tggcggtatg gatgcggcgg gaccagagaa aaatcactca gggtcaatgc cagcgcttcg 2640
ttaatacaga tgtaggtgtt ccacagggta gccagcagca tcctgcgatg cagatccgga 2700
acataatggt gcagggcgct gacttccgcg tttccagact ttacgaaaca cggaaaccga 2760
agaccattca tgttgttgct caggtcgcag acgttttgca gcagcagtcg cttcacgttc 2820
gctcgcgtat cggtgattca ttctgctaac cagtaaggca accccgccag cctagccggg 2880
tcctcaacga caggagcacg atcatgcgca cccgtggcca ggacccaacg ctgcccgaga 2940
tctcgatccc gcgaaattaa tacgactcac tatagggaga ccacaacggt ttccctctag 3000
aaataatttt gtttaacttt aagaaggaga tatacatatg tgtgatctgc ctcaaaccca 3060
cagcctgggt agcaggagga ccttgatgct cctggcacag atgaggagaa tctctctttt 3120
ctcctgcttg aaggacagac atgactttgg atttccccag gaggagtttg gcaaccagtt 3180
ccaaaaggct gaaaccatcc ctgtcctcca tgagatgatc cagcagatct tcaatctctt 3240
cagcacaaag gactcatctg ctgcttggga tgagaccctc ctagacaaat tctacactga 3300
actctaccag cagctgaatg acctggaagc ctgtgtgata caggggggtgg gggtgacaga 3360
gactcccctg atgaaggagg actccattct ggctgtgagg aaatacttcc aaagaatcac 3420
tctctatctg aaagagaaga aatacagccc ttgtgcctgg gaggttgtca gagcagaaat 3480
catgagatct tttctttgt caacaaactt gcaagaaagt ttaagaagta aggaactcga 3540
gaacctgtat ttccaaggcg gcatgggtgg gccgggcgtg ggtgttccgg gcgtaggtgt 3600
cccaggtgtg ggcgtaccgg gcgttggtgt tcctggtgtc ggcgtgccgg gcgtgggtgt 3660
tccgggcgta ggtgtcccag gtgtgggcgt accgggcgtt ggtgttcctg gtgtcggcgt 3720
gccgggcgtg ggtgttccgg gcgtaggtgt cccaggtgtg ggcgtaccgg gcgttggtgt 3780

-continued

```
tcctggtgtc ggcgtgccgg gcgtgggtgt tccgggcgta ggtgtcccag gtgtgggcgt   3840

accgggcgtt ggtgttcctg gtgtcggcgt gccgggcgtg ggtgttccgg gcgtaggtgt   3900

cccaggtgtg ggcgtaccgg gcgttggtgt tcctggtgtc ggcgtgccgg gcgtgggtgt   3960

tccgggcgta ggtgtcccag gtgtgggcgt accgggcgtt ggtgttcctg gtgtcggcgt   4020

gccgggcgtg ggtgttccgg gcgtaggtgt cccaggtgtg ggcgtaccgg gcgttggtgt   4080

tcctggtgtc ggcgtgccgg gcgtgggtgt tccgggcgta ggtgtcccag gtgtgggcgt   4140

accgggcgtt ggtgttcctg gtgtcggcgt gccgggcgtg ggtgttccgg gcgtaggtgt   4200

cccaggtgtg ggcgtaccgg gcgttggtgt tcctggtgtc ggcgtgccgg gcgtgggtgt   4260

tccgggcgta ggtgtcccag gtgtgggcgt accgggcgtt ggtgttcctg gtgtcggcgt   4320

gccgggcgtg ggtgttccgg gcgtaggtgt cccaggtgtg ggcgtaccgg gcgttggtgt   4380

tcctggtgtc ggcgtgccgg gcgtgggtgt tccgggcgta ggtgtcccag gtgtgggcgt   4440

accgggcgtt ggtgttcctg gtgtcggcgt gccgggctgg ccgtgataag ctagcatgac   4500

tggtggacag caaatgggtc ggatccgaat tctgcagata tccatcacac tggcggccgc   4560

tcgagcagat ccggctgcta acaaagcccg aaaggaagct gagttggctg ctgccaccgc   4620

tgagcaataa ctagcataac cccttggggc ctctaaacgg gtcttgaggg gttttttgct   4680

gaaaggagga actatatccg gataa                                         4705
```

```
<210> SEQ ID NO 46
<211> LENGTH: 35
<212> TYPE: DNA
<213> ORGANISM: Artificial Sequence
<220> FEATURE:
<223> OTHER INFORMATION: oligo

<400> SEQUENCE: 46

tcgagaacct gtatttccag ggcgggtgct gcggc                                35


<210> SEQ ID NO 47
<211> LENGTH: 35
<212> TYPE: DNA
<213> ORGANISM: Artificial Sequence
<220> FEATURE:
<223> OTHER INFORMATION: oligo

<400> SEQUENCE: 47

cttggccgca gcagccgccc tggaaataca ggttc                                35


<210> SEQ ID NO 48
<211> LENGTH: 14
<212> TYPE: PRT
<213> ORGANISM: Artificial Sequence
<220> FEATURE:
<223> OTHER INFORMATION: synthetic construct

<400> SEQUENCE: 48

Leu Glu Asn Leu Tyr Phe Gln Gly Gly Cys Cys Gly Gln Gly
1               5                   10


<210> SEQ ID NO 49
<211> LENGTH: 82
<212> TYPE: DNA
<213> ORGANISM: Artificial Sequence
<220> FEATURE:
<223> OTHER INFORMATION: annealed oligo

<400> SEQUENCE: 49
```

-continued ctcgagaacc tgtatttcca gggcgggtgc tgcggccaag ggagctcttg gacataaagg 60
tcccgcccac gacgccggtt cc 82

<210> SEQ ID NO 50
<211> LENGTH: 4681
<212> TYPE: DNA
<213> ORGANISM: Artificial Sequence
<220> FEATURE:
<223> OTHER INFORMATION: Synthetic construct

<400> SEQUENCE: 50
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440
tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680
ggtaagcggc agggtcggaa caggagagcg cacgagggag cttccagggg gaaacgcctg 1740
gtatctttat agtcctgtcg ggtttcgcca cctctgactt gagcgtcgat ttttgtgatg 1800
ctcgtcaggg gggcggagcc tatggaaaaa cgccagcaac gcggcctttt tacggttcct 1860
ggccttttgc tggccttttg ctcacatgtt ctttcctgcg ttatcccctg attctgtgga 1920
taaccgtatt accgcctttg agtgagctga taccgctcgc cgcagccgaa cgaccgagcg 1980

-continued

```
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg ccgctcgaga acctgtattt   3060
ccagggcggg tgctgcggcc aaggcggcat gggtgggccg ggcgtgggtg ttccgggcgt   3120
gggtgttccg ggtggcggtg tgccgggcgc aggtgttcct ggtgtaggtg tgccgggtgt   3180
tggtgtgccg ggtgttggtg taccaggtgg cggtgttccg ggtgcaggcg ttccgggtgg   3240
cggtgtgccg ggcgtgggtg ttccgggcgt gggtgttccg ggtggcggtg tgccgggcgc   3300
aggtgttcct ggtgtaggtg tgccgggtgt tggtgtgccg ggtgttggtg taccaggtgg   3360
cggtgttccg ggtgcaggcg ttccgggtgg cggtgtgccg ggcgtgggtg ttccgggcgt   3420
gggtgttccg ggtggcggtg tgccgggcgc aggtgttcct ggtgtaggtg tgccgggtgt   3480
tggtgtgccg ggtgttggtg taccaggtgg cggtgttccg ggtgcaggcg ttccgggtgg   3540
cggtgtgccg ggcgtgggtg ttccgggcgt gggtgttccg ggtggcggtg tgccgggcgc   3600
aggtgttcct ggtgtaggtg tgccgggtgt tggtgtgccg ggtgttggtg taccaggtgg   3660
cggtgttccg ggtgcaggcg ttccgggtgg cggtgtgccg ggcgtgggtg ttccgggcgt   3720
gggtgttccg ggtggcggtg tgccgggcgc aggtgttcct ggtgtaggtg tgccgggtgt   3780
tggtgtgccg ggtgttggtg taccaggtgg cggtgttccg ggtgcaggcg ttccgggtgg   3840
cggtgtgccg ggcgtgggtg ttccgggcgt gggtgttccg ggtggcggtg tgccgggcgc   3900
aggtgttcct ggtgtaggtg tgccgggtgt tggtgtgccg ggtgttggtg taccaggtgg   3960
cggtgttccg ggtgcaggcg ttccgggtgg cggtgtgccg ggcgtgggtg ttccgggcgt   4020
gggtgttccg ggtggcggtg tgccgggcgc aggtgttcct ggtgtaggtg tgccgggtgt   4080
tggtgtgccg ggtgttggtg taccaggtgg cggtgttccg ggtgcaggcg ttccgggtgg   4140
cggtgtgccg ggcgtgggtg ttccgggcgt gggtgttccg ggtggcggtg tgccgggcgc   4200
aggtgttcct ggtgtaggtg tgccgggtgt tggtgtgccg ggtgttggtg taccaggtgg   4260
cggtgttccg ggtgcaggcg ttccgggtgg cggtgtgccg ggcgtgggtg ttccgggcgt   4320
```

-continued gggtgttccg ggtggcggtg tgccgggcgc aggtgttcct ggtgtaggtg tgccgggtgt 4380
tggtgtgccg ggtgttggtg taccaggtgg cggtgttccg ggtgcaggcg ttccgggtgg 4440
cggtgtgccg ggctggccgt gataagctag catgactggt ggacagcaaa tgggtcggat 4500
ccgaattctg cagatatcca tcacactggc ggccgctcga gcagatccgg ctgctaacaa 4560
agcccgaaag gaagctgagt tggctgctgc caccgctgag caataactag cataacccct 4620
tggggcctct aaacgggtct tgaggggttt tttgctgaaa ggaggaacta tatccggata 4680
a 4681

<210> SEQ ID NO 51
<211> LENGTH: 4231
<212> TYPE: DNA
<213> ORGANISM: Artificial Sequence
<220> FEATURE:
<223> OTHER INFORMATION: Synthetic construct

<400> SEQUENCE: 51
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440
tacatacctc gctctgctaa tcctgttacc agtggctgct gccagtggcg ataagtcgtg 1500
tcttaccggg ttggactcaa gacgatagtt accggataag gcgcagcggt cgggctgaac 1560
ggggggttcg tgcacacagc ccagcttgga gcgaacgacc tacaccgaac tgagatacct 1620
acagcgtgag ctatgagaaa gcgccacgct tcccgaaggg agaaaggcgg acaggtatcc 1680

-continued

```
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg ccgctcgaga acctgtattt   3060
ccagggcggg tgctgcggcc aaggcggcat gggtgggccg ggcgtgggtg ttccgggcgt   3120
aggtgtccca ggtgtgggcg taccgggcgt tggtgttcct ggtgtcggcg tgccgggcgt   3180
gggtgttccg ggcgtaggtg tcccaggtgt gggcgtaccg ggcgttggtg ttcctggtgt   3240
cggcgtgccg ggcgtgggtg ttccgggcgt aggtgtccca ggtgtgggcg taccgggcgt   3300
tggtgttcct ggtgtcggcg tgccgggcgt gggtgttccg ggcgtaggtg tcccaggtgt   3360
gggcgtaccg ggcgttggtg ttcctggtgt cggcgtgccg ggcgtgggtg ttccgggcgt   3420
aggtgtccca ggtgtgggcg taccgggcgt tggtgttcct ggtgtcggcg tgccgggcgt   3480
gggtgttccg ggcgtaggtg tcccaggtgt gggcgtaccg ggcgttggtg ttcctggtgt   3540
cggcgtgccg ggcgtgggtg ttccgggcgt aggtgtccca ggtgtgggcg taccgggcgt   3600
tggtgttcct ggtgtcggcg tgccgggcgt gggtgttccg ggcgtaggtg tcccaggtgt   3660
gggcgtaccg ggcgttggtg ttcctggtgt cggcgtgccg ggcgtgggtg ttccgggcgt   3720
aggtgtccca ggtgtgggcg taccgggcgt tggtgttcct ggtgtcggcg tgccgggcgt   3780
gggtgttccg ggcgtaggtg tcccaggtgt gggcgtaccg ggcgttggtg ttcctggtgt   3840
cggcgtgccg ggcgtgggtg ttccgggcgt aggtgtccca ggtgtgggcg taccgggcgt   3900
tggtgttcct ggtgtcggcg tgccgggcgt gggtgttccg ggcgtaggtg tcccaggtgt   3960
gggcgtaccg ggcgttggtg ttcctggtgt cggcgtgccg ggctggccgt gataagctag   4020
```

-continued

```
catgactggt ggacagcaaa tgggtcggat ccgaattctg cagatatcca tcacactggc   4080

ggccgctcga gcagatccgg ctgctaacaa agcccgaaag gaagctgagt tggctgctgc   4140

caccgctgag caataactag cataacccct tggggcctct aaacgggtct tgaggggttt   4200

tttgctgaaa ggaggaacta tatccggata a                                   4231
```

<210> SEQ ID NO 52
<211> LENGTH: 19
<212> TYPE: DNA
<213> ORGANISM: Artificial Sequence
<220> FEATURE:
<223> OTHER INFORMATION: oligo

<400> SEQUENCE: 52

```
tggccttgct gctgataag                                                   19
```

<210> SEQ ID NO 53
<211> LENGTH: 26
<212> TYPE: DNA
<213> ORGANISM: Artificial Sequence
<220> FEATURE:
<223> OTHER INFORMATION: oligo

<400> SEQUENCE: 53

```
ctagcttatc agcagcaagg ccagcc                                           26
```

<210> SEQ ID NO 54
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(8)
<223> OTHER INFORMATION: Xaa at positions 7 and 8 can be any amino acid coordinating with the codons of SEQ ID NO 55
<220> FEATURE:
<221> NAME/KEY: MISC_FEATURE
<222> LOCATION: (7)..(8)
<223> OTHER INFORMATION: Xaa at positions 7 and 8 can be any amino acid coordinating with the codons of SEQ ID NO 55

<400> SEQUENCE: 54

```
Pro Gly Trp Pro Cys Cys Xaa Xaa Ala Ser
1               5                   10
```

<210> SEQ ID NO 55
<211> LENGTH: 62
<212> TYPE: DNA
<213> ORGANISM: Artificial Sequence
<220> FEATURE:
<223> OTHER INFORMATION: annealed oligos

<400> SEQUENCE: 55

```
gccgggctgg ccttgctgct gataagctag ccggcccgac cggaacgacg actattcgat     60

cg                                                                     62
```

<210> SEQ ID NO 56
<211> LENGTH: 4719
<212> TYPE: DNA
<213> ORGANISM: Artificial Sequence
<220> FEATURE:
<223> OTHER INFORMATION: Synthetic construct

<400> SEQUENCE: 56

-continued

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
```

-continued

```
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tatacatatg ccgctcgaga acctgtattt   3060
ccaaggcggc atgggtgggc cgggcgtggg tgttccgggc gtgggtgttc cgggtggcgg   3120
tgtgccgggc gcaggtgttc ctggtgtagg tgtgccgggt gttggtgtgc cgggtgttgg   3180
tgtaccaggt ggcggtgttc cgggtgcagg cgttccgggt ggcggtgtgc cgggcgtggg   3240
tgttccgggc gtgggtgttc cgggtggcgg tgtgccgggc gcaggtgttc ctggtgtagg   3300
tgtgccgggt gttggtgtgc cgggtgttgg tgtaccaggt ggcggtgttc cgggtgcagg   3360
cgttccgggt ggcggtgtgc cgggcgtggg tgttccgggc gtgggtgttc cgggtggcgg   3420
tgtgccgggc gcaggtgttc ctggtgtagg tgtgccgggt gttggtgtgc cgggtgttgg   3480
tgtaccaggt ggcggtgttc cgggtgcagg cgttccgggt ggcggtgtgc cgggcgtggg   3540
tgttccgggc gtgggtgttc cgggtggcgg tgtgccgggc gcaggtgttc ctggtgtagg   3600
tgtgccgggt gttggtgtgc cgggtgttgg tgtaccaggt ggcggtgttc cgggtgcagg   3660
cgttccgggt ggcggtgtgc cgggcgtggg tgttccgggc gtgggtgttc cgggtggcgg   3720
tgtgccgggc gcaggtgttc ctggtgtagg tgtgccgggt gttggtgtgc cgggtgttgg   3780
tgtaccaggt ggcggtgttc cgggtgcagg cgttccgggt ggcggtgtgc cgggcgtggg   3840
tgttccgggc gtgggtgttc cgggtggcgg tgtgccgggc gcaggtgttc ctggtgtagg   3900
tgtgccgggt gttggtgtgc cgggtgttgg tgtaccaggt ggcggtgttc cgggtgcagg   3960
cgttccgggt ggcggtgtgc cgggcgtggg tgttccgggc gtgggtgttc cgggtggcgg   4020
tgtgccgggc gcaggtgttc ctggtgtagg tgtgccgggt gttggtgtgc cgggtgttgg   4080
tgtaccaggt ggcggtgttc cgggtgcagg cgttccgggt ggcggtgtgc cgggcgtggg   4140
tgttccgggc gtgggtgttc cgggtggcgg tgtgccgggc gcaggtgttc ctggtgtagg   4200
tgtgccgggt gttggtgtgc cgggtgttgg tgtaccaggt ggcggtgttc cgggtgcagg   4260
cgttccgggt ggcggtgtgc cgggcgtggg tgttccgggc gtgggtgttc cgggtggcgg   4320
tgtgccgggc gcaggtgttc ctggtgtagg tgtgccgggt gttggtgtgc cgggtgttgg   4380
tgtaccaggt ggcggtgttc cgggtgcagg cgttccgggt ggcggtgtgc cgggctggcc   4440
ttgctgctga taagctagca tgactggtgg acagcaaatg ggtcgggatt caagcttggt   4500
accgagctcg gatccactag taacggccgc cagtgtgctg gaattctgca gatatccatc   4560
acactggcgg ccgctcgagc agatccggct gctaacaaag cccgaaagga agctgagttg   4620
gctgctgcca ccgctgagca ataactagca taaccccttg gggcctctaa acgggtcttg   4680
aggggttttt tgctgaaagg aggaactata tccggataa                         4719
```

-continued

<210> SEQ ID NO 57
<211> LENGTH: 4269
<212> TYPE: DNA
<213> ORGANISM: Artificial Sequence
<220> FEATURE:
<223> OTHER INFORMATION: Synthetic construct

<400> SEQUENCE: 57

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840

ggataaagtt gcaggaccac ttctgcgctc ggcccttccg gctggctggt ttattgctga    900

taaatctgga gccggtgagc gtgggtctcg cggtatcatt gcagcactgg ggccagatgg    960

taagccctcc cgtatcgtag ttatctacac gacggggagt caggcaacta tggatgaacg   1020

aaatagacag atcgctgaga taggtgcctc actgattaag cattggtaac tgtcagacca   1080

agtttactca tatatacttt agattgattt aaaacttcat ttttaattta aaaggatcta   1140

ggtgaagatc ctttttgata atctcatgac caaaatccct taacgtgagt tttcgttcca   1200

ctgagcgtca gaccccgtag aaaagatcaa aggatcttct tgagatcctt tttttctgcg   1260

cgtaatctgc tgcttgcaaa caaaaaaacc accgctacca gcggtggttt gtttgccgga   1320

tcaagagcta ccaactcttt ttccgaaggt aactggcttc agcagagcgc agataccaaa   1380

tactgtcctt ctagtgtagc cgtagttagg ccaccacttc aagaactctg tagcaccgcc   1440

tacatacctc gctctgctaa tcctgttacc agtggctgct gccagtggcg ataagtcgtg   1500

tcttaccggg ttggactcaa gacgatagtt accggataag gcgcagcggt cgggctgaac   1560

ggggggttcg tgcacacagc ccagcttgga gcgaacgacc tacaccgaac tgagatacct   1620

acagcgtgag ctatgagaaa gcgccacgct tcccgaaggg agaaaggcgg acaggtatcc   1680

ggtaagcggc agggtcggaa caggagagcg cacgagggag cttccagggg gaaacgcctg   1740

gtatctttat agtcctgtcg ggtttcgcca cctctgactt gagcgtcgat ttttgtgatg   1800

ctcgtcaggg gggcggagcc tatggaaaaa cgccagcaac gcggcctttt tacggttcct   1860

ggccttttgc tggccttttg ctcacatgtt ctttcctgcg ttatcccctg attctgtgga   1920

taaccgtatt accgcctttg agtgagctga taccgctcgc cgcagccgaa cgaccgagcg   1980

cagcgagtca gtgagcgagg aagcggaaga gcgcctgatg cggtattttc tccttacgca   2040

tctgtgcggt atttcacacc gcatatatgg tgcactctca gtacaatctg ctctgatgcc   2100
```

```
gcatagttaa gccagtatac actccgctat cgctacgtga ctgggtcatg gctgcgcccc    2160

gacacccgcc aacacccgct gacgcgccct gacgggcttg tctgctcccg gcatccgctt    2220

acagacaagc tgtgaccgtc tccgggagct gcatgtgtca gaggttttca ccgtcatcac    2280

cgaaacgcgc gaggcagctg cggtaaagct catcagcgtg gtcgtgaagc gattcacaga    2340

tgtctgcctg ttcatccgcg tccagctcgt tgagtttctc cagaagcgtt aatgtctggc    2400

ttctgataaa gcgggccatg ttaagggcgg ttttttcctg tttggtcact gatgcctccg    2460

tgtaaggggg atttctgttc atgggggtaa tgataccgat gaaacgagag aggatgctca    2520

cgatacgggt tactgatgat gaacatgccc ggttactgga acgttgtgag ggtaaacaac    2580

tggcggtatg gatgcggcgg gaccagagaa aaatcactca gggtcaatgc cagcgcttcg    2640

ttaatacaga tgtaggtgtt ccacagggta gccagcagca tcctgcgatg cagatccgga    2700

acataatggt gcagggcgct gacttccgcg tttccagact ttacgaaaca cggaaaccga    2760

agaccattca tgttgttgct caggtcgcag acgttttgca gcagcagtcg cttcacgttc    2820

gctcgcgtat cggtgattca ttctgctaac cagtaaggca accccgccag cctagccggg    2880

tcctcaacga caggagcacg atcatgcgca cccgtggcca ggacccaacg ctgcccgaga    2940

tctcgatccc gcgaaattaa tacgactcac tataggagag ccacaacggt ttccctctag    3000

aaataatttt gtttaacttt aagaaggaga tatacatatg ccgctcgaga acctgtattt    3060

ccaaggcggc atgggtgggc cgggcgtggg tgttccgggc gtaggtgtcc caggtgtggg    3120

cgtaccgggc gttggtgttc ctggtgtcgg cgtgccgggc gtgggtgttc cgggcgtagg    3180

tgtcccaggt gtgggcgtac cgggcgttgg tgttcctggt gtcggcgtgc cgggcgtggg    3240

tgttccgggc gtaggtgtcc caggtgtggg cgtaccgggc gttggtgttc ctggtgtcgg    3300

cgtgccgggc gtgggtgttc cgggcgtagg tgtcccaggt gtgggcgtac cgggcgttgg    3360

tgttcctggt gtcggcgtgc cgggcgtggg tgttccgggc gtaggtgtcc caggtgtggg    3420

cgtaccgggc gttggtgttc ctggtgtcgg cgtgccgggc gtgggtgttc cgggcgtagg    3480

tgtcccaggt gtgggcgtac cgggcgttgg tgttcctggt gtcggcgtgc cgggcgtggg    3540

tgttccgggc gtaggtgtcc caggtgtggg cgtaccgggc gttggtgttc ctggtgtcgg    3600

cgtgccgggc gtgggtgttc cgggcgtagg tgtcccaggt gtgggcgtac cgggcgttgg    3660

tgttcctggt gtcggcgtgc cgggcgtggg tgttccgggc gtaggtgtcc caggtgtggg    3720

cgtaccgggc gttggtgttc ctggtgtcgg cgtgccgggc gtgggtgttc cgggcgtagg    3780

tgtcccaggt gtgggcgtac cgggcgttgg tgttcctggt gtcggcgtgc cgggcgtggg    3840

tgttccgggc gtaggtgtcc caggtgtggg cgtaccgggc gttggtgttc ctggtgtcgg    3900

cgtgccgggc gtgggtgttc cgggcgtagg tgtcccaggt gtgggcgtac cgggcgttgg    3960

tgttcctggt gtcggcgtgc cgggctggcc ttgctgctga taagctagca tgactggtgg    4020

acagcaaatg ggtcgggatt caagcttggt accgagctcg gatccactag taacggccgc    4080

cagtgtgctg gaattctgca gatatccatc acactggcgg ccgctcgagc agatccggct    4140

gctaacaaag cccgaaagga agctgagttg gctgctgcca ccgctgagca ataactagca    4200

taaccccttg gggcctctaa acgggtcttg aggggttttt tgctgaaagg aggaactata    4260

tccggataa                                                            4269
```

<210> SEQ ID NO 58
<211> LENGTH: 51
<212> TYPE: DNA

-continued

<213> ORGANISM: Artificial Sequence
<220> FEATURE:
<223> OTHER INFORMATION: oligo

<400> SEQUENCE: 58
ctagaaataa ttttgtttaa ctttaagaag gagatatacc atgtgctgcc c 51

<210> SEQ ID NO 59
<211> LENGTH: 51
<212> TYPE: DNA
<213> ORGANISM: Artificial Sequence
<220> FEATURE:
<223> OTHER INFORMATION: oligo

<400> SEQUENCE: 59
catggggcag cacatggtat atctccttct taaagttaaa caaaattatt t 51

<210> SEQ ID NO 60
<211> LENGTH: 6
<212> TYPE: PRT
<213> ORGANISM: Artificial Sequence
<220> FEATURE:
<223> OTHER INFORMATION: Synthetic construct

<400> SEQUENCE: 60

Met Cys Cys Pro Met Gly
1               5

<210> SEQ ID NO 61
<211> LENGTH: 114
<212> TYPE: DNA
<213> ORGANISM: Artificial Sequence
<220> FEATURE:
<223> OTHER INFORMATION: annealed oligo

<400> SEQUENCE: 61
tctagaaata attttgttta actttaagaa ggagatatac catgtgctgc cccatggaga 60
tctttattaa aacaaattga aattcttcct ctatatggta cacgacgggg tacc 114

<210> SEQ ID NO 62
<211> LENGTH: 4664
<212> TYPE: DNA
<213> ORGANISM: Artificial Sequence
<220> FEATURE:
<223> OTHER INFORMATION: Synthetic construct

<400> SEQUENCE: 62
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660

-continued

```
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgt gctgccccat gggtgggccg   3060
```

-continued

```
ggcgtgggtg ttccgggcgt gggtgttccg ggtggcggtg tgccgggcgc aggtgttcct   3120
ggtgtaggtg tgccgggtgt tggtgtgccg ggtgttggtg taccaggtgg cggtgttccg   3180
ggtgcaggcg ttccgggtgg cggtgtgccg ggcgtgggtg ttccgggcgt gggtgttccg   3240
ggtggcggtg tgccgggcgc aggtgttcct ggtgtaggtg tgccgggtgt tggtgtgccg   3300
ggtgttggtg taccaggtgg cggtgttccg ggtgcaggcg ttccgggtgg cggtgtgccg   3360
ggcgtgggtg ttccgggcgt gggtgttccg ggtggcggtg tgccgggcgc aggtgttcct   3420
ggtgtaggtg tgccgggtgt tggtgtgccg ggtgttggtg taccaggtgg cggtgttccg   3480
ggtgcaggcg ttccgggtgg cggtgtgccg ggcgtgggtg ttccgggcgt gggtgttccg   3540
ggtggcggtg tgccgggcgc aggtgttcct ggtgtaggtg tgccgggtgt tggtgtgccg   3600
ggtgttggtg taccaggtgg cggtgttccg ggtgcaggcg ttccgggtgg cggtgtgccg   3660
ggcgtgggtg ttccgggcgt gggtgttccg ggtggcggtg tgccgggcgc aggtgttcct   3720
ggtgtaggtg tgccgggtgt tggtgtgccg ggtgttggtg taccaggtgg cggtgttccg   3780
ggtgcaggcg ttccgggtgg cggtgtgccg ggcgtgggtg ttccgggcgt gggtgttccg   3840
ggtggcggtg tgccgggcgc aggtgttcct ggtgtaggtg tgccgggtgt tggtgtgccg   3900
ggtgttggtg taccaggtgg cggtgttccg ggtgcaggcg ttccgggtgg cggtgtgccg   3960
ggcgtgggtg ttccgggcgt gggtgttccg ggtggcggtg tgccgggcgc aggtgttcct   4020
ggtgtaggtg tgccgggtgt tggtgtgccg ggtgttggtg taccaggtgg cggtgttccg   4080
ggtgcaggcg ttccgggtgg cggtgtgccg ggcgtgggtg ttccgggcgt gggtgttccg   4140
ggtggcggtg tgccgggcgc aggtgttcct ggtgtaggtg tgccgggtgt tggtgtgccg   4200
ggtgttggtg taccaggtgg cggtgttccg ggtgcaggcg ttccgggtgg cggtgtgccg   4260
ggcgtgggtg ttccgggcgt gggtgttccg ggtggcggtg tgccgggcgc aggtgttcct   4320
ggtgtaggtg tgccgggtgt tggtgtgccg ggtgttggtg taccaggtgg cggtgttccg   4380
ggtgcaggcg ttccgggtgg cggtgtgccg ggctggccga gcagcggtga ttacgatatc   4440
ccaacgaccg aaaacctgta ttttcagggc gcccatatgg gatccgaatt ctgcagatat   4500
ccatcacact ggcggccgct cgagcagatc cggctgctaa caaagcccga aaggaagctg   4560
agttggctgc tgccaccgct gagcaataac tagcataacc ccttggggcc tctaaacggg   4620
tcttgagggg ttttttgctg aaaggaggaa ctatatccgg ataa                    4664
```

<210> SEQ ID NO 63
<211> LENGTH: 4214
<212> TYPE: DNA
<213> ORGANISM: Artificial Sequence
<220> FEATURE:
<223> OTHER INFORMATION: Synthetic construct

<400> SEQUENCE: 63

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
```

-continued

```
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg    2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
```

-continued gctcgcgtat cggtgattca ttctgctaac cagtaaggca accccgccag cctagccggg 2880
tcctcaacga caggagcacg atcatgcgca cccgtggcca ggacccaacg ctgcccgaga 2940
tctcgatccc gcgaaattaa tacgactcac tatagggaga ccacaacggt ttccctctag 3000
aaataatttt gtttaacttt aagaaggaga tataccatgt gctgccccat gggtgggccg 3060
ggcgtgggtg ttccgggcgt aggtgtccca ggtgtgggcg taccgggcgt tggtgttcct 3120
ggtgtcggcg tgccgggcgt gggtgttccg ggcgtaggtg tcccaggtgt gggcgtaccg 3180
ggcgttggtg ttcctggtgt cggcgtgccg ggcgtgggtg ttccgggcgt aggtgtccca 3240
ggtgtgggcg taccgggcgt tggtgttcct ggtgtcggcg tgccgggcgt gggtgttccg 3300
ggcgtaggtg tcccaggtgt gggcgtaccg ggcgttggtg ttcctggtgt cggcgtgccg 3360
ggcgtgggtg ttccgggcgt aggtgtccca ggtgtgggcg taccgggcgt tggtgttcct 3420
ggtgtcggcg tgccgggcgt gggtgttccg ggcgtaggtg tcccaggtgt gggcgtaccg 3480
ggcgttggtg ttcctggtgt cggcgtgccg ggcgtgggtg ttccgggcgt aggtgtccca 3540
ggtgtgggcg taccgggcgt tggtgttcct ggtgtcggcg tgccgggcgt gggtgttccg 3600
ggcgtaggtg tcccaggtgt gggcgtaccg ggcgttggtg ttcctggtgt cggcgtgccg 3660
ggcgtgggtg ttccgggcgt aggtgtccca ggtgtgggcg taccgggcgt tggtgttcct 3720
ggtgtcggcg tgccgggcgt gggtgttccg ggcgtaggtg tcccaggtgt gggcgtaccg 3780
ggcgttggtg ttcctggtgt cggcgtgccg ggcgtgggtg ttccgggcgt aggtgtccca 3840
ggtgtgggcg taccgggcgt tggtgttcct ggtgtcggcg tgccgggcgt gggtgttccg 3900
ggcgtaggtg tcccaggtgt gggcgtaccg ggcgttggtg ttcctggtgt cggcgtgccg 3960
ggctggccga gcagcggtga ttacgatatc ccaacgaccg aaaacctgta ttttcagggc 4020
gcccatatgg gatccgaatt ctgcagatat ccatcacact ggcggccgct cgagcagatc 4080
cggctgctaa caaagcccga aaggaagctg agttggctgc tgccaccgct gagcaataac 4140
tagcataacc ccttggggcc tctaaacggg tcttgagggg ttttttgctg aaaggaggaa 4200
ctatatccgg ataa 4214

<210> SEQ ID NO 64
<211> LENGTH: 24
<212> TYPE: DNA
<213> ORGANISM: Artificial Sequence
<220> FEATURE:
<223> OTHER INFORMATION: oligo

<400> SEQUENCE: 64
tggccgtgct gcagcagcgg tgat 24

<210> SEQ ID NO 65
<211> LENGTH: 27
<212> TYPE: DNA
<213> ORGANISM: Artificial Sequence
<220> FEATURE:
<223> OTHER INFORMATION: oligo

<400> SEQUENCE: 65
atcaccgctg ctgcagcacg gccagcc 27

<210> SEQ ID NO 66
<211> LENGTH: 11
<212> TYPE: PRT
<213> ORGANISM: Artificial Sequence
<220> FEATURE:

-continued

<223> OTHER INFORMATION: Synthetic construct

<400> SEQUENCE: 66

Pro Gly Trp Pro Cys Cys Ser Ser Gly Asp Ile
1               5                   10

<210> SEQ ID NO 67
<211> LENGTH: 68
<212> TYPE: DNA
<213> ORGANISM: Artificial Sequence
<220> FEATURE:
<223> OTHER INFORMATION: annealed oligos

<400> SEQUENCE: 67
gccgggctgg ccgtgctgca gcagcggtga tatccggccc gaccggcacg acgtcgtcgc 60
cactatag 68

<210> SEQ ID NO 68
<211> LENGTH: 4652
<212> TYPE: DNA
<213> ORGANISM: Artificial Sequence
<220> FEATURE:
<223> OTHER INFORMATION: Synthetic construct

<400> SEQUENCE: 68
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020
aaatagacag atcgctgaga taggtgcctc actgattaag cattggtaac tgtcagacca 1080
agtttactca tatatacttt agattgattt aaaacttcat ttttaattta aaaggatcta 1140
ggtgaagatc ctttttgata atctcatgac caaaatccct taacgtgagt tttcgttcca 1200
ctgagcgtca gaccccgtag aaaagatcaa aggatcttct tgagatcctt tttttctgcg 1260
cgtaatctgc tgcttgcaaa caaaaaaacc accgctacca gcggtggttt gtttgccgga 1320
tcaagagcta ccaactcttt ttccgaaggt aactggcttc agcagagcgc agataccaaa 1380
tactgtcctt ctagtgtagc cgtagttagg ccaccacttc aagaactctg tagcaccgcc 1440

-continued

```
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgg gtgggccggg cgtgggtgtt   3060
ccgggcgtgg gtgttccggg tggcggtgtg ccgggcgcag gtgttcctgg tgtaggtgtg   3120
ccgggtgttg gtgtgccggg tgttggtgta ccaggtggcg gtgttccggg tgcaggcgtt   3180
ccgggtggcg gtgtgccggg cgtgggtgtt ccgggcgtgg gtgttccggg tggcggtgtg   3240
ccgggcgcag gtgttcctgg tgtaggtgtg ccgggtgttg gtgtgccggg tgttggtgta   3300
ccaggtggcg gtgttccggg tgcaggcgtt ccgggtggcg gtgtgccggg cgtgggtgtt   3360
ccgggcgtgg gtgttccggg tggcggtgtg ccgggcgcag gtgttcctgg tgtaggtgtg   3420
ccgggtgttg gtgtgccggg tgttggtgta ccaggtggcg gtgttccggg tgcaggcgtt   3480
ccgggtggcg gtgtgccggg cgtgggtgtt ccgggcgtgg gtgttccggg tggcggtgtg   3540
ccgggcgcag gtgttcctgg tgtaggtgtg ccgggtgttg gtgtgccggg tgttggtgta   3600
ccaggtggcg gtgttccggg tgcaggcgtt ccgggtggcg gtgtgccggg cgtgggtgtt   3660
ccgggcgtgg gtgttccggg tggcggtgtg ccgggcgcag gtgttcctgg tgtaggtgtg   3720
ccgggtgttg gtgtgccggg tgttggtgta ccaggtggcg gtgttccggg tgcaggcgtt   3780
ccgggtggcg gtgtgccggg cgtgggtgtt ccgggcgtgg gtgttccggg tggcggtgtg   3840
```

-continued

```
ccgggcgcag gtgttcctgg tgtaggtgtg ccgggtgttg gtgtgccggg tgttggtgta   3900

ccaggtggcg gtgttccggg tgcaggcgtt ccgggtggcg gtgtgccggg cgtgggtgtt   3960

ccgggcgtgg gtgttccggg tggcggtgtg ccgggcgcag gtgttcctgg tgtaggtgtg   4020

ccgggtgttg gtgtgccggg tgttggtgta ccaggtggcg gtgttccggg tgcaggcgtt   4080

ccgggtggcg gtgtgccggg cgtgggtgtt ccgggcgtgg gtgttccggg tggcggtgtg   4140

ccgggcgcag gtgttcctgg tgtaggtgtg ccgggtgttg gtgtgccggg tgttggtgta   4200

ccaggtggcg gtgttccggg tgcaggcgtt ccgggtggcg gtgtgccggg cgtgggtgtt   4260

ccgggcgtgg gtgttccggg tggcggtgtg ccgggcgcag gtgttcctgg tgtaggtgtg   4320

ccgggtgttg gtgtgccggg tgttggtgta ccaggtggcg gtgttccggg tgcaggcgtt   4380

ccgggtggcg gtgtgccggg ctggccgtgc tgcagcagcg gtgatatccc aacgaccgaa   4440

aacctgtatt ttcagggcgc ccatatggga tccgaattct gcagatatcc atcacactgg   4500

cggccgctcg agcagatccg gctgctaaca aagcccgaaa ggaagctgag ttggctgctg   4560

ccaccgctga gcaataacta gcataacccc ttggggcctc taaacgggtc ttgaggggtt   4620

ttttgctgaa aggaggaact atatccggat aa                                 4652
```

<210> SEQ ID NO 69
<211> LENGTH: 4202
<212> TYPE: DNA
<213> ORGANISM: Artificial Sequence
<220> FEATURE:
<223> OTHER INFORMATION: Synthetic construct

<400> SEQUENCE: 69

```
ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtat gagtattcaa catttccgtg tcgcccttat    240

tccctttttt gcggcatttt gccttcctgt ttttgctcac ccagaaacgc tggtgaaagt    300

aaaagatgct gaagatcagt tgggtgcacg agtgggttac atcgaactgg atctcaacag    360

cggtaagatc cttgagagtt ttcgccccga agaacgtttt ccaatgatga gcacttttaa    420

agttctgcta tgtggcgcgg tattatcccg tgttgacgcc gggcaagagc aactcggtcg    480

ccgcatacac tattctcaga atgacttggt tgagtactca ccagtcacag aaaagcatct    540

tacggatggc atgacagtaa gagaattatg cagtgctgcc ataaccatga gtgataacac    600

tgcggccaac ttacttctga caacgatcgg aggaccgaag gagctaaccg cttttttgca    660

caacatgggg gatcatgtaa ctcgccttga tcgttgggaa ccggagctga atgaagccat    720

accaaacgac gagcgtgaca ccacgatgcc tgcagcaatg gcaacaacgt tgcgcaaact    780

attaactggc gaactactta ctctagcttc ccggcaacaa ttaatagact ggatggaggc    840

ggataaagtt gcaggaccac ttctgcgctc ggcccttccg gctggctggt ttattgctga    900

taaatctgga gccggtgagc gtgggtctcg cggtatcatt gcagcactgg ggccagatgg    960

taagccctcc cgtatcgtag ttatctacac gacggggagt caggcaacta tggatgaacg   1020

aaatagacag atcgctgaga taggtgcctc actgattaag cattggtaac tgtcagacca   1080

agtttactca tatatacttt agattgattt aaaacttcat ttttaattta aaaggatcta   1140

ggtgaagatc ctttttgata atctcatgac caaaatccct taacgtgagt tttcgttcca   1200
```

-continued

```
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tctcgatccc gcgaaattaa tacgactcac tatagggaga ccacaacggt ttccctctag   3000
aaataatttt gtttaacttt aagaaggaga tataccatgg gtgggccggg cgtgggtgtt   3060
ccgggcgtag gtgtcccagg tgtgggcgta ccgggcgttg gtgttcctgg tgtcggcgtg   3120
ccgggcgtgg gtgttccggg cgtaggtgtc ccaggtgtgg gcgtaccggg cgttggtgtt   3180
cctggtgtcg gcgtgccggg cgtgggtgtt ccgggcgtag gtgtcccagg tgtgggcgta   3240
ccgggcgttg gtgttcctgg tgtcggcgtg ccgggcgtgg gtgttccggg cgtaggtgtc   3300
ccaggtgtgg gcgtaccggg cgttggtgtt cctggtgtcg gcgtgccggg cgtgggtgtt   3360
ccgggcgtag gtgtcccagg tgtgggcgta ccgggcgttg gtgttcctgg tgtcggcgtg   3420
ccgggcgtgg gtgttccggg cgtaggtgtc ccaggtgtgg gcgtaccggg cgttggtgtt   3480
cctggtgtcg gcgtgccggg cgtgggtgtt ccgggcgtag gtgtcccagg tgtgggcgta   3540
ccgggcgttg gtgttcctgg tgtcggcgtg ccgggcgtgg gtgttccggg cgtaggtgtc   3600
```

-continued

```
ccaggtgtgg gcgtaccggg cgttggtgtt cctggtgtcg gcgtgccggg cgtgggtgtt   3660

ccgggcgtag gtgtcccagg tgtgggcgta ccgggcgttg gtgttcctgg tgtcggcgtg   3720

ccgggcgtgg gtgttccggg cgtaggtgtc ccaggtgtgg gcgtaccggg cgttggtgtt   3780

cctggtgtcg gcgtgccggg cgtgggtgtt ccgggcgtag gtgtcccagg tgtgggcgta   3840

ccgggcgttg gtgttcctgg tgtcggcgtg ccgggcgtgg gtgttccggg cgtaggtgtc   3900

ccaggtgtgg gcgtaccggg cgttggtgtt cctggtgtcg gcgtgccggg ctggccgtgc   3960

tgcagcagcg gtgatatccc aacgaccgaa aacctgtatt ttcagggcgc ccatatggga   4020

tccgaattct gcagatatcc atcacactgg cggccgctcg agcagatccg gctgctaaca   4080

aagcccgaaa ggaagctgag ttggctgctg ccaccgctga gcaataacta gcataacccc   4140

ttggggcctc taaacgggtc ttgaggggtt ttttgctgaa aggaggaact atatccggat   4200

aa                                                                  4202
```

<210> SEQ ID NO 70
<211> LENGTH: 510
<212> TYPE: DNA
<213> ORGANISM: Artificial Sequence
<220> FEATURE:
<223> OTHER INFORMATION: Synthetic construct

<400> SEQUENCE: 70

```
catatgtgtg atctgcctca aacccacagc ctgggtagca ggaggacctt gatgctcctg     60

gcacagatga ggagaatctc tcttttctcc tgcttgaagg acagacatga ctttggattt    120

ccccaggagg agtttggcaa ccagttccaa aaggctgaaa ccatccctgt cctccatgag    180

atgatccagc agatcttcaa tctcttcagc acaaaggact catctgctgc ttgggatgag    240

accctcctag acaaattcta cactgaactc taccagcagc tgaatgacct ggaagcctgt    300

gtgatacagg gggtgggggt gacagagact cccctgatga aggaggactc cattctggct    360

gtgaggaaat acttccaaag aatcactctc tatctgaaag agaagaaata cagcccttgt    420

gcctgggagg ttgtcagagc agaaatcatg agatcttttt ctttgtcaac aaacttgcaa    480

gaaagtttaa gaagtaagga ataactcgag                                     510
```

<210> SEQ ID NO 71
<211> LENGTH: 507
<212> TYPE: DNA
<213> ORGANISM: Artificial Sequence
<220> FEATURE:
<223> OTHER INFORMATION: Synthetic construct

<400> SEQUENCE: 71

```
catatgtgtg atctgcctca aacccacagc ctgggtagca ggaggacctt gatgctcctg     60

gcacagatga ggagaatctc tcttttctcc tgcttgaagg acagacatga ctttggattt    120

ccccaggagg agtttggcaa ccagttccaa aaggctgaaa ccatccctgt cctccatgag    180

atgatccagc agatcttcaa tctcttcagc acaaaggact catctgctgc ttgggatgag    240

accctcctag acaaattcta cactgaactc taccagcagc tgaatgacct ggaagcctgt    300

gtgatacagg gggtgggggt gacagagact cccctgatga aggaggactc cattctggct    360

gtgaggaaat acttccaaag aatcactctc tatctgaaag agaagaaata cagcccttgt    420

gcctgggagg ttgtcagagc agaaatcatg agatcttttt ctttgtcaac aaacttgcaa    480

gaaagtttaa gaagtaagga actcgag                                        507
```

-continued

<210> SEQ ID NO 72
<211> LENGTH: 169
<212> TYPE: PRT
<213> ORGANISM: Artificial Sequence
<220> FEATURE:
<223> OTHER INFORMATION: Synthetic construct

<400> SEQUENCE: 72

```
Gly Ala His Met Cys Asp Leu Pro Gln Thr His Ser Leu Gly Ser Arg
1               5                   10                  15

Arg Thr Leu Met Leu Leu Ala Gln Met Arg Arg Ile Ser Leu Phe Ser
            20                  25                  30

Cys Leu Lys Asp Arg His Asp Phe Gly Phe Pro Gln Glu Glu Phe Gly
        35                  40                  45

Asn Gln Phe Gln Lys Ala Glu Thr Ile Pro Val Leu His Glu Met Ile
    50                  55                  60

Gln Gln Ile Phe Asn Leu Phe Ser Thr Lys Asp Ser Ser Ala Ala Trp
65                  70                  75                  80

Asp Glu Thr Leu Leu Asp Lys Phe Tyr Thr Glu Leu Tyr Gln Gln Leu
                85                  90                  95

Asn Asp Leu Glu Ala Cys Val Ile Gln Gly Val Gly Val Thr Glu Thr
            100                 105                 110

Pro Leu Met Lys Glu Asp Ser Ile Leu Ala Val Arg Lys Tyr Phe Gln
        115                 120                 125

Arg Ile Thr Leu Tyr Leu Lys Glu Lys Lys Tyr Ser Pro Cys Ala Trp
    130                 135                 140

Glu Val Val Arg Ala Glu Ile Met Arg Ser Phe Ser Leu Ser Thr Asn
145                 150                 155                 160

Leu Gln Glu Ser Leu Arg Ser Lys Glu
                165
```

<210> SEQ ID NO 73
<211> LENGTH: 169
<212> TYPE: PRT
<213> ORGANISM: Artificial Sequence
<220> FEATURE:
<223> OTHER INFORMATION: Synthetic construct

<400> SEQUENCE: 73

```
Gly Ala His Met Cys Asp Leu Pro Gln Thr His Ser Leu Gly Ser Arg
1               5                   10                  15

Arg Thr Leu Met Leu Leu Ala Gln Met Arg Arg Ile Ser Leu Phe Ser
            20                  25                  30

Cys Leu Lys Asp Arg His Asp Phe Gly Phe Pro Gln Glu Glu Phe Gly
        35                  40                  45

Asn Gln Phe Gln Lys Ala Glu Thr Ile Pro Val Leu His Glu Met Ile
    50                  55                  60

Gln Gln Ile Phe Asn Leu Phe Ser Thr Lys Asp Ser Ser Ala Ala Trp
65                  70                  75                  80

Asp Glu Thr Leu Leu Asp Lys Phe Tyr Thr Glu Leu Tyr Gln Gln Leu
                85                  90                  95

Asn Asp Leu Glu Ala Cys Val Ile Gln Gly Val Gly Val Thr Glu Thr
            100                 105                 110

Pro Leu Met Lys Glu Asp Ser Ile Leu Ala Val Arg Lys Tyr Phe Gln
        115                 120                 125

Arg Ile Thr Leu Tyr Leu Lys Glu Lys Lys Tyr Ser Pro Cys Ala Trp
    130                 135                 140
```

-continued

Glu Val Val Arg Ala Glu Ile Met Arg Ser Phe Ser Leu Ser Thr Asn
145 150 155 160

Leu Gln Glu Ser Leu Arg Ser Lys Glu
165

<210> SEQ ID NO 74
<211> LENGTH: 169
<212> TYPE: PRT
<213> ORGANISM: Artificial Sequence
<220> FEATURE:
<223> OTHER INFORMATION: Synthetic construct

<400> SEQUENCE: 74

Gly Ala His Met Cys Asp Leu Pro Gln Thr His Ser Leu Gly Ser Arg
1 5 10 15

Arg Thr Leu Met Leu Leu Ala Gln Met Arg Arg Ile Ser Leu Phe Ser
20 25 30

Cys Leu Lys Asp Arg His Asp Phe Gly Phe Pro Gln Glu Glu Phe Gly
35 40 45

Asn Gln Phe Gln Lys Ala Glu Thr Ile Pro Val Leu His Glu Met Ile
50 55 60

Gln Gln Ile Phe Asn Leu Phe Ser Thr Lys Asp Ser Ser Ala Ala Trp
65 70 75 80

Asp Glu Thr Leu Leu Asp Lys Phe Tyr Thr Glu Leu Tyr Gln Gln Leu
85 90 95

Asn Asp Leu Glu Ala Cys Val Ile Gln Gly Val Gly Val Thr Glu Thr
100 105 110

Pro Leu Met Lys Glu Asp Ser Ile Leu Ala Val Arg Lys Tyr Phe Gln
115 120 125

Arg Ile Thr Leu Tyr Leu Lys Glu Lys Lys Tyr Ser Pro Cys Ala Trp
130 135 140

Glu Val Val Arg Ala Glu Ile Met Arg Ser Phe Ser Leu Ser Thr Asn
145 150 155 160

Leu Gln Glu Ser Leu Arg Ser Lys Glu
165

<210> SEQ ID NO 75
<211> LENGTH: 169
<212> TYPE: PRT
<213> ORGANISM: Artificial Sequence
<220> FEATURE:
<223> OTHER INFORMATION: Synthetic construct

<400> SEQUENCE: 75

Gly Ala His Met Cys Asp Leu Pro Gln Thr His Ser Leu Gly Ser Arg
1 5 10 15

Arg Thr Leu Met Leu Leu Ala Gln Met Arg Arg Ile Ser Leu Phe Ser
20 25 30

Cys Leu Lys Asp Arg His Asp Phe Gly Phe Pro Gln Glu Glu Phe Gly
35 40 45

Asn Gln Phe Gln Lys Ala Glu Thr Ile Pro Val Leu His Glu Met Ile
50 55 60

Gln Gln Ile Phe Asn Leu Phe Ser Thr Lys Asp Ser Ser Ala Ala Trp
65 70 75 80

Asp Glu Thr Leu Leu Asp Lys Phe Tyr Thr Glu Leu Tyr Gln Gln Leu
85 90 95

Asn Asp Leu Glu Ala Cys Val Ile Gln Gly Val Gly Val Thr Glu Thr

-continued

```
            100                 105                 110

Pro Leu Met Lys Glu Asp Ser Ile Leu Ala Val Arg Lys Tyr Phe Gln
        115                 120                 125

Arg Ile Thr Leu Tyr Leu Lys Glu Lys Lys Tyr Ser Pro Cys Ala Trp
    130                 135                 140

Glu Val Val Arg Ala Glu Ile Met Arg Ser Phe Ser Leu Ser Thr Asn
145                 150                 155                 160

Leu Gln Glu Ser Leu Arg Ser Lys Glu
                165


<210> SEQ ID NO 76
<211> LENGTH: 169
<212> TYPE: PRT
<213> ORGANISM: Artificial Sequence
<220> FEATURE:
<223> OTHER INFORMATION: Synthetic construct

<400> SEQUENCE: 76

Gly Ala His Met Cys Asp Leu Pro Gln Thr His Ser Leu Gly Ser Arg
1               5                   10                  15

Arg Thr Leu Met Leu Leu Ala Gln Met Arg Arg Ile Ser Leu Phe Ser
            20                  25                  30

Cys Leu Lys Asp Arg His Asp Phe Gly Phe Pro Gln Glu Glu Phe Gly
        35                  40                  45

Asn Gln Phe Gln Lys Ala Glu Thr Ile Pro Val Leu His Glu Met Ile
    50                  55                  60

Gln Gln Ile Phe Asn Leu Phe Ser Thr Lys Asp Ser Ser Ala Ala Trp
65                  70                  75                  80

Asp Glu Thr Leu Leu Asp Lys Phe Tyr Thr Glu Leu Tyr Gln Gln Leu
                85                  90                  95

Asn Asp Leu Glu Ala Cys Val Ile Gln Gly Val Gly Val Thr Glu Thr
            100                 105                 110

Pro Leu Met Lys Glu Asp Ser Ile Leu Ala Val Arg Lys Tyr Phe Gln
        115                 120                 125

Arg Ile Thr Leu Tyr Leu Lys Glu Lys Lys Tyr Ser Pro Cys Ala Trp
    130                 135                 140

Glu Val Val Arg Ala Glu Ile Met Arg Ser Phe Ser Leu Ser Thr Asn
145                 150                 155                 160

Leu Gln Glu Ser Leu Arg Ser Lys Glu
                165


<210> SEQ ID NO 77
<211> LENGTH: 169
<212> TYPE: PRT
<213> ORGANISM: Artificial Sequence
<220> FEATURE:
<223> OTHER INFORMATION: Synthetic construct

<400> SEQUENCE: 77

Gly Ala His Met Cys Asp Leu Pro Gln Thr His Ser Leu Gly Ser Arg
1               5                   10                  15

Arg Thr Leu Met Leu Leu Ala Gln Met Arg Arg Ile Ser Leu Phe Ser
            20                  25                  30

Cys Leu Lys Asp Arg His Asp Phe Gly Phe Pro Gln Glu Glu Phe Gly
        35                  40                  45

Asn Gln Phe Gln Lys Ala Glu Thr Ile Pro Val Leu His Glu Met Ile
    50                  55                  60
```

-continued

```
Gln Gln Ile Phe Asn Leu Phe Ser Thr Lys Asp Ser Ser Ala Ala Trp
65                  70                  75                  80

Asp Glu Thr Leu Leu Asp Lys Phe Tyr Thr Glu Leu Tyr Gln Gln Leu
                85                  90                  95

Asn Asp Leu Glu Ala Cys Val Ile Gln Gly Val Gly Val Thr Glu Thr
            100                 105                 110

Pro Leu Met Lys Glu Asp Ser Ile Leu Ala Val Arg Lys Tyr Phe Gln
        115                 120                 125

Arg Ile Thr Leu Tyr Leu Lys Glu Lys Lys Tyr Ser Pro Cys Ala Trp
    130                 135                 140

Glu Val Val Arg Ala Glu Ile Met Arg Ser Phe Ser Leu Ser Thr Asn
145                 150                 155                 160

Leu Gln Glu Ser Leu Arg Ser Lys Glu
                165
```

<210> SEQ ID NO 78
<211> LENGTH: 173
<212> TYPE: PRT
<213> ORGANISM: Artificial Sequence
<220> FEATURE:
<223> OTHER INFORMATION: Synthetic construct

<400> SEQUENCE: 78

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170
```

<210> SEQ ID NO 79
<211> LENGTH: 173
<212> TYPE: PRT
<213> ORGANISM: Artificial Sequence
<220> FEATURE:
<223> OTHER INFORMATION: Synthetic construct

<400> SEQUENCE: 79

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30
```

-continued

```
Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170


<210> SEQ ID NO 80
<211> LENGTH: 173
<212> TYPE: PRT
<213> ORGANISM: Artificial Sequence
<220> FEATURE:
<223> OTHER INFORMATION: Synthetic construct

<400> SEQUENCE: 80

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170


<210> SEQ ID NO 81
<211> LENGTH: 173
<212> TYPE: PRT
<213> ORGANISM: Artificial Sequence
<220> FEATURE:
<223> OTHER INFORMATION: Synthetic construct
```

-continued

<400> SEQUENCE: 81

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170
```

<210> SEQ ID NO 82
<211> LENGTH: 173
<212> TYPE: PRT
<213> ORGANISM: Artificial Sequence
<220> FEATURE:
<223> OTHER INFORMATION: Synthetic construct

<400> SEQUENCE: 82

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170
```

-continued

<210> SEQ ID NO 83
<211> LENGTH: 173
<212> TYPE: PRT
<213> ORGANISM: Artificial Sequence
<220> FEATURE:
<223> OTHER INFORMATION: Synthetic construct

<400> SEQUENCE: 83

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu Leu Glu Asn Leu Tyr Phe Gln
                165                 170
```

<210> SEQ ID NO 84
<211> LENGTH: 451
<212> TYPE: PRT
<213> ORGANISM: Artificial Sequence
<220> FEATURE:
<223> OTHER INFORMATION: Synthetic construct
<220> FEATURE:
<221> NAME/KEY: REPEAT
<222> LOCATION: (2)..(451)
<220> FEATURE:
<221> NAME/KEY: REPEAT
<222> LOCATION: (2)..(451)
<223> OTHER INFORMATION: ELP1 [V5G3A2-90]

<400> SEQUENCE: 84

```
Gly Val Gly Val Pro Gly Val Gly Val Pro Gly Gly Gly Val Pro Gly
1               5                   10                  15

Ala Gly Val Pro Gly Val Gly Val Pro Gly Val Gly Val Pro Gly Val
            20                  25                  30

Gly Val Pro Gly Gly Gly Val Pro Gly Ala Gly Val Pro Gly Gly Gly
        35                  40                  45

Val Pro Gly Val Gly Val Pro Gly Val Gly Val Pro Gly Gly Gly Val
    50                  55                  60

Pro Gly Ala Gly Val Pro Gly Val Gly Val Pro Gly Val Gly Val Pro
65                  70                  75                  80

Gly Val Gly Val Pro Gly Gly Gly Val Pro Gly Ala Gly Val Pro Gly
                85                  90                  95

Gly Gly Val Pro Gly Val Gly Val Pro Gly Val Gly Val Pro Gly Gly
            100                 105                 110
```

-continued

```
Gly Val Pro Gly Ala Gly Val Pro Gly Val Gly Val Pro Gly Val Gly
        115                 120                 125

Val Pro Gly Val Gly Val Pro Gly Gly Gly Val Pro Gly Ala Gly Val
    130                 135                 140

Pro Gly Gly Gly Val Pro Gly Val Gly Val Pro Gly Val Gly Val Pro
145                 150                 155                 160

Gly Gly Gly Val Pro Gly Ala Gly Val Pro Gly Val Gly Val Pro Gly
                165                 170                 175

Val Gly Val Pro Gly Val Gly Val Pro Gly Gly Gly Val Pro Gly Ala
            180                 185                 190

Gly Val Pro Gly Gly Gly Val Pro Gly Val Gly Val Pro Gly Val Gly
        195                 200                 205

Val Pro Gly Gly Gly Val Pro Gly Ala Gly Val Pro Gly Val Gly Val
    210                 215                 220

Pro Gly Val Gly Val Pro Gly Val Gly Val Pro Gly Gly Gly Val Pro
225                 230                 235                 240

Gly Ala Gly Val Pro Gly Gly Gly Val Pro Gly Val Gly Val Pro Gly
                245                 250                 255

Val Gly Val Pro Gly Gly Gly Val Pro Gly Ala Gly Val Pro Gly Val
            260                 265                 270

Gly Val Pro Gly Val Gly Val Pro Gly Val Gly Val Pro Gly Gly Gly
        275                 280                 285

Val Pro Gly Ala Gly Val Pro Gly Gly Gly Val Pro Gly Val Gly Val
    290                 295                 300

Pro Gly Val Gly Val Pro Gly Gly Gly Val Pro Gly Ala Gly Val Pro
305                 310                 315                 320

Gly Val Gly Val Pro Gly Val Gly Val Pro Gly Val Gly Val Pro Gly
                325                 330                 335

Gly Gly Val Pro Gly Ala Gly Val Pro Gly Gly Gly Val Pro Gly Val
            340                 345                 350

Gly Val Pro Gly Val Gly Val Pro Gly Gly Gly Val Pro Gly Ala Gly
        355                 360                 365

Val Pro Gly Val Gly Val Pro Gly Val Gly Val Pro Gly Val Gly Val
    370                 375                 380

Pro Gly Gly Gly Val Pro Gly Ala Gly Val Pro Gly Gly Gly Val Pro
385                 390                 395                 400

Gly Val Gly Val Pro Gly Val Gly Val Pro Gly Gly Gly Val Pro Gly
                405                 410                 415

Ala Gly Val Pro Gly Val Gly Val Pro Gly Val Gly Val Pro Gly Val
            420                 425                 430

Gly Val Pro Gly Gly Gly Val Pro Gly Ala Gly Val Pro Gly Gly Gly
        435                 440                 445

Val Pro Gly
    450
```

<210> SEQ ID NO 85
<211> LENGTH: 1353
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1353)
<223> OTHER INFORMATION: ELP1-90

-continued

<400> SEQUENCE: 85

```
ggcgtgggtg ttccgggcgt gggtgttccg ggtggcggtg tgccgggcgc aggtgttcct     60

ggtgtaggtg tgccgggtgt tggtgtgccg ggtgttggtg taccaggtgg cggtgttccg    120

ggtgcaggcg ttccgggtgg cggtgtgccg ggcgtgggtg ttccgggcgt gggtgttccg    180

ggtggcggtg tgccgggcgc aggtgttcct ggtgtaggtg tgccgggtgt tggtgtgccg    240

ggtgttggtg taccaggtgg cggtgttccg ggtgcaggcg ttccgggtgg cggtgtgccg    300

ggcgtgggtg ttccgggcgt gggtgttccg ggtggcggtg tgccgggcgc aggtgttcct    360

ggtgtaggtg tgccgggtgt tggtgtgccg ggtgttggtg taccaggtgg cggtgttccg    420

ggtgcaggcg ttccgggtgg cggtgtgccg ggcgtgggtg ttccgggcgt gggtgttccg    480

ggtggcggtg tgccgggcgc aggtgttcct ggtgtaggtg tgccgggtgt tggtgtgccg    540

ggtgttggtg taccaggtgg cggtgttccg ggtgcaggcg ttccgggtgg cggtgtgccg    600

ggcgtgggtg ttccgggcgt gggtgttccg ggtggcggtg tgccgggcgc aggtgttcct    660

ggtgtaggtg tgccgggtgt tggtgtgccg ggtgttggtg taccaggtgg cggtgttccg    720

ggtgcaggcg ttccgggtgg cggtgtgccg ggcgtgggtg ttccgggcgt gggtgttccg    780

ggtggcggtg tgccgggcgc aggtgttcct ggtgtaggtg tgccgggtgt tggtgtgccg    840

ggtgttggtg taccaggtgg cggtgttccg ggtgcaggcg ttccgggtgg cggtgtgccg    900

ggcgtgggtg ttccgggcgt gggtgttccg ggtggcggtg tgccgggcgc aggtgttcct    960

ggtgtaggtg tgccgggtgt tggtgtgccg ggtgttggtg taccaggtgg cggtgttccg   1020

ggtgcaggcg ttccgggtgg cggtgtgccg ggcgtgggtg ttccgggcgt gggtgttccg   1080

ggtggcggtg tgccgggcgc aggtgttcct ggtgtaggtg tgccgggtgt tggtgtgccg   1140

ggtgttggtg taccaggtgg cggtgttccg ggtgcaggcg ttccgggtgg cggtgtgccg   1200

ggcgtgggtg ttccgggcgt gggtgttccg ggtggcggtg tgccgggcgc aggtgttcct   1260

ggtgtaggtg tgccgggtgt tggtgtgccg ggtgttggtg taccaggtgg cggtgttccg   1320

ggtgcaggcg ttccgggtgg cggtgtgccg ggc                                1353
```

<210> SEQ ID NO 86
<211> LENGTH: 301
<212> TYPE: PRT
<213> ORGANISM: Artificial Sequence
<220> FEATURE:
<223> OTHER INFORMATION: Synthetic construct
<220> FEATURE:
<221> NAME/KEY: REPEAT
<222> LOCATION: (2)..(300)
<223> OTHER INFORMATION: ELP4-60

<400> SEQUENCE: 86

```
Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95
```

-continued

```
Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285

Val Pro Gly Val Gly Val Pro Gly Val Gly Val Pro Gly
    290                 295                 300
```

<210> SEQ ID NO 87
<211> LENGTH: 903
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(903)
<223> OTHER INFORMATION: ELP4-60

<400> SEQUENCE: 87

```
ggcgtgggtg ttccgggcgt aggtgtccca ggtgtgggcg taccgggcgt tggtgttcct      60

ggtgtcggcg tgccgggcgt gggtgttccg ggcgtaggtg tcccaggtgt gggcgtaccg     120

ggcgttggtg ttcctggtgt cggcgtgccg ggcgtgggtg ttccgggcgt aggtgtccca     180

ggtgtgggcg taccgggcgt tggtgttcct ggtgtcggcg tgccgggcgt gggtgttccg     240

ggcgtaggtg tcccaggtgt gggcgtaccg ggcgttggtg ttcctggtgt cggcgtgccg     300

ggcgtgggtg ttccgggcgt aggtgtccca ggtgtgggcg taccgggcgt tggtgttcct     360

ggtgtcggcg tgccgggcgt gggtgttccg ggcgtaggtg tcccaggtgt gggcgtaccg     420

ggcgttggtg ttcctggtgt cggcgtgccg ggcgtgggtg ttccgggcgt aggtgtccca     480

ggtgtgggcg taccgggcgt tggtgttcct ggtgtcggcg tgccgggcgt gggtgttccg     540

ggcgtaggtg tcccaggtgt gggcgtaccg ggcgttggtg ttcctggtgt cggcgtgccg     600

ggcgtgggtg ttccgggcgt aggtgtccca ggtgtgggcg taccgggcgt tggtgttcct     660

ggtgtcggcg tgccgggcgt gggtgttccg ggcgtaggtg tcccaggtgt gggcgtaccg     720

ggcgttggtg ttcctggtgt cggcgtgccg ggcgtgggtg ttccgggcgt aggtgtccca     780
```

-continued

```
ggtgtgggcg taccgggcgt tggtgttcct ggtgtcggcg tgccgggcgt gggtgttccg    840

ggcgtaggtg tcccaggtgt gggcgtaccg ggcgttggtg ttcctggtgt cggcgtgccg    900

ggc                                                                  903
```

MULTIMERIC ELP FUSION CONSTRUCTS

CROSS-REFERENCE TO RELATED APPLICATION

The benefit of priority U.S. Provisional Patent Application 60/756,269 filed Jan. 4, 2006 in the name of Suzanne Dagher is hereby claimed under the provisions of 35 USC 119(e). The disclosure of such Provisional Patent Application 60/756,269 is hereby incorporated herein by reference, in its entirety.

GOVERNMENTAL INTERESTS

This invention was made with governmental support under Grant No. 2R44GM0609024-02, awarded by The National Institutes of Health's National Institute of General Medical Sciences. The Government has certain rights in the invention.

FIELD OF THE INVENTION

The present invention relates to fusion constructs comprising multimeric elastin-like peptides (ELPs) having utility, inter alia, in biopharmaceutical applications, and to methods of making and using the same.

DESCRIPTION OF THE RELATED ART

U.S. Pat. No. 6,852,834 issued Feb. 8, 2005 in the name of Ashutosh Chilkoti for "FUSION PEPTIDES ISOLATABLE BY PHASE TRANSITION" and U.S. patent application Ser. No. 11/053,100 filed Feb. 8, 2005 for "FUSION PEPTIDES ISOLATABLE BY PHASE TRANSITION," in the name of Ashutosh Chilkoti (published Nov. 17, 2005 as U.S. Patent Publication No. 2005/0255554) disclose fusion proteins exhibiting a phase transition. Such fusion proteins comprise a biologically active molecule joined to one or more phase transition protein(s), where the one or more phase transition protein(s) comprise polymeric or oligomeric repeats of a polypeptide sequence. The fusion protein may also, optionally, contain a spacer sequence between the biologically active molecule and the one or more phase transition protein(s).

The biologically active molecules in these constructs can be of widely varying types, including, for example, peptides, non-peptide proteins, lipids, oligonucleotides and carbohydrates, or alternatively a ligand-binding protein or an active fragment thereof having binding affinity to a biomolecule selected from the group consisting of small organic or inorganic molecules, proteins, peptides, single-stranded or double-stranded oligonucleotides, polynucleotides, lipids, and carbohydrates.

The phase transition can be mediated by one or more techniques such as changing temperature, changing pH, addition of solutes and/or solvents, side-chain ionization or chemical modification and/or changing pressure.

The one or more one or more protein(s) exhibiting phase transition behavior can include polymeric or oligomeric repeats of the pentapeptide Ile-Pro-Gly-X-Gly or Leu-Pro-Gly-X-Gly, wherein X is any natural or non-natural amino acid residue, and wherein X optionally varies among polymeric or oligomeric repeats.

The technology disclosed by the above-identifed Chilkoti patent and application includes methods of purification of fusion proteins to yield a protein of interest, by forming a polynucleotide comprising a nucleotide sequence encoding a fusion protein exhibiting a phase transition, expressing the fusion protein in culture, and subjecting a fusion protein-containing material from the culture to processing involving centrifugation and inverse transition cycling to recover the protein of interest.

The Chilkoti technology reflects an initial discovery that non-chromatographic, thermally-stimulated phase separation and purification of recombinant proteins can be easily achieved by forming fusion proteins that contain the target recombinant proteins with N- or C-terminal elastin-like polypeptide (ELP) tags.

ELPs are repeating peptide sequences that have been found to exist in the elastin protein. Among these repeating peptide sequences are polytetra-, polypenta-, polyhexa-, polyhepta-, polyocta, and polynonapeptides.

ELPs undergo a reversible inverse temperature transition: they are structurally disordered and highly soluble in water below a transition temperature ($T_t$), but exhibit a sharp (2-3° C. range) disorder-to-order phase transition when the temperature is raised above $T_t$, leading to desolvation and aggregation of the polypeptides. The ELP aggregates, when reaching sufficient size, can be readily removed and isolated from solution by centrifugation. More importantly, such phase transition is reversible, and the isolated ELP aggregates can be completely resolubilized in buffer solution when the temperature is returned below the $T_t$ of the ELPs.

It was a surprising and unexpected discovery that fusion proteins ("FPs") containing target recombinant proteins with N- or C-terminal ELP tags also undergo a thermo-dependent phase transition similar to that of free ELPs.

This discovery has been particularly useful for non-chromatographic, thermally-stimulated separation and purification of recombinant proteins. By fusing a thermally responsive ELP tag to a target protein of interest, environmentally sensitive solubility can be imparted to such target protein. Target proteins are readily expressed as soluble fusion proteins with N- or C-terminal ELP sequences in host organisms such as *E. coli*, wherein the fusion proteins exhibit a soluble-insoluble phase transition when the temperature is raised from below $T_t$ to above $T_t$. This inverse phase transition is exploited for purifying the target proteins from other soluble proteins produced by the organism, by nonchromatographic "inverse transition cycling" (ITC) separation.

The fundamental principle of ITC thus is remarkably simple. It involves forming an ELP fusion protein as described hereinabove, which contains the target protein with a N- or C-terminal ELP tag, rendering the ELP fusion protein insoluble in aqueous solution by triggering its inverse phase transition. This can be accomplished either by increasing the temperature above the $T_t$, or alternatively by depressing the $T_t$ below the solution temperature by the addition of NaCl or other salt or solute, organic or inorganic, to the solution. This results in aggregation of the ELP fusion protein, allowing it to be collected by centrifugation or other weight- and/or size-dependent mass separation techniques, e.g., membrane separation or filtration.

The aggregated ELP fusion protein can then be resolubilized in fresh buffer solution at a temperature below the $T_t$, thereby reversing the inverse phase transition, to yield soluble, functionally active, and purified fusion protein.

Successive purification steps may also be carried out using ITC to achieve a highly pure, e.g., ultrapure, fusion protein product. Furthermore, ITC may also be used to concentrate and exchange buffers if desired as follows: the purified protein is aggregated by triggering the phase transition, and resolubilized in a smaller volume than before inducing the phase transition to concentrate the protein solution, and buffer exchange is achieved by simply resolubilizing the protein in a buffer of different composition than the starting buffer.

Free target protein then can be obtained, for example, by carrying out protease digestion or other scission process at an engineered recognition site located between the target protein and the ELP tag, followed by a final round of ITC to remove the cleaved ELP tag and yield the purified free target protein.

The advantage of the use of inverse phase transition cycling is that purification of the protein of interest is facilitated in a ready and efficient manner. Protein production and purification efficiency are of continuing interest in ongoing efforts to refine and develop this technology, involving the search for new constructs that are well-adapted to the inverse phase transition cycling process, to yield proteins of interest at high yields. The present invention provides such new constructs.

SUMMARY OF THE INVENTION

The present invention is based on the discovery of new protein constructs that are easier to purify, enable production of peptide or protein products in higher amounts and are less susceptible to proteolysis, as compared to the single ELP-based constructs of the prior art. Such constructs are useful in inverse phase transition processes.

Thus in one embodiment, the invention provides a fusion protein exhibiting a phase transition, including at least one target protein or peptide, one or more proteins comprising oligomeric repeats of a polypeptide sequence, wherein the one or more proteins exhibits a phase transition and are joined to the at least one target protein or peptide, at least two residues capable of forming a disulfide bond and optionally a spacer sequence separating any of the phase transition protein(s) from any of the target protein(s) or peptide(s). The invention also provides a polynucleotide encoding such a fusion protein, an expression vector comprising such a polynucleotide and a host cell that expresses the fusion protein.

In another embodiment the invention provides ELP spider complex comprising two or more fusion proteins exhibiting a phase transition, including at least one target protein or peptide, one or more proteins comprising oligomeric repeats of a polypeptide sequence, wherein the one or more proteins exhibits a phase transition and are joined to the at least one target protein or peptide, at least two residues capable of forming a disulfide bond and optionally a spacer sequence separating any of the phase transition protein(s) from any of the target protein(s) or peptide(s), wherein the two or more fusion proteins exhibiting a phase transition are linked by at least one disulfide bond.

In still another embodiment the invention provides methods of providing a purified protein of interest and of enhancing proteolytic resistance of a protein or peptide moiety.

The method of the invention providing a purified protein of interest comprises contacting a fusion protein comprising the protein of interest and an ELP tag, wherein the fusion protein contains at least one cleavage site that is cleavable to yield the protein of interest as a cleavage product with ELP-TEV1 that is effective to cleave the cleavage site, thereby yielding said protein of interest as a cleavage product in a cleavage product mixture comprising said ELP tag, any uncleaved fusion protein and said ELP-tagged cleavage agent; and separating the protein of interest from the cleavage produce mixture by inverse phase transition.

In another aspect the invention provides a method of enhancing proteolytic resistance of a protein or peptide moiety in an ELP-based fusion peptide, comprising provision of the ELP-based fusion peptide in an ELP spider complex.

DETAILED DESCRIPTION OF THE INVENTION, AND PREFERRED EMBODIMENTS THEREOF

Figure 1A:
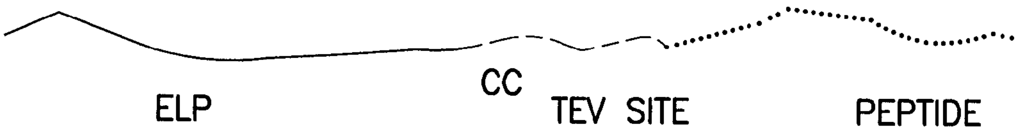
FIG. 1A is a schematic representation of an ELP fusion protein including a -Cys-Cys-moiety after the ELP and before the TEV site and the peptide.

The present invention relates to multimeric elastin-like peptide (ELP) constructs having utility for biopharmaceutical applications, and methods of making and using the same.

The disclosures of the following U.S. patent and U.S. patent application are hereby incorporated herein by reference in their respective entireties: U.S. Pat. No. 6,852,834 issued Feb. 8, 2005 in the name of Ashutosh Chilkoti for "FUSION PEPTIDES ISOLATABLE BY PHASE TRANSITION" and U.S. patent application Ser. No. 11/053,100 filed Feb. 8, 2005 for "FUSION PEPTIDES ISOLATABLE BY PHASE TRANSITION," in the name of Ashutosh Chilkoti (published Nov. 17, 2005 as U.S. Patent Publication No. 2005/0255554).

The present invention represents the discovery that multimeric ELP-peptide or ELP-protein constructs can be formed that in relation to single ELP-based peptide or protein constructs of the prior art: (i) can be more easily purified, (ii) enable production, e.g., in a suitable host such as *E. coli*, of peptide or protein products in higher amounts, reflecting enhanced stability in relation to single ELP-based peptide or protein constructs, and (iii) are less susceptible to proteolysis.

As used herein, the term "spider construct" is used to refer to fusion proteins capable of forming multimeric or multi-legged spider complexes of the present invention. Spider constructs differ from single ELP-based constructs in that they are capable of forming covalent crosslinks in the form of disulfide bonds, linking them to other spider constructs and forming spider complexes. Such disulfide bonds are often formed between cysteine residues of the spider constructs. Cysteine residues present in a construct of the invention may be added to the construct on either side of the ELP or may be found within the ELP itself. Cysteines adjacent to the ELP in the construct may be on either the C-terminal or N-terminal end of the ELP, regardless of whether the ELP is oriented to the amino or carboxyl end of the protein or peptide.

A "spider complex" of the invention contains at least two spider constructs linked by at least one disulfide bond, but is not limited by any maximum number of spider constructs or any maximum number of disulfide bonds.

Therefore in one embodiment the invention provides a fusion protein or spider construct comprising a) at least one target protein or peptide;

b) one or more proteins comprising oligomeric repeats of a polypeptide sequence, such as those hereinafter described, wherein the one or more proteins exhibit a phase transition and are joined to the at least one target protein or peptide of a);

c) at least two residues capable of forming a disulfide bond; and d) optionally, a spacer sequence separating any of the phase transition protein(s) of b) from any of the target protein(s) or peptide(s) of a).

The fusion protein of the invention contains a target protein or peptide. More preferably, the target protein or peptide comprises a polypeptide protein, most preferably a biologically active polypeptide, e.g., a therapeutic peptide, protein or an enzyme useful in industrial biocatalysis. Suitable proteins include those of interest in medicine, agriculture and other scientific and industrial fields, particularly including therapeutic proteins such as erythropoietins, inteferons, insulin, monoclonial antibodies, blood factors, colony stimulating factors, growth hormones, interleukins, growth factors, therapeutic vaccines, calcitonins, tumor necrosis factors (TNF), and enzymes. Specific examples of such therapeutic proteins include, without limitation, enzymes utilized in replacement therapy; hormones for promoting growth in animals, or cell growth in cell culture; and active proteinaceous substances used in various applications, e.g., in biotechnology or in medical diagnostics. Specific examples include, but are not limited to: superoxide dismutase, interferon, asparaginease, glutamase, arginase, arginine deaminase, adenosine deaminase ribonuclease, trypsin, chromotrypsin, papin, insulin, calcitonin, ACTH, glucagon, somatosin, somatropin, somatomedin, parathyroid hormone, erthyropoietin, hypothalamic releasing factors, prolactin, thyroid stimulating hormones, endorphins, enkephalins, and vasopressin.

The target protein or peptide may also comprise a ligand-binding protein or an active fragment thereof, such as an antibody or antibody fragment, which has specific affinity for a protein of interest. Upon binding to the protein of interest, the fusion protein preferably retains some or all of its phase transition character, so that the protein of interest bound to such fusion protein may be isolated by inverse phase transition. In another embodiment the target protein or peptide may be selected from the group consisting of proteins, lipids, carbohydrates, and single- or double-stranded oligonucleotides.

In various embodiments of the invention, the target protein or peptide may be, but is not limited to, IFNa2b, Orexin-B, MMN, NPY, Gh or active fragments thereof.

In addition to the target protein or peptide component, a fusion protein of the invention also includes one or more ELPs exhibiting a phase transition. These ELPs may be of any suitable type.

As used herein, ELPs are repeating peptide sequences that exist in the elastin protein. Among these repeating peptide sequences are polytetra-, polypenta-, polyhexa-, polyhepta-, polyocta, and polynonapeptides.

The ELPs may comprise polymeric or oligomeric repeats of various tetra-, penta-, hexa-, hepta-, octa-, and nonapeptides, including but not limited to VPGG (SEQ ID NO: 1), IPGG (SEQ ID NO: 2), XGVPG (SEQ ID NO: 3), VGVPG (SEQ ID NO: 4), VPAVG (SEQ ID NO: 5), GVGIP (SEQ ID NO: 6), VGLPG (SEQ ID NO: 7), VPGXG (SEQ ID NO: 8), AVGVP (SEQ ID NO: 9), IPGVG (SEQ ID NO: 10), IPGXG (SEQ ID NO: 11), LPGVG (SEQ ID NO: 12), LPGXG (SEQ ID NO: 13), VAPGVG (SEQ ID NO: 14), GVGVPGVG (SEQ ID NO: 15), VPGFGVGAG (SEQ ID NO: 16), and VPGVGVPGG (SEQ ID NO: 17). It will be appreciated by those of skill in the art that the ELPs need not consist of only polymeric or oligomeric sequences as listed hereinabove, in order to exhibit the desired phase transition, and that other polymeric or oligomeric sequences of varying size and constitution that exhibit phase transition behavior are also usefully employed in the broad practice of the present invention.

In one embodiment, the ELPs are polymeric or oligomeric repeats selected from one of the above listed polypentapeptides. Where the above polypentapeptides contain a guest residue X, X may be any amino acid that does not eliminate the phase transition characteristics of the ELP. X may be a naturally occurring or non-naturally occurring amino acid. For example, X may be selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In one aspect of the invention, where the ELP is VPGXG (SEQ ID NO: 8), X is not proline.

X may be a non-classical amino acid. Examples of non-classical amino acids include: D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general.

In one embodiment, the ELP is a "Series I" pentapeptide of repeating oligomer XGVPG (SEQ ID NO: 3) where X is independently selected from Val, Gly and Ala, in a ratio of 5V:3G:2A, selected from ELP1-90 and ELP1-180.

In another embodiment, the ELP is a "Series II" pentapeptide of repeating oligomer XGVPG (SEQ ID NO: 3) where X is independently selected from Lys, Val and Phe, in a ratio of 1K:2V:1F, selected from ELP2-64 and ELP2-128.

In still another embodiment of the invention, the ELP is a "Series III" pentapeptide of repeating oligomer XGVPG (SEQ ID NO: 3) where X is independently selected from Lys, Val and Phe, in a ratio of 1K:7V:1F, selected from ELP3-72 and ELP3-144.

In a further embodiment, the ELP is a "Series IV" pentapeptide of repeating oligomer VGVPG (SEQ ID NO: 4), selected from ELP4-60 and ELP4-120.

In a further embodiment, the ELP is a "Series V" pentapeptide of repeating oligomer VPAVG (SEQ ID NO: 5), selected from ELP5-15, ELP5-30 and ELP5-60.

In a further embodiment, the ELP is a "Series VI" pentapeptide of repeating oligomer GVGIP (SEQ ID NO: 6), selected from ELP6-15, ELP6-30 and ELP6-60.

In a further embodiment, the ELP is a "Series VII" pentapeptide of repeating oligomer VGLPG (SEQ ID NO: 7), selected from ELP7-15, ELP7-30 and ELP7-60.

Alternatively, such ELPs can be polymeric or oligomeric repeats of the pentapeptide IPGXG (SEQ ID NO: 11) or LPGXG (SEQ ID NO: 13), where X is as defined hereinabove.

Therefore in one embodiment of the invention, the fusion protein contains a phase transition protein selected from the group consisting of: SEQ ID NO: 1-17.

In another embodiment of the invention, the fusion protein contains a phase transition protein selected from the group consisting of: SEQ ID NOs: 1, 2, 8, 9, 10, 11, 12, 13, 14, 15, 16, and 17.

In still another embodiment, the fusion protein contains a phase transition protein selected from the group consisting of: SEQ ID NOs: 1, 2, 9, 10, 11, 12, 13, 14, 15, 16, and 17.

A further embodiment of the invention relates to a fusion protein containing a phase transition protein, wherein the phase transition protein is selected from the group consisting of: ELP1-90, ELP1-180, ELP2-64, ELP2-128, ELP3-72, ELP3-144, ELP4-60, ELP4-120, ELP5-15, ELP5-30, ELP5-60, ELP6-15, ELP6-30, ELP6-60, ELP7-15, ELP7-30 and ELP7-60.

In the fusion protein the phase transition protein is joined to the at least one target protein or peptide. Such joining may be on either end of the target protein or peptide, forming either an N- or C-terminal ELP tag.

The fusion protein of the invention contains at least two residues capable of forming a disulfide bond. In one aspect this comprises the presence of two cysteine residues within the ELP monomer sequence. In another aspect the cysteines are located elsewhere in the fusion protein, either adjacent to the ELP, or separated from the ELP. The cysteines may be located on either side of the ELP within the fusion protein.

An example of an ELP containing two cysteines within the monomer sequence is set forth below. In the example, the ELP is of a general form "ELPx-y", where x is an indicator of the ELP series and y is the number of oligomeric repeats. In the following exemplified sequence, the ratio of G:V:C:A is 2:5:2:2.

```
 G  V  G  V  P  G  V  G  V  P  G   (SEQ ID NO: 18)
GGCGTGGGTGTTCCGGGCGTGGGTGTTCCGGGTT (SEQ ID NO: 19)

C  C  V  P  G  A  G  V  P  G  V  G
GCTGCGTGCCGGGCGCAGGTGTTCCTGGTGTAGG

 V  P  G  V  G  V  P  G  V  G  V
TGTGCCGGGTGTTGGTGTGCCGGGTGTTGGTGTA
```

-continued

```
P  G  G  G  V  P  G  A  G  V  P
CCAGGTGGCGGTGTTCCGGGTGCAGGCGTTCCGG

G  G  G  V  P  G
GTGGCGGTGTGCCGGGC . . .
```

Another example of an ELP containing two cysteines within the monomer sequence is set forth below, where the ratio of G:V:C:A is 1:5:2:2.

```
 G  V  G  V  P  G  V  G  V  P  G   (SEQ ID NO: 20)
GGCGTGGGTGTTCCGGGCGTGGGTGTTCCGGGTT (SEQ ID NO: 21)

C  G  V  P  G  A  G  V  P  G  V  G
GCGGGGTGCCGGGCGCAGGTGTTCCTGGTGTAGG

 V  P  G  V  G  V  P  G  V  G  V
TGTGCCGGGTGTTGGTGTGCCGGGTGTTGGTGTA

P  G  C  G  V  P  G  A  G  V  P
CCAGGTTGCGGTGTTCCGGGTGCAGGCGTTCCGG

G  G  G  V  P  G
GTGGCGGTGTGCCGGGC . . .
```

The phase transition of the fusion protein is preferably mediated by one or more mechanisms selected from, but not limited to, changing temperature, changing pH, addition of (organic or inorganic) solutes and/or solvents, side-chain ionization or chemical modification, irradiation with electromagnetic waves (rf, ultrasound, and light) and changing pressure. The preferred mechanisms for mediating the phase transition are raising temperature and adding solutes and/or solvents.

Optionally, the fusion protein may contain a spacer sequence separating the phase transition protein from the target protein or peptide. The spacer sequence, when present, preferably comprises a cleavage site, e.g., a proteolytic cleavage site, a chemical cleavage site, a photolytic cleavage site, a thermolytic cleavage site, or a cleavage site susceptible to cleavage in the presence of a shear force, pH change, enzymatic agent, ultrasonic or other predetermined frequency field providing energy effective for cleavage. The cleavage modality may be of any of widely varying types, it being necessary only that the cleaving step yield at least one biological molecule (as a cleavage product) that retains functional utility for its intended purpose.

The fusion peptides of the present invention may also optionally comprise signal peptides for directing secretion of the fusion peptides from the cell, so that the fusion peptides may readily be isolated from the medium of an active culture of recombinant cells genetically modified to produce the fusion peptides. Such signal peptides are preferably cleavable from the fusion protein by enzymatic cleavage.

Therefore in one embodiment the invention provides a fusion protein comprising a spacer sequence. In another embodiment the invention provides a fusion protein with a spacer sequence that is a proteolytic cleavage site.

In one embodiment, the invention provides a fusion protein selected from pET17b-SD33-ELP1-90-IFNA2bSD (SEQ ID NO: 22), pET17b-SD33-ELP4-60-IFNA2bSD (SEQ ID NO: 23), pET17b-SD34-ELP1-90-IFNA2bSD (SEQ ID NO: 24), pET17b-SD34-ELP4-60-IFNA2bSD (SEQ ID NO: 25), pET17b-SD22-ELP1-90-IFNA2bSD (SEQ ID NO: 26), pET17b-SD22-ELP4-60-IFNA2bSD (SEQ ID NO: 27), pET17b-SD35-IFNA2bSD-ELP1-90 (SEQ ID NO: 28), pET17b-SD35-IFNA2bSD-ELP4-60 (SEQ ID NO: 29), pET17b-SD37-IFNA2bSD-ELP1-90 (SEQ ID NO: 30), pET17b-SD37-IFNA2bSD-ELP4-60 (SEQ ID NO: 31), pET17b-SD31-IFNA2bSD-ELP1-90 (SEQ ID NO: 32) and pET17b-SD31-IFNA2bSD-ELP4-60 (SEQ ID NO: 33).

In another embodiment the invention provides a fusion protein selected from ELP4-60-S—S-Orexin B, ELP4-60-S—S-MMN, ELP4-60-S—S-NPY and ELP4-60-S—S-Gh.

Yet another embodiment of the invention relates to a polynucleotide comprising a nucleotide sequence encoding a fusion protein exhibiting a phase transition, comprising:

a) at least one target protein or peptide;

b) one or more proteins comprising oligomeric repeats of a polypeptide sequence selected from SEQ ID NOs: 1-17, wherein the one or more proteins exhibits a phase transition and are joined to the at least one target protein or peptide of a);

c) at least two residues capable of forming a disulfide bond; and d) optionally, a spacer sequence separating any of the phase transition protein(s) of b) from any of the target protein(s) or peptide(s) of a).

The invention in a further aspect relates to a polynucleotide selected from pET17b-SD33-ELP1-90-IFNA2bSD (SEQ ID NO: 34), pET17b-SD33-ELP4-60-IFNA2bSD (SEQ ID NO: 35), pET17b-SD34-ELP1-90-IFNA2bSD (SEQ ID NO: 36), pET17b-SD34-ELP4-60-IFNA2bSD (SEQ ID NO: 37), pET17b-SD22-ELP1-90-IFNA2bSD (SEQ ID NO: 38), pET17b-SD22-ELP4-60-IFNA2bSD (SEQ ID NO: 39), pET17b-SD35-IFNA2bSD-ELP1-90 (SEQ ID NO: 40), pET17b-SD35-IFNA2bSD-ELP4-60 (SEQ ID NO: 41), pET17b-SD37-IFNA2bSD-ELP1-90 (SEQ ID NO: 42), pET17b-SD37-IFNA2bSD-ELP4-60 (SEQ ID NO: 43), pET17b-SD31-IFNA2bSD-ELP1-90 (SEQ ID NO: 44) and pET17b-SD31-IFNA2bSD-ELP4-60 (SEQ ID NO: 45).

In still another embodiment the invention provides an expression vector comprising a polynucleotide encoding a fusion protein of the invention. In yet another embodiment the invention provides a host cell transformed by such an expression vector, where the host cell expresses the fusion protein.

In a still further embodiment, the invention provides an ELP spider complex comprising two or more fusion proteins of the invention, covalently linked by at least one disulfide bond.

The invention also provides a spider complex which includes two or more fusion proteins exhibiting a phase transition comprising:

a) at least one target protein or peptide;

b) one or more proteins comprising oligomeric repeats of a polypeptide sequence selected from SEQ ID NOs: 1-17, wherein the one or more proteins exhibits a phase transition and are joined to the at least one target protein or peptide of a);

c) at least two residues capable of forming a disulfide bond; and d) optionally, a spacer sequence separating any of the phase transition protein(s) of b) from any of the target protein(s) or peptide(s) of a).

wherein the two or more fusion proteins exhibiting a phase transition are covalently linked by at least one disulfide bond.

The invention also provides methods of utilizing the fusion proteins and spider complexes as discussed herein.

In one aspect the invention relates to a method of providing a purified protein of interest, comprising contacting a fusion protein comprising the protein of interest and an ELP tag, wherein the fusion protein contains at least one cleavage site that is cleavable to yield the protein of interest as a cleavage product with ELP-TEV1 that is effective to cleave said cleavage site, thereby yielding said protein of interest as a cleavage product in a cleavage product mixture comprising said ELP tag, any uncleaved fusion protein and said ELP-tagged cleavage agent and separating the protein of interest from the cleavage produce mixture by inverse phase transition.

In another aspect the invention provides a method of enhancing proteolytic resistance of a protein or peptide moiety in an ELP-based fusion peptide, comprising provision of the ELP-based fusion peptide in an ELP spider complex form.

Examples of spider complexes discussed herein include Orexin B/ELP and IFNa2bSD/ELP spider constructs, but are broadly applicable to a wide spectrum of other proteins and peptides, and have particular utility for proteins or peptides that are susceptible to proteolytic degradation.

Methods of protection of target proteins or peptides by the spider construct may involve, but are not limited to: (i) slowing or stopping degradative action of proteases, (ii) decreasing or eliminating non-specific associated proteins that may make the target protein or peptide insoluble or prevent the target protein or peptide from properly folding, (iii) increasing the amount of total spider construct concentration in the cell, and/or (iv) exposure of a region of the target protein or peptide subject to proteolysis by the ELP fused to TEV protease when produced in the absence of disulfide bonds. Disulfides formed between ELP and TEV site have been tested. Spacing may be desirably adjusted for such bonding, e.g., with intra-disulfide bonds being separated by at least 2 amino acid residues, such as for example by a -Cys-Cys-moiety. Other techniques for increasing inter- and decreasing intra-disulfide bond formation can be employed.

Figure 1B:
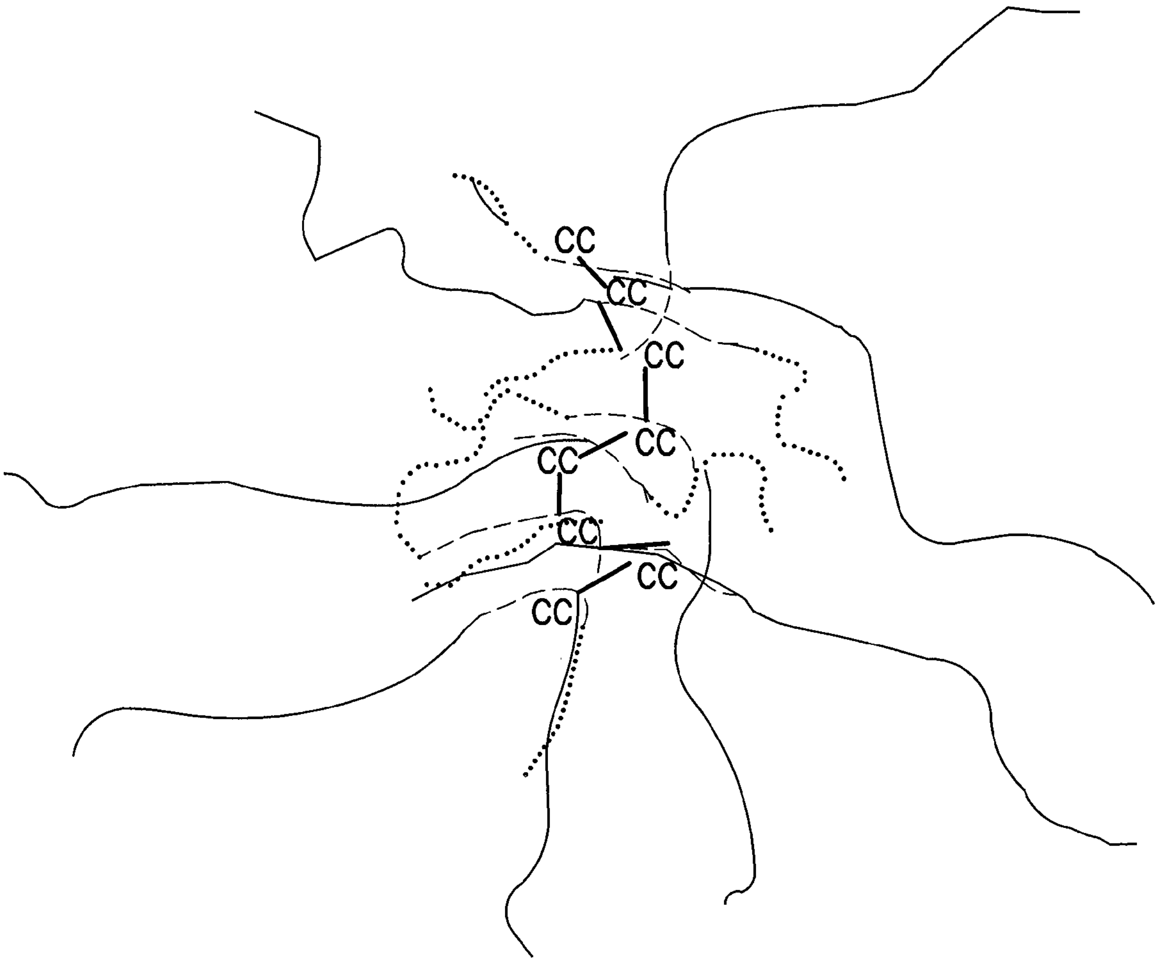
FIG. 1B is a schematic representation of a corresponding spider construct, for pET17b-SD34-ELP4-60-Orexin B (as set forth below in Example 1), and transformation into a BL21 trxB-strain, allowing disulfide bond formation between the fusion proteins to take place in the cytoplasm.

FIG. 1A is a schematic representation of an ELP fusion protein including a -Cys-Cys-moiety after the ELP and before the TEV site and the peptide. FIG. 1B is a schematic representation of a corresponding spider construct, for pET17b-SD34-ELP4-60-Orexin B (as set forth below in Example 1), and transformation into a BL21 trxB-strain, allowing disulfide bond formation between the fusion proteins to take place in the cytoplasm.

The following examples are intended to illustrate, but not limit the invention.

EXAMPLE 1

Comparison of ELP-Orexin B Normal Fusion Protein and ELP-Orexin B Spider Construct Fusion protein constructs of ELP4-60-Orexin B (Normal) and ELP4-60-S—S-Orexin B (Spider) were generated.

Figure 2:
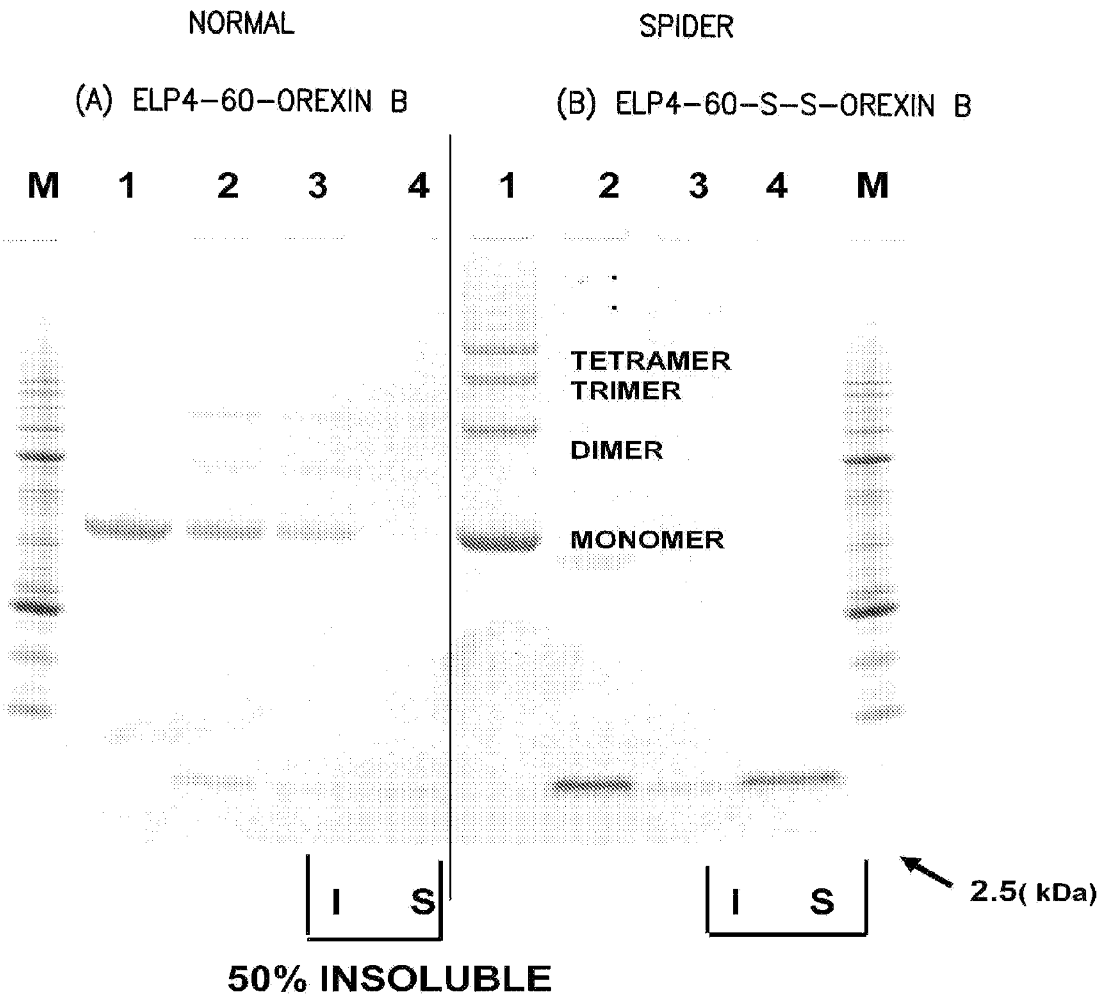
FIG. 2 is an SDS-PAGE gel comparison for ELP4-60-Orexin B (Normal) and ELP4-60-S—S-Orexin B (Spider) (Lane 1: ELP4-60-Orexin B or ELP4-60-S—S-Orexin B; Lane 2: +ELP1-90-TEV; Lane 3: insolubles following $T_t$ (I); and Lane 4: solubles following $T_t$ (S)).

FIG. 2 is an SDS-PAGE gel comparison of the two fusion protein constructs. (Lane 1: ELP4-60-Orexin B or ELP4-60-S—S-Orexin B; Lane 2: +ELP1-90-TEV; Lane 3: insolubles following $T_t$ (I); and Lane 4: solubles following $T_t$ (S)).

Figure 3A:
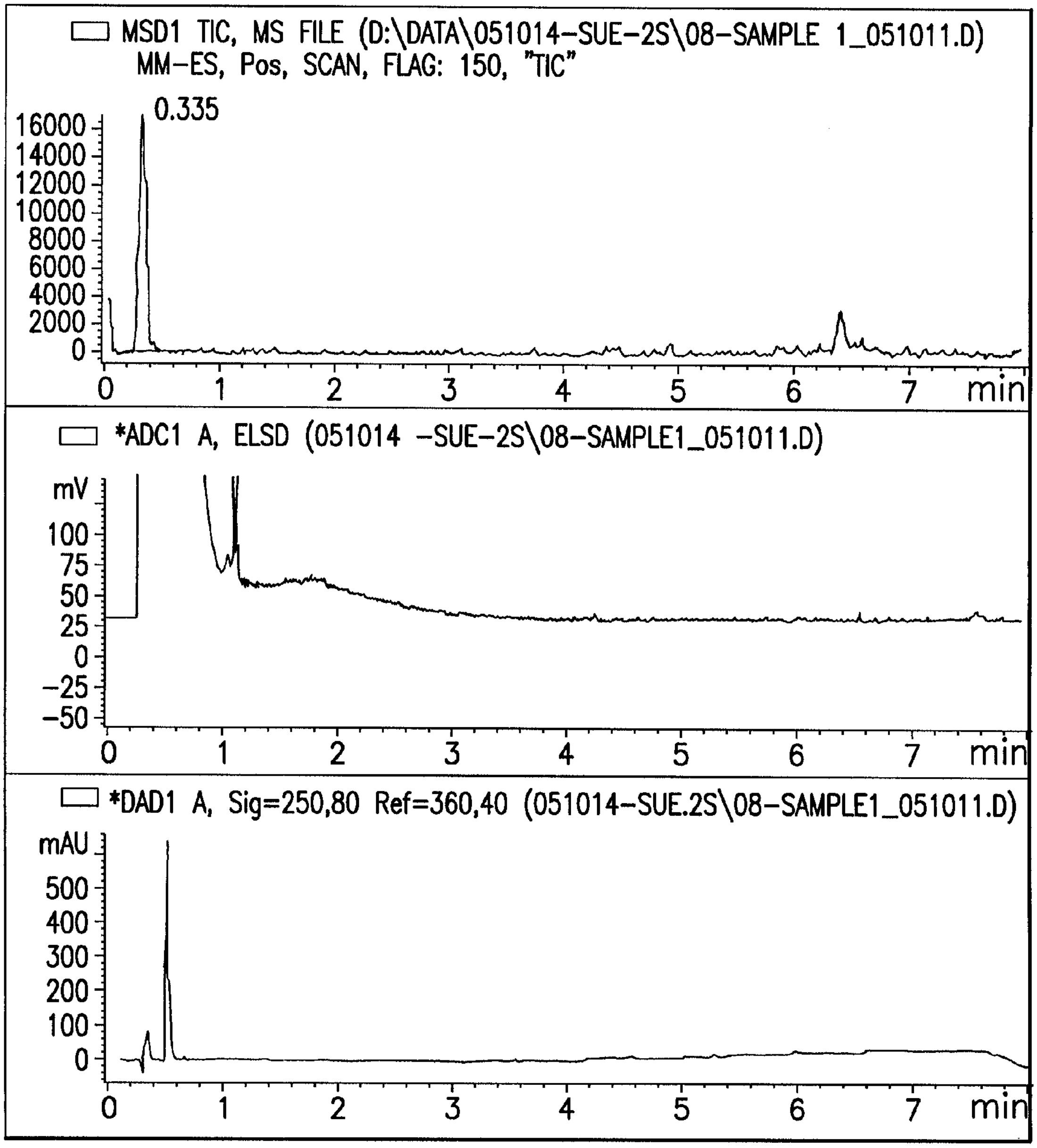
FIG. 3 shows an LC-MS analysis of Orexin B derived from ELP4-60-Orexin B (FIG. 3A), in which the level of Orexin B was too low to detect by LC-MS, so that the theoretical location was estimated by location of Orexin B in (B) and ELP4-60-S—S-Orexin B (FIG. 3B), 85% pure, in which the major peak contains the correct molecular weight of Orexin B and the minor peak is a proteolytic fragment of Orexin B.
Figure 3B:
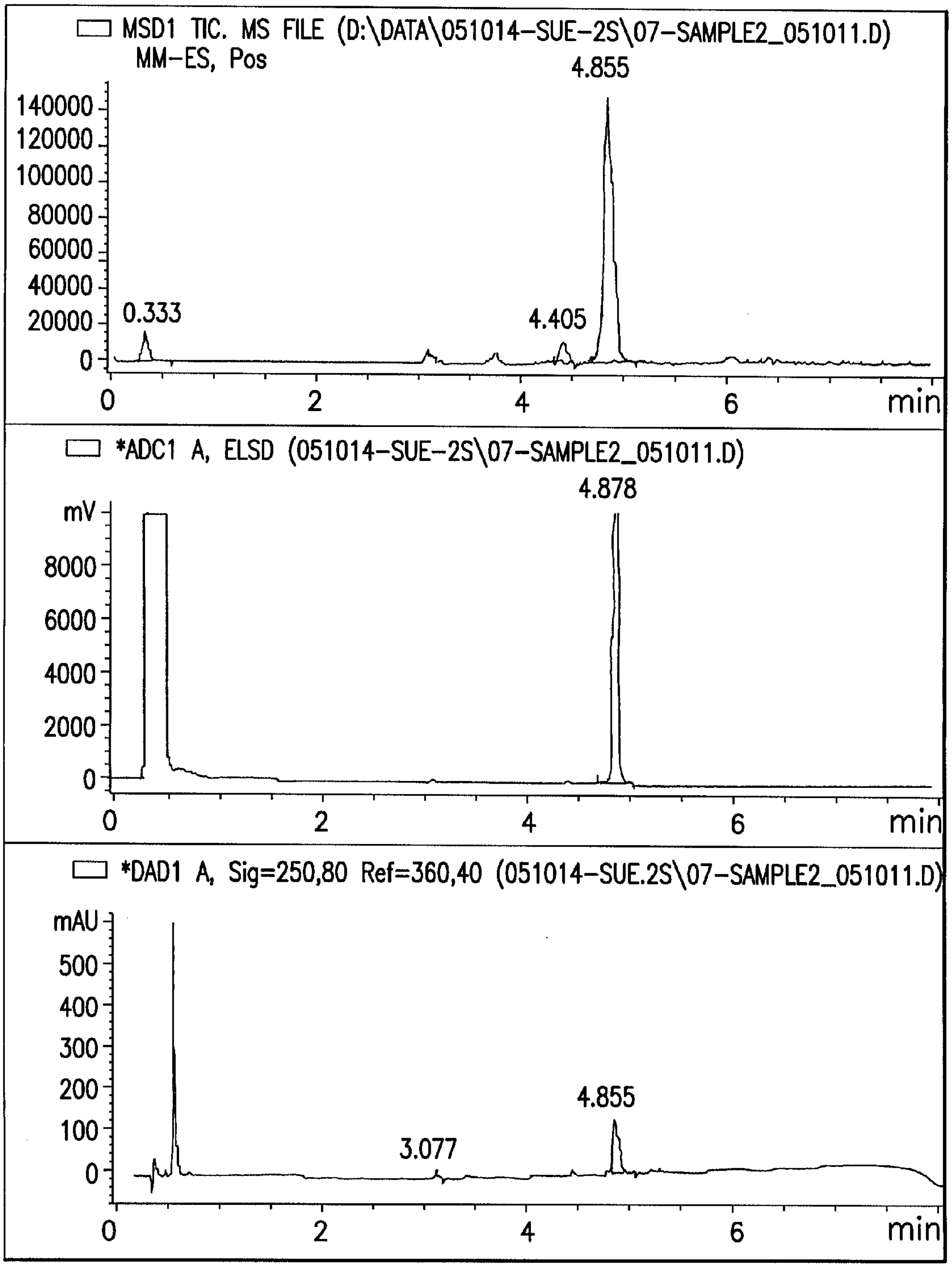

FIG. 3 shows an LC-MS analysis of Orexin B derived from ELP4-60-Orexin B (FIG. 3A), in which the level of Orexin B was too low to detect by LC-MS, so that the theoretical location was estimated by location of Orexin B in (B) and ELP4-60-S—S-Orexin B (FIG. 3B), 85% pure, in which the major peak contains the correct molecular weight of Orexin B and the minor peak is a proteolytic fragment of Orexin B.

The original ELP4-60-Orexin B appeared to purify well, however a substantial amount was difficult to resuspend and purify away from insoluble contaminates. Only a portion of Orexin B was cleaved following 18 hr digestion with ELP1-90-TEV. Once cleaved 50% was insoluble following final transition to eliminate uncleaved ELP4-60-Orexin B, ELP1-90-TEV and ELP4-60. The level of Orexin B was too low to analyze by LC-MS. Loading the gel with 10× more cleaved ELP4-60-Orexin B indicated proteolysis had occurred prior to or during cleavage.

ELP4-60-S—S-Orexin B was much easier to purify away from contaminates. Complete cleavage occurred following 18 hr digestion with ELP1-90-TEV. A minor amount of Orexin B remained insoluble following the final transition to eliminate uncleaved ELP4-60-Orexin B, ELP1-90-TEV, and ELP4-60. LC-MS analysis indicated the largest peak contained the correct molecular weight Orexin B peptide and was 85% of total peaks. The minor peak was a proteolyic fragment of Orexin B.

Figure 4:
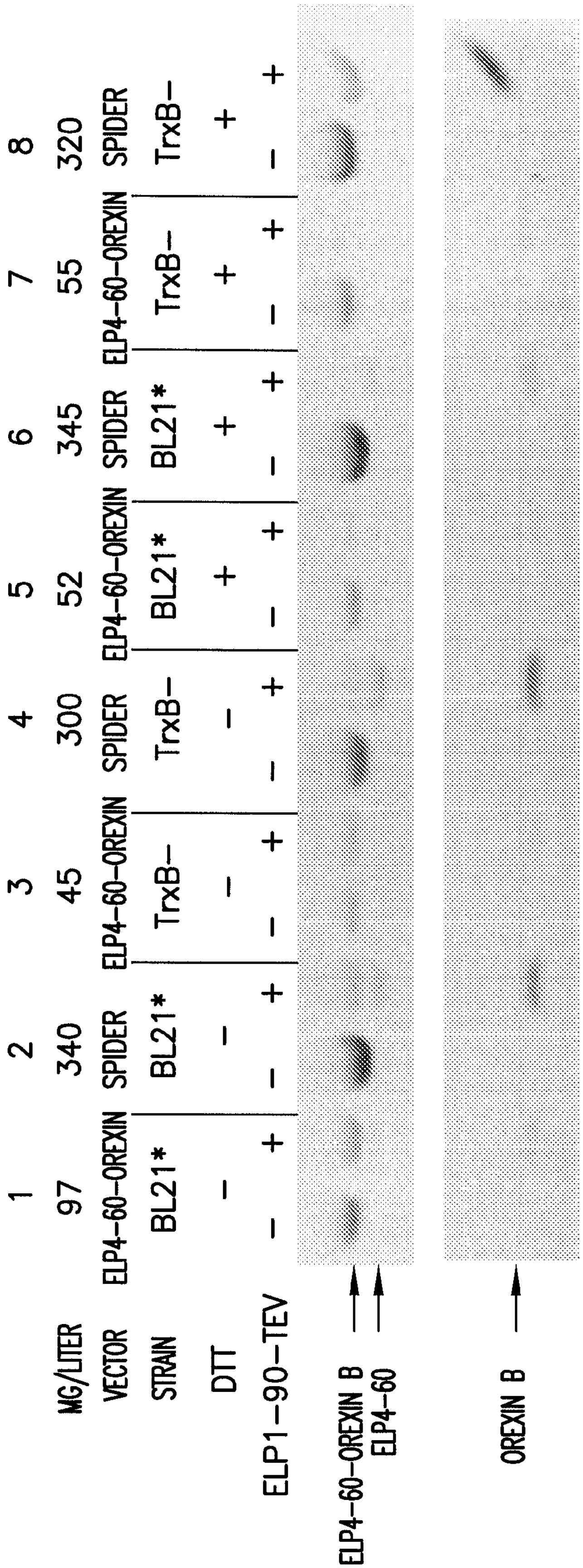
FIG. 4 is a SDS-PAGE gel analysis, showing that the spider influences the amount of purification, the cleavage with ELP4-60-TEV and proteolysis, with all samples being reduced with DTT prior to loading on the SDS-gel.

The fusion protein constructs of ELP4-60-Orexin B (Normal) and ELP4-60-S—S-Orexin B (Spider) were expressed in *E. coli* strains BL21 and trxB. The results are summarized in FIG. 4. FIG. 4 is an SDS-PAGE gel analysis, showing that use of a spider construct influences the amount of purification, the cleavage with ELP4-60-TEV and proteolysis. All samples in the comparison were reduced with DTT prior to loading on the SDS-gel.

It can be seen in FIG. 4 that in both BL21 and trxB, more spider constructs (lanes 2, 4, 6, 8) were produced than normal constructs (lanes 1, 3, 5, 7). Disulfide bond formation within the cytoplasm did not influence the amount of spider construct made. The addition of DTT during purification (lanes 6, 8) did not influence the amount of spider construct purified in the absence of DTT (lanes 2,4). Cleavage with ELP1-90-TEV was not complete when spider constructs were produced in BL21* and purified in the absence of DTT (lane 2). Spider constructs were degraded when produced in BL21* and exposed to DTT during purification (lane 6). The presence of disulfide bonds during expression produced more cleaved Orexin B (lanes 4,8).

EXAMPLE 2

Spider Constructs of Additional Peptides

Figure 5:
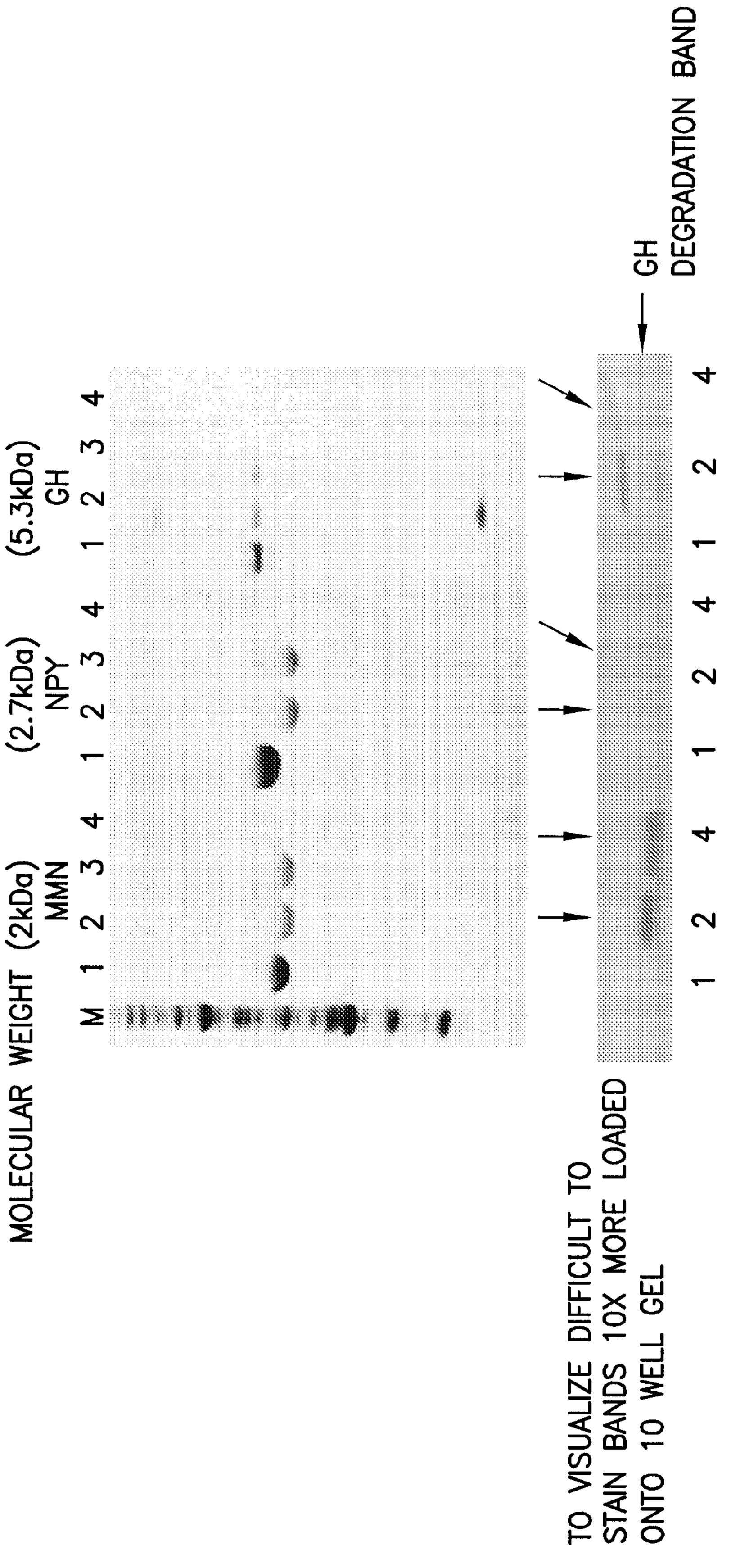
FIG. 5 is an SDS-PAGE gel analysis of ELP-spider constructs of three additional peptides (Lane 1: ELP4-60-S—S-peptide (reduced with DTT); Lane 2: +ELP1-90-TEV; Lane 3: insolubles following $T_t$ (I); and Lane 4: solubles following $T_t$ (S)).

FIG. 5 is an SDS-PAGE gel analysis of ELP-spider constructs of three peptides: MMN, NPY and Gh. For each peptide, the lanes are as follows: Lane 1: ELP4-60-S—S-peptide (reduced with DTT); Lane 2: +ELP1-90-TEV; Lane 3: insolubles following $T_t$ (I); and Lane 4: solubles following $T_t$ (S)).

Comparison of spider constructs and normal constructs were as follows:

MMN peptide: ELP4-60-MMN (58 mg/liter) was not difficult to purify and resulted in 6 mg/liter MMN. ELP4-60-S—S-MMN (180 mg/liter) was not difficult to purify and resulted in 13 mg/liter MMN. It can be seen that use of spider constructs increased the amount of MMN purified.

NPY peptide: ELP4-60-NPY (62 mg/liter) was not difficult to purify and resulted in 7 mg/liter NPY. ELP4-60-S—S-NPY (222 mg/liter) was not difficult to purify and resulted in 20 mg/liter NPY. It can be seen that use of spider constructs increased the amount of NPY purified, it being noted that NPY does not stain well.

Gh peptide: ELP4-60-GH was difficult to purify and resulted in 0 mg/liter Gh. ELP4-60-S—S-GH was not as difficult to purify and resulted in approx 2 mg/liter Gh. A spider construct only partially eliminated Gh degradation. The amount of non-degraded Gh was too low for LC-MS determination. These factors were exacerbated by ELP4-60-Gh transitioning at room temperature (RT):

a. ELP4-60-GH had to be diluted 10 fold compared to MMN and NPY to prevent transitioning at RT during cleavage with ELP 1-90-TEV.

b. The 10-fold dilution made the final concentration of GH too low for LC-MS analysis.

c. Incomplete cleavage with ELP1-90-TEV may be due to a fraction of ELP4-60-GH that continued to transition at RT even after a 10 fold dilution.

d. The low transition temperature of ELP4-60-GH may also be due to contaminants that could not be eliminated through 3 temperature transitions.

It can be seen that use of spider constructs increased the amount of Gh purified.

With all three peptides (MMN, NPY and Gh), use of spider constructs may also act to buffer the possible toxic effect of the peptide and allow more ELP-peptide to be produced per cell, in addition to decreasing proteolysis.

Figure 6A:
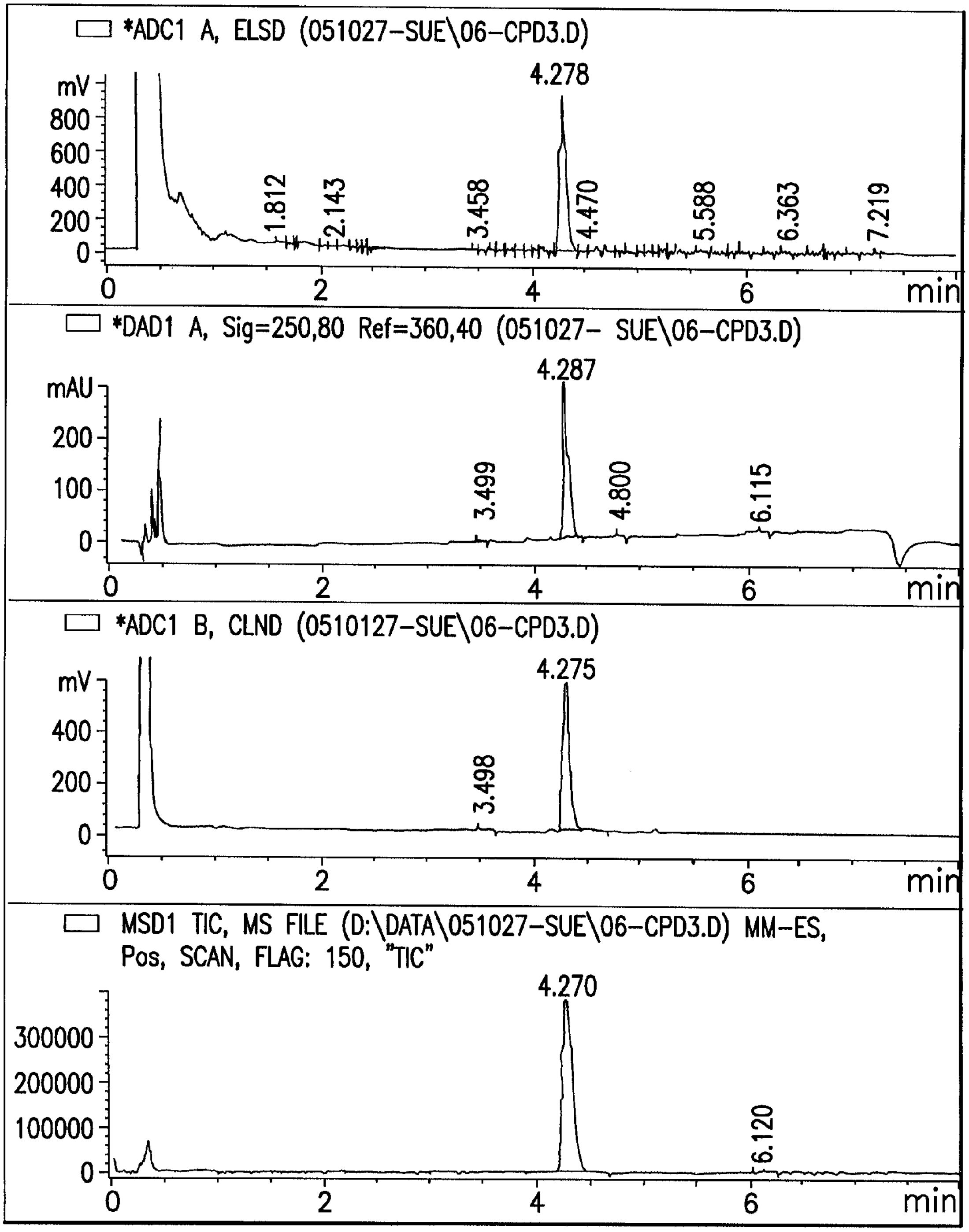
FIG. 6 shows LC-MS analysis for non-spider peptides, MMN from ELP4-60-S—S-MMN: 99.3% pure 13 mg/L (FIG. 6A) and NPY from ELP4-60-S—S-NPY: 98.1% pure 20 mg/L (FIG. 6B).
Figure 6B:
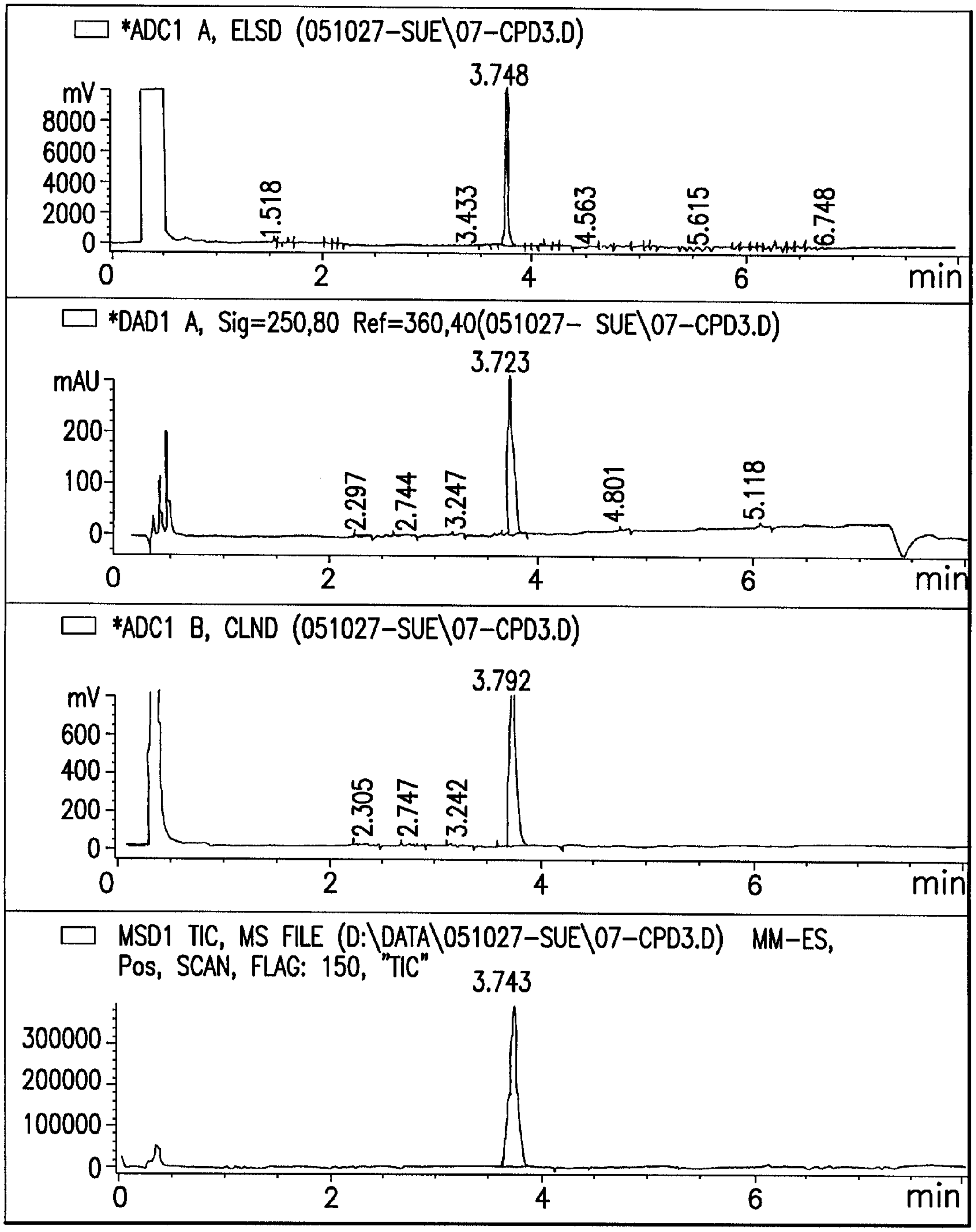

FIG. 6 shows LC-MS analysis for non-spider peptides, MMN from ELP4-60-S—S-MMN: 99.3% pure 13 mg/L (FIG. 6A) and NPY from ELP4-60-S—S-NPY: 98.1% pure 20 mg/L (FIG. 6B).

Figure 7A:
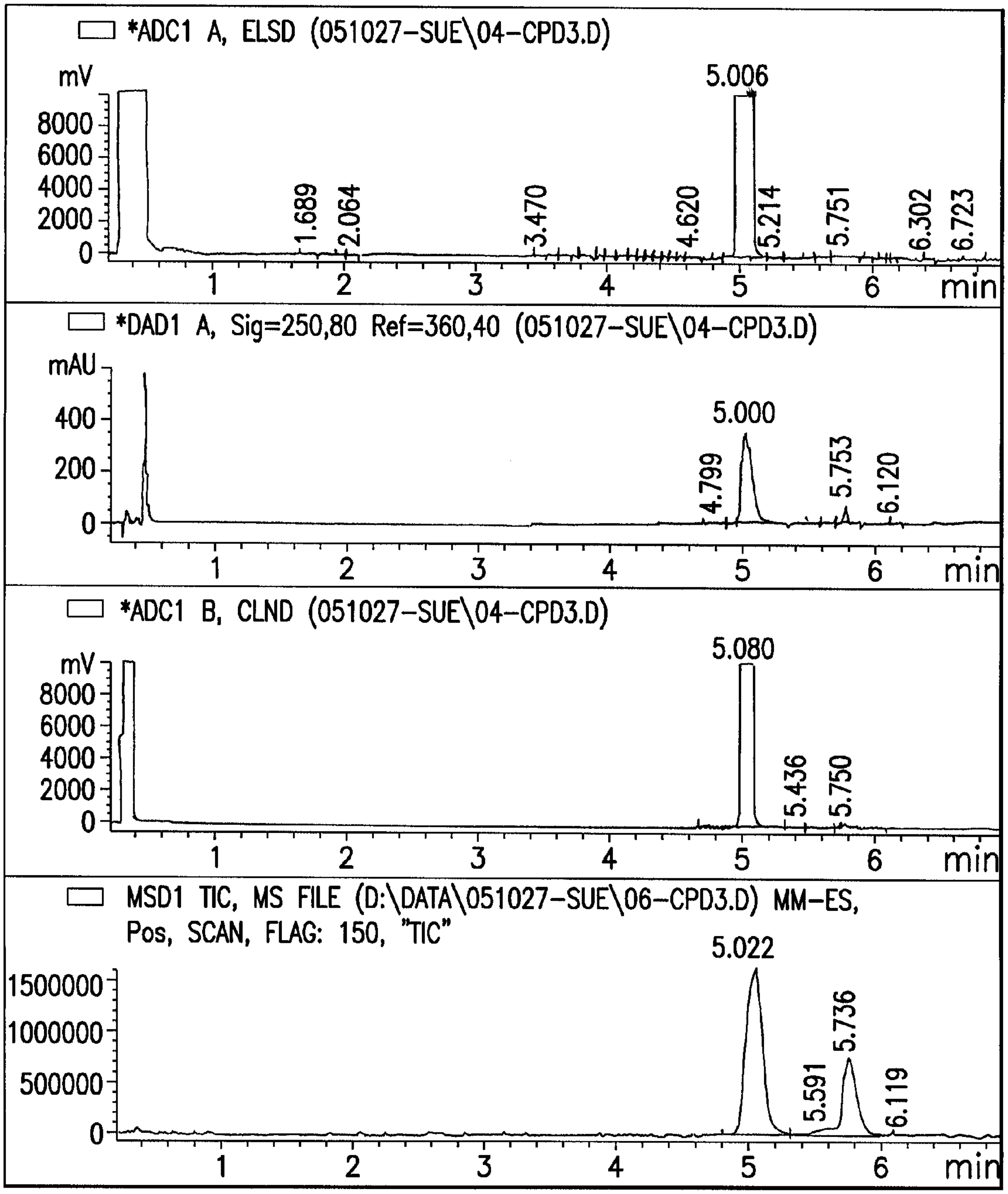
FIG. 7 shows LC-MS analysis for pro-CT from ELP1-90-pro-CT: 98.0% pure (FIG. 7A) and Leptin from ELP1-90-Leptin: 85% pure (FIG. 7B).
Figure 7B:
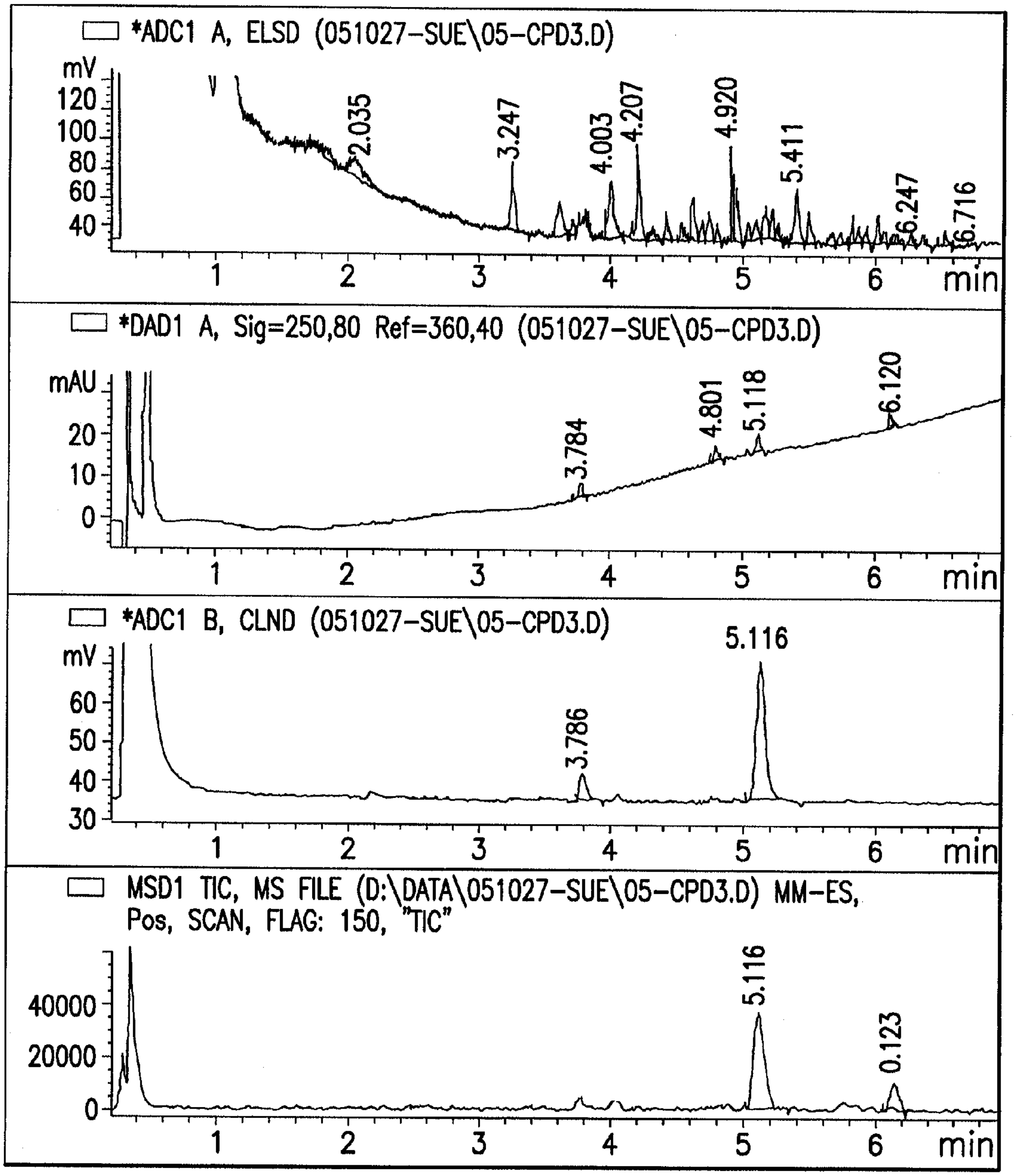

FIG. 7 shows LC-MS analysis for pro-CT from ELP1-90-pro-CT: 98.0% pure (FIG. 7A) and Leptin from ELP1-90-Leptin: 85% pure (FIG. 7B).

EXAMPLE 3

Construction of pET17B-SD35-ELP

SD 35 forward and reverse oligos were annealed, forming 5' XhoI and 3' StyI overhangs:

```
SD35 forward oligo:
                                        (SEQ ID NO: 46)
TCGAGAACCTGTATTTCCAGGGCGGGTGCTGCGGC

SD35 reverse oligo:
                                        (SEQ ID NO: 47)
CTTGGCCGCAGCAGCCGCCCTGGAAATACAGGTTC
```

Annealed oligos:

```
 L  E  N  L  Y  F  Q  G  G  C  C  G  Q  G   (SEQ ID NO: 48)
cTCGAGAACCTGTATTTCCAGGGCGGGTGCTGCGGCcaagg

gagctCTTGGACATAAAGGTCCCGCCCACGACGCCGGTTCc   (SEQ ID NO: 49)
XhoI                                 StyI
```

The annealed SD35 oligos were ligated into pUC19-SD31-ELP, digested with XhoI and Sty1 and 5' dephosphorylated with CIP to create pUC19-SD35-ELP. The pUC19-SD35-ELP XbaI-EcoRI fragment containing SD35-ELP was subcloned into pET17b, digested with XbaI and EcoRI and 5' dephosphorylated with CIP.

In this spider construct, the Cys-Cys is placed following the TEV cleavage site at the amino terminus of the ELP to create a protein/peptide-ELP orientation.

Individual spider constructs pET17b-SD35-ELP1-90 (SEQ ID NO: 50) and pET17b-SD35-ELP4-60 (SEQ ID NO: 51) were created.

EXAMPLE 4

Construction of pEt17b-SD37-ELP

SD37 forward and reverse oligos were annealed, forming BglI and NheI overhangs:

```
                                       (SEQ ID NO: 52)
SD37 forward oligo:    TGGCCTTGCTGCTGATAAG

                                       (SEQ ID NO: 53)
SD37 reverse oligo:    CTAGCTTATCAGCAGCAAGGCCAGCC
```

Annealed oligos:

```
 P   G  W  P  C  C  *  *  A  S    (SEQ ID NO: 54)
gccgggcTGGCCTTGCTGCTGATAAGctagc

cggcCCGACCGGAACGACGACTATTCGATCg   (SEQ ID NO: 55)
BglI                       NheI
```

The annealed SD37 oligos were ligated into pET17b-SD31-ELP, digested with BglI and NheI and 5' dephosphorylated with CIP to create pET17b-SD37-ELP.

In this spider construct, the Cys-Cys is placed at the carboxyl terminus of the ELP to create a protein/peptide-ELP orientation.

Individual spider constructs pET17b-SD37-ELP1-90 (SEQ ID NO: 56) and pET17b-SD37-ELP4-60 (SEQ ID NO: 57) were created.

EXAMPLE 5

Construction of pEt17b-SD33-ELP

SD33 forward and reverse oligos were annealed to form XbaI and NcoI overhangs: SD33 forward oligo:

```
SD33 forward oligo:
                                       (SEQ ID NO: 58)
CTAGAAATAATTTTGTTTAACTTTAAGAAGGAGATATACCATGTGCTGCC

C

SD33 reverse oligo:
                                       (SEQ ID NO: 59)
CATGGGGCAGCACATGGTATATCTCCTTCTTAAAGTTAAACAAAATTATT

T
```

Annealed oligos:

```
                                                 M  C  C   P M G  (SEQ ID NO: 60)
tCTAGAAATAATTTTGTTTAACTTTAAGAAGGAGATATACCATGTGCTGCCCcatgg

agatcTTTATTAAAACAAATTGAAATTCTTCCTCTATATGGTACACGACGGGGTACc  (SEQ ID NO: 61)
XbaI                                                NcoI
```

The annealed SD33 oligos were ligated into pET17b-SD22-ELP digested with XbaI and NcoI and 5' dephosphorylated with CIP to create pET17b-SD33-ELP.

In this spider construct, the Cys-Cys is placed at the amino terminus of the ELP to create an ELP-protein/peptide orientation.

Individual spider constructs pET17b-SD33-ELP1-90 (SEQ ID NO: 62) and pET17b-SD33-ELP4-60 (SEQ ID NO: 63) were created.

EXAMPLE 6

Construction of pEt17b-SD34-ELP

SD34 forward and reverse oligos were annealed to form BglI and EcoRV overhangs:

```
                                          (SEQ ID NO: 64)
SD34 forward oligo:    TGGCCGTGCTGCAGCAGCGGTGAT

                                          (SEQ ID NO: 65)
SD34 reverse oligo:    ATCACCGCTGCTGCAGCACGGCCAGCC
```

Annealed oligos:

```
 P  G  W  P  C  C  S  S  G  D  I  (SEQ ID NO: 66)
gccgggcTGGCCGTGCTGCAGCAGCGGTGATatc

cggcCCGACCGGCACGACGTCGTCGCCACTAtag (SEQ ID NO: 67)
BglI                         EcoRV
```

The annealed SD34 oligos were ligated into pET17b-SD22-ELP digested with BglI and EcoRV and 5' dephosphorylated to create pET17b-SD34-ELP.

In this spider construct, the Cys-Cys is placed at the carboxyl terminus of the ELP to create an ELP-protein/peptide orientation.

Individual spider constructs pET17b-SD34-ELP1-90 (SEQ ID NO: 68) and pET17b-SD34-ELP4-60 (SEQ ID NO: 69) were created.

EXAMPLE 7

Construction of Spider Constructs Containing IFNa2bSD

PCR amplification was used to generate the following DNA fragments from a Human cDNA library containing IFNA2b:

IFNa2bSD Nde1-XhoI containing STOP codon:

(SEQ ID NO: 70)
CATAT 5150

GTGTGATCTGCCTCAAACCCACAGCCTGGGTAGCAGGAGGACCTTGATGC 5200

TCCTGGCACAGATGAGGAGAATCTCTCTTTTCTCCTGCTTGAAGGACAGA 5250

CATGACTTTGGATTTCCCCAGGAGGAGTTTGGCAACCAGTTCCAAAAGGC 5300

TGAAACCATCCCTGTCCTCCATGAGATGATCCAGCAGATCTTCAATCTCT 5350

TCAGCACAAAGGACTCATCTGCTGCTTGGGATGAGACCCTCCTAGACAAA 5400

TTCTACACTGAACTCTACCAGCAGCTGAATGACCTGGAAGCCTGTGTGAT 5450

ACAGGGGGTGGGGGTGACAGAGACTCCCCTGATGAAGGAGGACTCCATTC 5500

TGGCTGTGAGGAAATACTTCCAAAGAATCACTCTCTATCTGAAAGAGAAG 5550

AAATACAGCCCTTGTGCCTGGGAGGTTGTCAGAGCAGAAATCATGAGATC 5600

TTTTTCTTTGTCAACAAACTTGCAAGAAAGTTTAAGAAGTAAGGAATAACTCGAG

IFNa2bSD NdeI-XhoI, not containing STOP codon:

(SEQ ID NO: 71)
CATAT 5150

GTGTGATCTGCCTCAAACCCACAGCCTGGGTAGCAGGAGGACCTTGATGC 5200

TCCTGGCACAGATGAGGAGAATCTCTCTTTTCTCCTGCTTGAAGGACAGA 5250

CATGACTTTGGATTTCCCCAGGAGGAGTTTGGCAACCAGTTCCAAAAGGC 5300

TGAAACCATCCCTGTCCTCCATGAGATGATCCAGCAGATCTTCAATCTCT 5350

TCAGCACAAAGGACTCATCTGCTGCTTGGGATGAGACCCTCCTAGACAAA 5400

TTCTACACTGAACTCTACCAGCAGCTGAATGACCTGGAAGCCTGTGTGAT 5450

ACAGGGGGTGGGGGTGACAGAGACTCCCCTGATGAAGGAGGACTCCATTC 5500

TGGCTGTGAGGAAATACTTCCAAAGAATCACTCTCTATCTGAAAGAGAAG 5550

AAATACAGCCCTTGTGCCTGGGAGGTTGTCAGAGCAGAAATCATGAGATC 5600

TTTTTCTTTGTCAACAAACTTGCAAGAAAGTTTAAGAAGTAAGGAACTCGAG

IFNA2bSD with stop codon was ligated into pET17b-SD33-ELP, pET17b-SD34-ELP and pET17b-SD22-ELP digested with NdeI and partially digested with XhoI and 5' dephosphorylated with CIP to create pET17b-SD33-ELP-IFNA2bSD, pET17b-SD34-ELP-IFNA2bSD and pET17b-SD22-ELP-IFNA2bSD respectively.

IFNA2bSD without stop codon was ligated into pET17b-SD35-ELP, pET17b-SD37-ELP and pET17b-SD31-ELP digested with NdeI and partially digested with XhoI and 5' dephosphorylated with CIP to create pET17b-SD35-IFNA2bSD-ELP, pET17b-SD37-IFNA2bSD-ELP and pET17b-SD31-IFNA2bSD-ELP respectively.

Resulting spider constructs created included pET17b-SD33-ELP1-90-IFNA2bSD (SEQ ID NO: 34), pET17b-SD33-ELP4-60-IFNA2bSD (SEQ ID NO: 35), pET17b-SD34-ELP1-90-IFNA2bSD (SEQ ID NO: 36), pET17b-SD34-ELP4-60-IFNA2bSD (SEQ ID NO: 37), pET17b-SD22-ELP1-90-IFNA2bSD (SEQ ID NO: 38), pET17b-SD22-ELP4-60-IFNA2bSD (SEQ ID NO: 39), pET17b-SD35-IFNA2bSD-ELP1-90 (SEQ ID NO: 40), pET17b-SD35-IFNA2bSD-ELP4-60 (SEQ ID NO: 41), pET17b-SD37-IFNA2bSD-ELP1-90 (SEQ ID NO: 42), pET17b-SD37-IFNA2bSD-ELP4-60 (SEQ ID NO: 43), pET17b-SD31-IFNA2bSD-ELP1-90 (SEQ ID NO: 44) and pET17b-SD31-IFNA2bSD-ELP4-60 (SEQ ID NO: 45). Protein translations of these spider constructs are SEQ ID NOs: 22-33.

EXAMPLE 8

Purification of ELP Spider Proteins

*E. coli* strain BL21trxB-(DE3) F-ompT hsdSB(rB-mB-) gal dcm trxB15::kan (DE3) (Novagen) containing the ELP/protein construct was inoculated into 5 ml TB supplemented with 100 mM proline, 4% glycerol, phosphate buffer and ampicillin. Cultures were grown for 5 hrs at 37° C. before being transferred at 1:100 dilutions into the same media and grown for 48 hrs at 25° C. unless otherwise noted. The cultures were harvested and resuspended in 10 ml/gram wet weight in the following buffer: 50 mM Tris pH7.0, 1 mM EDTA. Cells were lysed by ultrasonic disruption on ice for 3 minutes, consisting of 15 second bursts at 60 W separated by 15 second cooling down intervals (Sonicate). Cell debris was removed by centrifugation at 20,000 g at 4° C. for 30 minutes. The insoluble pellet was resuspended in the original buffer and volume (Pellet). Soluble material comprised lysate.

Inverse temperature transition was induced by adding NaCl to a final concentration of 1.0-2.0 M to the lysate at 25° C., followed by centrifugation at 20,000 g for 15 minutes at 25° C. The resulting pellet contained ELP/protein fusions. The pellet was resuspended in the original volume ice-cold ml buffer, centrifuged at 20,000 g, 4° C. for 15 minutes to remove non-specific insoluble proteins ($T_t1$). The temperature transition cycle was repeated at one additional time to increase the purity of the ELP/protein fusions and reduce the final volume ($T_t2$).

The above purification was performed for spider constructs created in Example 8.

Initially the spider constructs were tested after growth for 15 hours at 25° C. and compared to non-spider protein constructs containing IFNa2bSD to determine which were most likely to produce soluble protein. Results are shown in FIG. 8.

Figure 8:
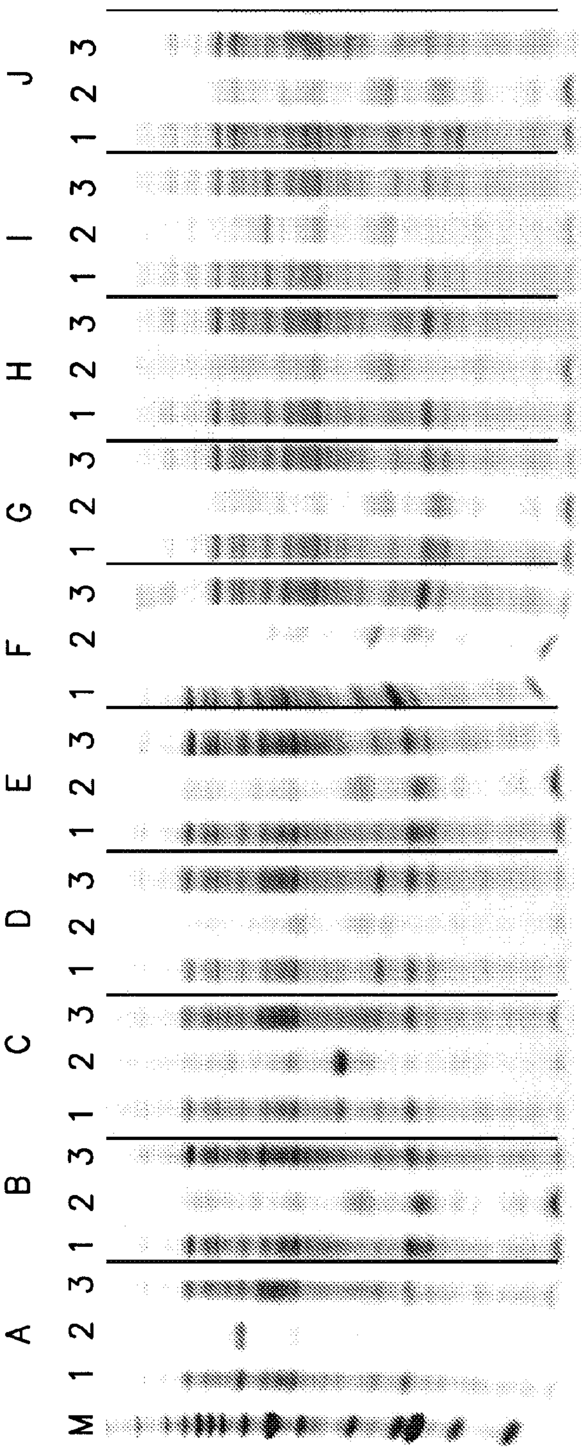
FIG. 8 shows the results of testing of spider constructs grown in Example 8, as compared to non-spider constructs containing IFNa2bSD, in order to determine which were most likely to produce soluble protein.
Figure 9:
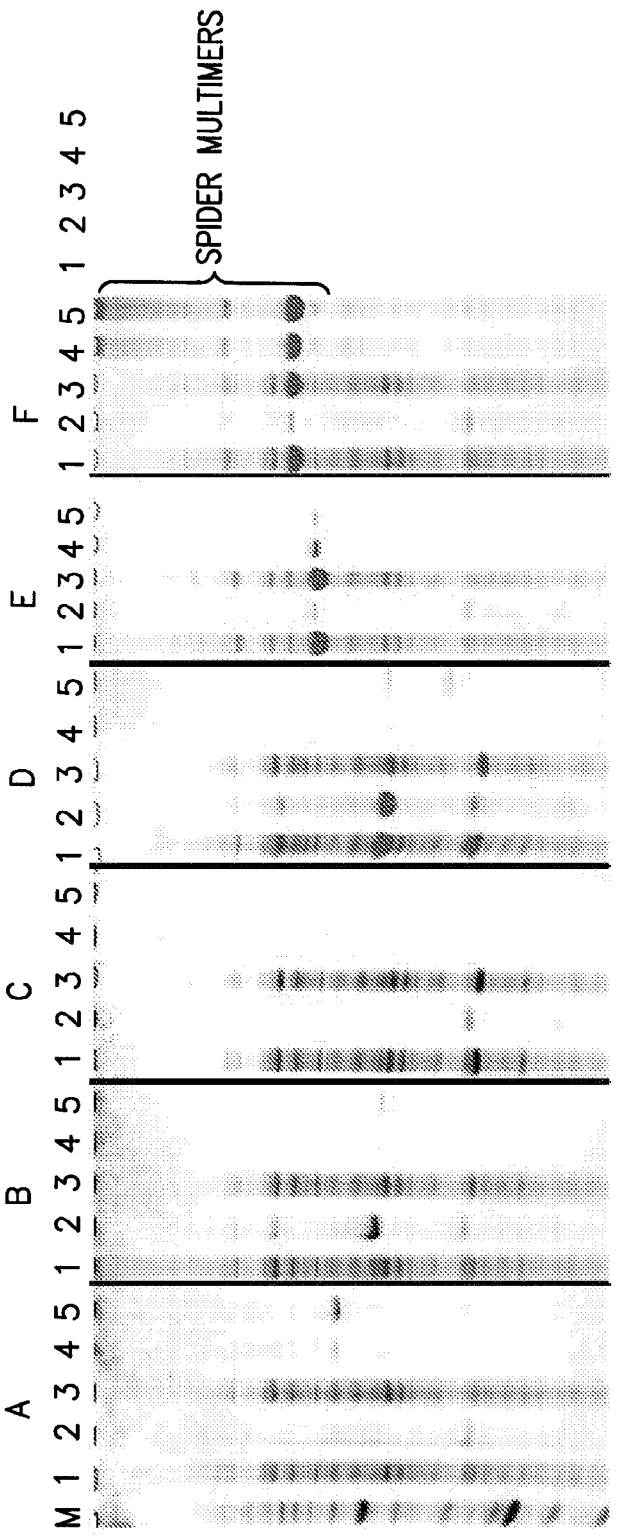
FIG. 9 shows re-expression of selected constructs from FIG. 8. The results of the re-expression show that spider constructs clearly express more target protein than non-spider constructs.

Selected constructs from FIG. 8 were re-expressed for 48 hours at 25° C. and purified using two inverse phase transitions as set forth above. The results of the re-expression are shown in FIG. 9. It can be seen that spider constructs clearly express more initial fusion protein than their non-spider counterparts.

EXAMPLE 9

ELP1-90-TEV1 Cleavage

Figure 10:
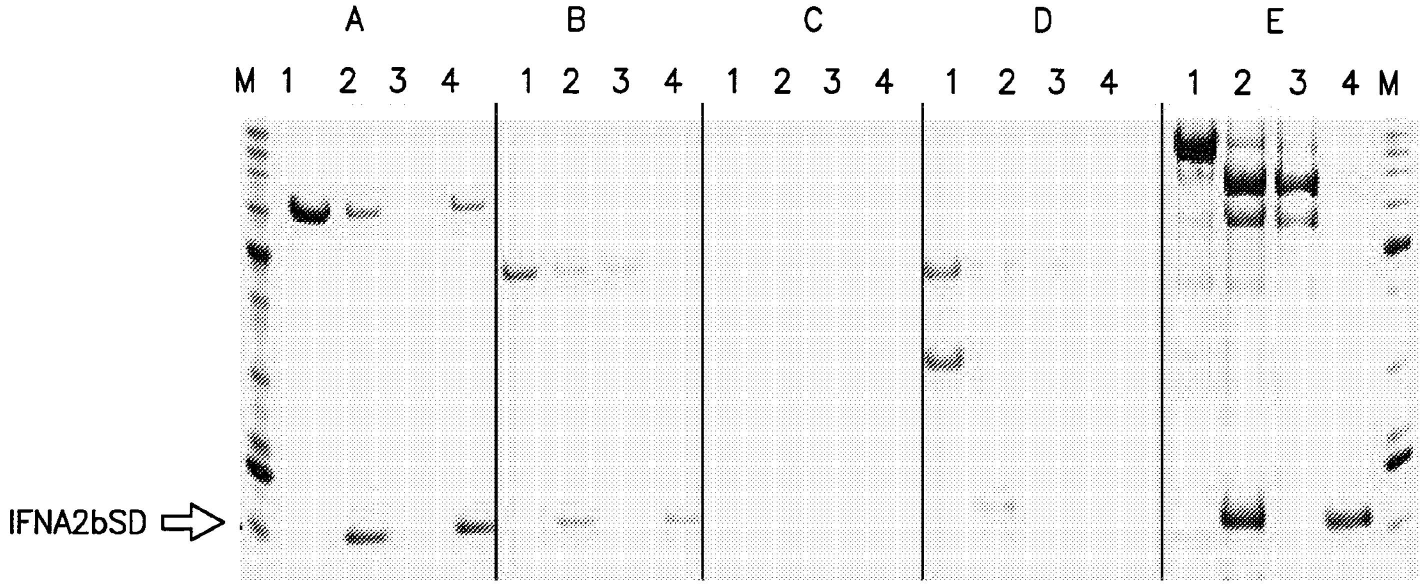
FIG. 10 shows expression of purified target protein obtained after cleavage of each of the constructs. It is shown that the spider constructs express more soluble ELP fusion protein and more IFNa2bSD than non-spider constructs.

In order to purify cleaved protein from ELP, uncleaved protein and protease, the present invention provides an optimized purification of ELP TEV protease (ELP-TEV1) for inverse phase transition removal once cleavage has been completed. ELP1-90-TEV1 was added at a 1:100 dilution of the protein concentration in $T_t2$ and supplemented with 1 mM DTT ($T_t2$ +ELP1-90-TEV1). Cleavage was allowed to proceed for 15 hrs at 4° C. Free protein was separated from free ELP and uncleaved ELP/protein fusions by adding 1M NaCl at 25° C., followed by centrifugation at 25° C. Salt transitioned material (ELP and ELP fusions) were resuspended in cold buffer (Insoluble). Salt soluble protein was transferred to a new tube (Soluble). Results can be seen in FIG. 10. Although TEV cleavage was incomplete when performed at 4° C. rather then 25° C., the spider construct not only expressed more soluble ELP fusion protein but also produced 3-4 times more soluble IFNa2bSD following cleavage with ELP1-90-TEV1 and a final transition to separate IFNa2bSD from free ELP, ELP fusions and ELP1-90-TEV1.

Resulting cleaved proteins were as follows:

```
pET17b-SD33-IFNA2bSD-ELP1-90, cleaved with TEV:
                                        (SEQ ID NO: 72)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE

pET17b-SD33-IFNA2bSD-ELP4-60, cleaved with TEV:
                                        (SEQ ID NO: 73)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE

pET17b-SD34-IFNA2bSD-ELP1-90, cleaved with TEV:
                                        (SEQ ID NO: 74)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE
```

-continued

```
pET17b-SD34-IFNA2bSD-ELP4-60, cleaved with TEV:
                                        (SEQ ID NO: 75)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE

pET17b-SD22-ELP1-90-IFNA2bSD, cleaved with TEV:
                                        (SEQ ID NO: 76)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE

pET17b-SD22-ELP4-60-IFNA2bSD, cleaved with TEV:
                                        (SEQ ID NO: 77)
GAHMCDLPQTHSLGSRRTLMLLAQMRRISLFSCLKDRHDFGFPQEEFGNQ
FQKAETIPVLHEMIQQIFNLFSTKDSSAAWDETLLDKFYTELYQQLNDLE
ACVIQGVGVTETPLMKEDSILAVRKYFQRITLYLKEKKYSPCAWEVVRAE
IMRSFSLSTNLQESLRSKE

pET17b-SD35 -IFNA2bSD-ELP1-90, cleaved with TEV:
                                        (SEQ ID NO: 78)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ

pET17b-SD35-IFNA2bSD-ELP4-60, cleaved with TEV:
                                        (SEQ ID NO: 79)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ

pET17b-SD37-IFNA2bSD-ELP1-90, cleaved with TEV:
                                        (SEQ ID NO: 80)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ

pET17b-SD37-IFNA2bSD-ELP4-60 cleaved with TEV:
                                        (SEQ ID NO: 81)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ

pET17b-SD31-IFNA2bSD-ELP4-60, cleaved with TEV:
                                        (SEQ ID NO: 82)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ

pET17b-SD31-IFNA2bSD-ELP4-60, cleaved with TEV:
                                        (SEQ ID NO: 83)
MCDLPQTHSLGSRRTLMLLAQMRRISLFSCLKDRHDFGFPQEEFGNQFQK
AETIPVLHEMIQQIFNLFSTKDSSAAWDETLLDKFYTELYQQLNDLEACV
IQGVGVTETPLMKEDSILAVRKYFQRITLYLKEKKYSPCAWEVVRAEIMR
SFSLSTNLQESLRSKELENLYFQ
```

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A fusion protein of exhibiting a phase transition, selected from pET17b-SD33-ELP1-90-IFNA2bSD (SEQ ID NO: 22), pET17b-SD33-ELP4-60-IFNA2bSD (SEQ ID NO: 23), pET17b-SD34-ELP1-90-IFNA2bSD (SEQ ID NO: 24), pET17b-SD34-ELP4-60-IFNA2bSD (SEQ ID NO: 25), pET17b-SD22-ELP1-90-IFNA2bSD (SEQ ID NO: 26), pET17b-SD22-ELP4-60-IFNA2bSD (SEQ ID NO: 27), pET17b-SD35-IFNA2 bSD-ELP1-90 (SEQ ID NO: 28), pET17b-SD35-IFNA2bSD-ELP4-60 (SEQ ID NO: 29), pET17b-SD37-IFNA2bSD-ELP1-90 (SEQ ID NO: 30), pET17b-SD37-IFNA2bSD-ELP4-60 (SEQ ID NO: 31), pET17b-SD31-IFNA2bSD-ELP1-90 (SEQ ID NO: 32) and pET17b-SD31-IFNA2bSD-ELP4-60 (SEQ ID NO: 33).

2. An ELP spider complex comprising two or more fusion proteins exhibiting a phase transition, each fusion protein comprising:

a) at least one target protein or peptide;

b) one or more proteins comprising oligomeric repeats of a polypeptide sequence selected from SEQ ID NOs: 1-17, wherein the one or more proteins exhibits a phase transition and are joined to the at least one target protein or peptide of a);

c) at least two residues capable of forming a disulfide bond; and d) optionally, a spacer sequence separating any of the phase transition protein(s) of b) from any of the target protein(s) or peptide(s) of a), and wherein the two or more fusion proteins exhibiting a phase transition are linked by at least one disulfide bond.

3. The ELP spider complex of claim 2, wherein the target protein of at least one fusion protein is interferon alpha-2b (IFNα2b).

4. The ELP spider complex of claim 2, wherein the target protein of at least one fusion protein is Orexin-B, Morphine Modulating Neuropeptide (MMN), Neuropeptide Y (NPY) or Growth Hormone (Gh).

5. The ELP spider complex of claim 2, wherein the phase transition protein of at least one fusion protein is selected from the group consisting of: ELP1-90, ELP1-180, ELP2-64, ELP2-128, ELP3-72, ELP3-144, ELP4-60, ELP4-120, ELP5-15, ELP5-30, ELP5-60, ELP6-15, ELP6-30, ELP6-60, ELP7-15, ELP7-30 and ELP7-60.

6. The ELP spider complex of claim 2, wherein the phase transition is mediatable by one or more of: changing temperature; changing pH; addition of solutes and/or solvents; side chain ionization or chemical modification; and changing pressure.

7. The ELP spider complex of claim 2, wherein the at least two residues capable of forming a disulfide bond comprise cysteine.

8. The ELP spider complex of claim 2, wherein at least one fusion protein exhibiting a phase transition comprises a spacer sequence.

9. The ELP spider complex of claim 8, wherein said spacer sequence comprises a proteolytic cleavage site.

10. The ELP spider complex of claim 2, wherein at least one fusion protein exhibiting a phase transition is selected from pET17b-SD33-ELP1-90-IFNA2bSD (SEQ ID NO: 22), pET17b-SD33-ELP4-60-IFNA2bSD (SEQ ID NO: 23), pET17b-SD34-ELP1-90-IFNA2bSD (SEQ ID NO: 24), pET17b-SD34-ELP4-60-IFNA2bSD (SEQ ID NO: 25), pET17b-SD22-ELP1-90-IFNA2bSD (SEQ ID NO: 26), pET17b-SD22-ELP4-60-IFNA2bSD (SEQ ID NO: 27), pET17b-SD35-IFNA2bSD-ELP1-90 (SEQ ID NO: 28), pET17b-SD35-IFNA2bSD-ELP4-60 (SEQ ID NO: 29), pET17b-SD37-IFNA2bSD-ELP1-90 (SEQ ID NO: 30), pET17b-SD37-IFNA2bSD-ELP4-60 (SEQ ID NO: 31), pET17b-SD31-IFNA2bSD-ELP1-90 (SEQ ID NO: 32) and pET17b-SD31-IFNA2bSD-ELP4-60 (SEQ ID NO: 33).

11. The ELP spider complex of claim 2, wherein at least one fusion protein exhibiting a phase transition is selected from ELP4-60-Orexin B, ELP4-60-MMN, ELP4-60-NPY or ELP4-60-Gh.

* * * * *